(12) United States Patent
Kuo et al.

(10) Patent No.: US 7,015,329 B2
(45) Date of Patent: Mar. 21, 2006

(54) 4-((PHENOXYALKYL)THIO)-PHENOXYACETIC ACIDS AND ANALOGS

(75) Inventors: Gee-Hong Kuo, Scotch Plains, NJ (US); Lan Shen, Annandale, NJ (US); Aihua Wang, Jamison, PA (US); Yan Zhang, Hillsborough, NJ (US)

(73) Assignee: Janssen Pharmaceutica N. V., Beerse (BE)

( * ) Notice: Subject to any disclaimer, the term of this patent is extended or adjusted under 35 U.S.C. 154(b) by 6 days.

(21) Appl. No.: 10/975,785

(22) Filed: Oct. 28, 2004

(65) Prior Publication Data

US 2005/0096362 A1 May 5, 2005

Related U.S. Application Data

(60) Provisional application No. 60/516,561, filed on Oct. 31, 2003.

(51) Int. Cl.
*C07D 285/08* (2006.01)
*A61K 31/41* (2006.01)

(52) U.S. Cl. .................. 548/128; 548/129; 548/130

(58) Field of Classification Search ............... 548/128, 548/129, 130; 514/361
See application file for complete search history.

(56) References Cited

U.S. PATENT DOCUMENTS 6,242,493 B1    6/2001  Gareau et al.
6,506,757 B1 *  1/2003  Tajima et al. .......... 514/254.02

FOREIGN PATENT DOCUMENTS

| WO | WO 99/65881 A1 | 12/1999 | |
|----|----|----|----|
| WO | WO 00/16798 A1 | 3/2000 | |
| WO | WO 00/64876 A1 | 11/2000 | |
| WO | WO 00/64888 A1 | 11/2000 | |
| WO | WO 01/16120 A1 | 3/2001 | |
| WO | WO 02/14291 * | 2/2002 | ............ 514/256 |
| WO | WO 2003084916 * | 10/2003 | ............ 514/345 |
| WO | WO 2004/058174 A2 | 7/2004 | |

OTHER PUBLICATIONS

Chang et al. Substituted Imidazoles as Glucagon Receptor Antagonist, Bioorg. Med. Chem. Letters, 11, pp. 2549-2553 (2001).*
Leibowitz, M.D. et al., "Activation of PPAR δ alters lipid metabolism in db/db mice". 2000, *FEBS. Lett*., pp. 333-336, vol. 473.
Oliver, W.R. Jr., et al., "A selective peroxisome proliferators-activated receptor δ agonist promotes reverse cholesterol transport." 2001, *PNAS*, pp. 5306-5311, vol. 98, No. 9.
PCT International Search Report dated Mar. 29, 2005 for PCT/US2004/036028 which refers to U.S. Appl. No. 10/975,785.
Notification of Transmittal of the International Search Report and the Written Opinion of the International Searching Authority, or the Declaration, 2005.
Written Opinion of the International Searching Authority (PCT Rule 43bls.1), 2005.

* cited by examiner

*Primary Examiner*—Kamal A. Saeed
*Assistant Examiner*—Nyeemah Grazier

(57) ABSTRACT

The invention features 4-((phenoxyalkyl)thio)-phenoxyacetic acids and analogs, compositions containing them, and methods of using them as PPAR modulators to treat or inhibit the progression of, for example, dyslipidemia.

40 Claims, No Drawings

4-((PHENOXYALKYL)THIO)-PHENOXYACETIC ACIDS AND ANALOGS

CROSS-REFERENCE TO RELATED APPLICATIONS

This application claims priority to U.S. Provisional Application No. 60/516,561, filed Oct. 31, 2003.

STATEMENT REGARDING FEDERALLY SPONSORED RESEARCH OR DEVELOPMENT

The research and development of the invention described below was not federally sponsored.

BACKGROUND OF THE INVENTION

The invention features 4-((phenoxyalkyl)thio)-phenoxyacetic acids and analogs, compositions containing them, and methods of using them.

A member of the nuclear receptor family, a group of ligand-activated transcription factors, the peroxisome proliferator-activated receptor alpha (PPAR alpha or PPARα) is a necessary transcription factor regulating genes relating to fatty acid metabolism and insulin action.

PPAR alpha receptors are found predominantly in the liver. The genes regulated by PPAR alpha include enzymes involved in the beta-oxidation of fatty acids, the liver fatty acid transport protein, and apo A1, an important component of high density lipoproteins (HDL). Selective, high affinity PPAR alpha agonists increase hepatic fatty acid oxidation, which in turn decreases circulating triglycerides and free fatty acids. Known as treatments for hyperlipidemia, fibrates are weak PPAR alpha agonists.

Examples of known PPAR alpha agonists variously useful for hyperlipidemia, diabetes, or atherosclerosis include fibrates such as fenofibrate (Fourmier), gemfibrozil (Parke-Davis/Pfizer, Mylan, Watson), clofibrate (Wyeth-Ayerst, Novopharm), bezafibrate, and ciprofibrate and ureidofibrates such as GW 7647, GW 9578, and GW 9820 (GlaxoSmithKline).

Diabetes is a disease caused, or contributed to, by multiple factors and characterized by hyperglycemia which may be associated with increased and premature mortality due to an increased risk for microvascular and macrovascular diseases such as nephropathy, neuropathy, retinopathy, atherosclerosis, polycystic ovary syndrome (PCOS), hypertension, ischemia, stroke, and heart disease. Type I diabetes (IDDM) results from genetic deficiency of insulin, the hormone regulating glucose metabolism. Type II diabetes is known as non-insulin dependent diabetes mellitus (NIDDM), and is due to a profound resistance to insulin regulatory effect on glucose and lipid metabolism in the main insulin-sensitive tissues, i.e., muscle, liver and adipose tissue. This insulin resistance or reduced insulin sensitivity results in insufficient insulin activation of glucose uptake, oxidation and storage in muscle and inadequate insulin repression of lipolysis in adipose tissue as well as glucose production and secretion in liver. Many Type II diabetics are also obese, and obesity is believed to cause and/or exacerbate many health and social problems such as coronary heart disease, stroke, obstructive sleep apnoea, gout, hyperlipidemia, osteoarthritis, reduced fertility, and impaired psychosocial function.

A class of compounds, thiazolidinediones (glitazones), have been suggested to be capable of ameliorating many symptoms of NIDDM by binding to the peroxisome proliferator activated receptor (PPAR) family of receptors. They increase insulin sensitivity in muscle, liver and adipose tissue in several animal models of NIDDM resulting in correction of the elevated plasma levels of glucose, triglycerides and nonesterified free fatty acids without any occurrence of hypoglycemia. However, undesirable effects have occurred in animal and/or human studies including cardiac hypertrophy, hemadilution and liver toxicity.

Many PPARγ agonists currently in development have a thiazolidinedione ring as a common structural element. PPARγ agonists have been demonstrated to be extremely useful for the treatment of NIDDM and other disorders involving insulin resistance. Troglitazone, rosiglitazone, and pioglitazone have been approved for treatment of type II diabetes in the United States. There is also some indication that benzimidazole-containing thiazolidinedione derivatives may be used to treat irritable bowel disorder (IBD), inflammation, and cataracts (JP 10195057).

Cardiovascular disease (CVD) is prevalent in the world and is often associated with other disease states such as diabetes and obesity. Many population studies have attempted to identify the risk factors for CVD; of these, high plasma levels of low density lipoprotein cholesterol (LDL-C), high plasma levels of triglycerides (>200 mg/dl), and low levels of high density lipoprotein cholesterol (HDL-C) are considered to be among the most important. Currently, there are few therapies targeting low HDL-C and triglycerides.

The peroxisome proliferator-activated receptors (PPARs) are metabolic sensors regulating the expression of genes involved in glucose and lipid homeostasis. Agonists of the PPARα subtype, such as LOPID® (gemfibrozil) and TRICOR® (fenofibrate), and agonists of the PPARγ subtype, such as AVANDIA® (rosiglitazone maleate), are used for the treatment of dyslipidemia and diabetes, respectively. Another member of this nuclear receptor family, the peroxisome proliferator-activated receptor delta (PPAR delta or PPARδ) is also a necessary transcription factor reported to be involved in regulating genes involved in lipid metabolism and energy expenditure. PPAR delta has been shown to act as a "gateway" receptor modulating the expression of the other PPARs (Shi et al., 2002, Proc Natl. Acad. Sci USA, 99(5): 2613–2618). Each receptor subtype has a distinct tissue distribution: 1) PPARα shows the highest expression in liver, 2) PPARγ appears primarily in adipose tissue, and 3) PPARδ has the widest distribution—ubiquitously in adult rat (Braissant et al., 1996, Endocrinology 137(1): 354–366) and in all the human tissues tested to date, including liver, kidney, abdominal adipose and skeletal muscle (Auboeuf et al., 1997, Diabetes 46(8):1319–1327).

Recently, potent ligands for PPARδ have been published, providing a better understanding of its function in lipid metabolism. The main effect of these compounds in db/db mice (Leibowitz et al., 2000, FEBS Lett. 473(3):333–336) and obese rhesus monkeys (Oliver et al., 2001, Proc. Natl. Acad. Sci. USA 98(9):5306–5311) was an increase in high density lipoprotein cholesterol (HDL-C) and a decrease in triglycerides, with little effect on glucose (although insulin levels were decreased in monkeys). HDL-C removes cholesterol from peripheral. cells through a process called reverse cholesterol transport. The first and rate-limiting step, a transfer of cellular cholesterol and phospholipids to the apolipoprotein A-I component of HDL, is mediated by the ATP binding cassette transporter A1 (ABCA1) (Lawn et al., 1999, J. Clin. Investigation 104(8): R25–R31). PPARδ activation has been shown to increase HDL-C level through transcriptional regulation of ABCA1 (Oliver et al., 2001, Proc. Natl. Acad. Sci. USA 98(9): 5306–5311). Through induction of ABCA1 mRNA expression in macrophages, PPARδ agonists may increase HDL-C levels in patients and remove excess cholesterol from lipid-laden macrophages, thereby inhibiting the development of atherosclerotic lesions. Existing therapy for hypercholesterolemia includes the statin drugs, which decrease LDL-C but show little effect on HDL-C, and the fibrates, the PPAR a agonists that have low potency and induce only modest HDL-C elevation. In addition, like the fibrates, PPARδ agonists may also reduce triglycerides, an additional risk factor for cardiovascular disease and diabetes. Elevated free fatty acid level has been shown to contribute to insulin resistance and progression of diabetes (Boden, G. PROCEEDINGS OF THE ASSOCIATION OF AMERICAN PHYSICIANS (1999 May–June), 111(3), 241–8).

Examples of known PPAR delta agonists variously useful for hyperlipidemia, diabetes, or atherosclerosis include L-165041 (Leibowitz et al., 2000) and GW501516 (Oliver et al., Proceedings of the National Academy of Sciences of the United States of America (2001), 98(9), 5306–5311). Treatment of differentiated THP-1 monocytes with GW501516 induced ABCA1 mRNA expression and enhanced cholesterol efflux from these cells.

BRIEF SUMMARY OF THE INVENTION

The invention features compounds of Formula (I) below:

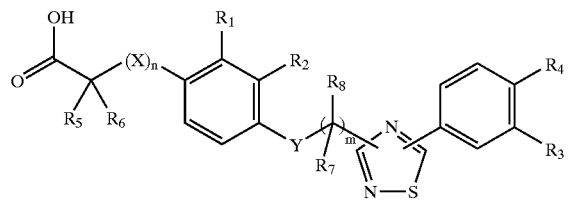

I

Wherein
m is 1, 2 or 3;
n is 0 or 1;
X is S or O;
Y is S, $CH_2$ or O;
$R_1$ and $R_2$ are independently selected from H, $C_{1-4}$ alkyl, $C_{1-3}$ alkoxy, halo, and —$NR_aR_b$, wherein each of $R_a$ and $R_b$ is independently selected from H and $C_{1-4}$ alkyl;

each of $R_3$ and $R_4$ is independently selected from H, halo, cyano, $C_{1-4}$ alkyl, $C_{1-3}$ alkoxy, and $NR_cR_d$, wherein each of $R_c$ and $R_d$ is independently selected from H and $C_{1-4}$ alkyl; and wherein at least one of $R_3$ and $R_4$ is not H; and each of $R_5$ and $R_6$ is independently selected from H, $C_{1-5}$ alkyl, $C_{1-5}$ alkoxy, $C_{3-5}$ cycloalkyl, ($C_{3-5}$ cycloalkyl)$C_{1-3}$ alkyl, and $NR_eR_f$, wherein each of $R_e$ and $R_f$ is independently selected from H and $C_{1-4}$ alkyl; or $R_5$ and $R_6$ together to form spiro $C_{3-6}$ cycloalkyl, or spiro 5- or 6-membered heterocyclyl having between 1 and 3 heteroatoms selected from O, S, and N; and each of $R_7$ and $R_8$ is independently selected from H, $C_{1-5}$ alkyl, and $C_{3-5}$ cycloalkyl;

or a pharmaceutically acceptable salt thereof.

The invention also features compositions that include one or more compounds of Formula (I) and a pharmaceutical carrier or excipient.

These compositions and the methods below may further include additional pharmaceutically active agents, such as lipid-lowering agents or blood-pressure lowering agents, or both.

Another aspect of the invention includes methods of using the disclosed compounds or compositions in various methods for treating, preventing, or inhibiting the progression of, a condition directly or indirectly mediated by PPAR delta. Said condition includes, but is not limited to, diabetes, nephropathy, neuropathy, retinopathy, polycystic ovary syndrome, hypertension, ischemia, stroke, irritable bowel disorder, inflammation, cataract, cardiovascular diseases, Metabolic X Syndrome, hyper-LDL-cholesterolemia, dyslipidemia (including hypertriglyceridemia, hypercholesterolemia, mixed hyperlipidemia, and hypo-HDL-cholesterolemia), atherosclerosis, obesity, and other disorders related to lipid metabolism and energy homeostasis complications thereof.

One embodiment of the present invention is a method for treating a PPAR mediated condition, such as a PPAR delta-mediated condition and optionally one or more PPAR alpha- or PPAR gamma-mediated conditions, which PPAR alpha- or PPAR gamma-mediated condition(s) may be the same as or different from said PPAR delta-mediated condition, said method comprising administering to a patient in need of treatment a pharmaceutically effective amount of a compound or composition described herein.

Another embodiment of the present invention is a method for inhibiting the onset and/or inhibiting the progression of a PPAR delta-mediated condition, said method comprising administering to a patient in need of treatment a pharmaceutically effective amount of a compound or composition described herein.

Examples of conditions that can be treated with a PPAR-delta agonist include, without limitation, diabetes, cardiovascular diseases, Metabolic X Syndrome, hypercholesterolemia, hypo-HDL-cholesterolemia, hyper-LDL-cholesterolemia, dyslipidemia, atherosclerosis, and obesity. Dyslipidemia includes hypertriglyceridemia, and mixed hyperlipidemia. For example, dyslipidemia (including hyperlipidemia) may be one or more of the following conditions: low HDL (<35 or 40 mg/dl), high triglycerides (>200 mg/dl), and high LDL (>150 mg/dl).

Examples of conditions that can be treated with a PPAR alpha-agonist include Syndrome X (or Metabolic Syndrome), dyslipidemia, high blood pressure, obesity, impaired fasting glucose, insulin resistance, type II diabetes, atherosclerosis, hypercholesterolemia, hypertriglyceridemia, and non-alcoholic steatohepatitis.

Additional features and advantages of the invention will become apparent from the detailed discussion, examples, and claims below.

DETAILED DESCRIPTION

The invention features compositions containing compounds of Formula (I) in the above Summary section, and methods of using them.

Preferred compounds of the invention are PPAR delta agonists that have at least one and preferably two or three of the following characteristics when administered to patients with hypercholesterolemia, hypertriglyceridemia, low-HDL-C, obesity, diabetes and/or Metabolic X Syndrome: 1) increasing HDL-C level, 2) lowering triglycerides, 3) lowering free fatty acids, and 4) decreasing insulin levels. Improvement in HDL-C and triglyceride levels is beneficial for cardiovascular health. In addition, decreased level of triglycerides and free fatty acids contributes to reduce obesity and ameliorate or prevent diabetes.

According to one aspect of the invention, the compounds of the invention are dual PPAR compounds, in other words, they are both PPAR delta agonists and PPAR alpha agonists, preferably where the compound's $EC_{50}$ potency relating to PPAR delta is less than 0.2 $\mu$M and the potency relating to PPAR alpha is less than 3 $\mu$M. For example, more preferred dual PPAR alpha-delta agonists are those compounds having an $EC_{50}$ potency relating to PPAR delta that is less than 0.03 $\mu$M and where the potency relating to PPAR alpha is less than 1 $\mu$M.

According to another aspect of the invention, the compounds of the invention are pan-PPAR agonists, namely, compounds having PPAR alpha, PPAR delta, and PPAR gamma agonist activity, preferably where the $EC_{50}$ potency for PPAR delta is less than 0.2 $\mu$M; the potency for PPAR alpha is less than 3 $\mu$M; and the potency for PPAR gamma is less than 1 $\mu$M. More preferred pan-PPAR agonists have an $EC_{50}$ potency for PPAR delta that is less than 0.03 $\mu$M; a potency for PPAR alpha that is less than 1 $\mu$M; and a potency for PPAR gamma that is less than 0.7 $\mu$M.

PPAR delta, being ubiquitously expressed, can act as a gateway receptor that regulates the expression/activity of other nuclear receptors such as other PPARs. For instance, PPAR delta has been shown to block PPAR$\gamma$-mediated adipogenesis and acyl-CoA oxidase expression; it has also been shown to be associated with the nuclear receptor corepressors SMRT (silencing mediator for retinoid and thyroid hormone receptors), SHARP (SMART and histone deacetylase-associated repressor protein), and HDACs (histone deacetylase). Thus, conditions directly mediated by these nuclear receptors, such as obesity and type II diabetes, can be indirectly mediated by PPAR delta (See, for example, Shi et al., 2002, Proc Natl. Acad. Sci USA, 99(5): 2613–2618).

Some aspects of the invention relate to treating hypertriglyceridemia, raising levels of HDL, lowering levels of LDL, and/or lowering total cholesterol. Preferably, the methods of treatment are associated with improvements in the extent, duration, or degree of side effects, such as edema, normally associated with other existing therapies.

The invention is further described below. The specification is arranged as follows: A) Terms; B) Compounds; C) Synthesis; D) Formulation and Administration; E) Use; F) Biological Examples; G) Other Embodiments; and claims.

A. Terms

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation, prevention, treatment, or the delay of the onset or progression of the symptoms of the disease or disorder being treated.

Conditions directly or indirectly mediated by PPAR include, but are not limited to, diabetes, nephropathy, neuropathy, retinopathy, polycystic ovary syndrome, hypertension, ischemia, stroke, irritable bowel disorder, inflammation, cataract, cardiovascular diseases, Metabolic X Syndrome, hyper-LDL-cholesterolemia, dyslipidemia (including hypertriglyceridemia, hypercholesterolemia, mixed hyperlipidemia, and hypo-HDL-cholesterolemia), atherosclerosis, obesity, and other disorders related to lipid metabolism and energy homeostasis complications thereof.

For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together.

Unless otherwise noted, as used herein and whether used alone or as part of a substituent group, "alkyl" and "alkoxy" include straight and branched chains having 1 to 8 carbon atoms, such as $C_{1-6}$, $C_{1-4}$, $C_{3-8}$, $C_{2-5}$, or any other range, and unless otherwise noted, include both substituted and unsubstituted moieties. For example, $C_{1-6}$alkyl radicals include methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Alkoxy radicals are formed from the previously described straight or branched chain alkyl groups. "Alkyl" and "alkoxy" include unsubstituted or substituted moieties with one or more substitutions, such as between 1 and 5, 1 and 3, or 2 and 4 substituents. The substituents may be the same (dihydroxy, dimethyl), similar (chloro, fluoro), or different (chlorobenzyl- or aminomethyl-substituted). Examples of substituted alkyl include haloalkyl (such as fluoromethyl, chloromethyl, difluoromethyl, perchloromethyl, 2-bromoethyl, trifluoromethyl, and 3-iodocyclopentyl), hydroxyalkyl (such as hydroxymethyl, hydroxyethyl, 2-hydroxypropyl), aminoalkyl (such as aminomethyl, 2-aminoethyl, 3-aminopropyl, and 2-aminopropyl), alkoxylalkyl, nitroalkyl, alkylalkyl, cyanoalkyl, phenylalkyl, heteroarylalkyl, heterocyclylalkyl, phenoxyalkyl, heteroaryloxyalkyl (such as 2-pyridyloxyalkyl), heterocyclyloxyalkyl (such as 2-tetrahydropyranoxy-alkyl), thioalkylalkyl (such as MeS-alkyl), thiophenylalkyl (such as phS-alkyl), carboxylalkyl, and so on. A di($C_{1-3}$ alkyl)amino group includes independently selected alkyl groups, to form, for example, methylpropylamino and isopropylmethylamino, in addition dialkylamino groups having two of the same alkyl group such as dimethyl amino or dieithylamino.

The term "alkenyl" includes optionally substituted straight chain and branched hydrocarbon radicals as above with at least one carbon-carbon double bond ($sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbon radicals having a mixture of double bonds and triple bonds, such as 2-penten-4-ynyl, are grouped as alkynyls herein. Alkenyl includes cycloalkenyl. Cis and trans or (E) and (Z) forms are included within the invention. "Alkenyl" may be substituted with one or more substitutions including, but not limited to, cyanoalkenyl, and thioalkenyl.

The term "alkynyl" includes optionally substituted straight chain and branched hydrocarbon radicals as above with at least one carbon-carbon triple bond (sp). Alkynyls include ethynyl, propynyls, butynyls, and pentynyls. Hydrocarbon radicals having a mixture of double bonds and triple bonds, such as 2-penten-4-ynyl, are grouped as alkynyls herein. Alkynyl does not include cycloalkynyl.

The term "Ac" as used herein, whether used alone or as part of a substituent group, means acetyl ($CH_3CO$—). The term "acyl" as used herein, referes to a substituent that has a carbonyl group (C=O) and one or more alkyl or alkylene groups. For example, $C_{2-4}$ acyl includes without limitation, acetyl, $CH_3CH_2$—(C=O)—$CH_2$—, and $CH_3CH_2CH_2$(C=O)—.

The term "halogen" or "halo" shall include iodo, bromo, chloro and fluoro.

The terms "aryl" or "Ar" as used herein refer to an unsubstituted or substituted aromatic hydrocarbon ring system such as phenyl and naphthyl. When the Ar or aryl group is substituted, it may have one to three substituents which are independently selected from $C_1$–$C_8$ alkyl, $C_1$–$C_8$ alkoxy, fluorinated $C_1$–$C_8$ alkyl (e.g., trifluoromethyl), fluorinated $C_1$–$C_8$ alkoxy (e.g., trifluoromethoxy), halogen, cyano, $C_1$–$C_8$ alkylcarbonyl such as acetyl, carboxyl, hydroxy, amino, nitro, $C_1$–$C_4$ alkylamino (i.e., —NH—$C_1$–$C_4$ alkyl), $C_1$–$C_4$ dialkylamino (i.e., —N—[$C_1$–$C_4$ alkyl]$_2$ wherein the alkyl groups can be the same or different), or unsubstituted, mono-, di- or tri-substituted phenyl wherein the substituents on the phenyl are independently selected from $C_1$–$C_8$ alkyl, $C_1$–$C_8$ alkoxy, fluorinated $C_1$–$C_8$ alkyl, fluorinated $C_1$–$C_8$ alkoxy, halogen, cyano, acetyl, carboxyl, hydroxy, amino, nitro, alkylamino, dialkylamino or five or six membered heteroaryl having 1–3 heteroatoms selected from N, O and S.

The term "heteroaryl" as used herein represents a stable, unsubstituted or substituted five or six membered monocyclic or bicyclic aromatic ring system which consists of carbon atoms and from one to three heteroatoms selected from N, O and S. The heteroaryl group may be attached at any heteroatom or carbon atom which results in the creation of a stable structure. Examples of heteroaryl groups include, but are not limited to, benzimidazolyl, benzisoxazolyl, benzofuranyl, benzopyrazolyl, benzothiadiazolyl, benzothiazolyl, benzothienyl, benzotriazolyl, benzoxazolyl, furanyl, furazanyl, furyl, imidazolyl, indazolyl, indolizinyl, indolinyl, indolyl, isobenzofuranyl, isoindolyl, isothiazolyl, isoxazolyl, oxazolyl, purinyl, pyrazinyl, pyrazolyl, pyridazinyl, pyridinyl, pyrimidinyl, pyrrolyl, quinolinyl, quinolyl, thiadiazolyl, thiazolyl, thiophenyl, or triazolyl. When the heteroaryl group is substituted, the heteroaryl group may have one to three substituents including, but not limited to, $C_1$–$C_8$ alkyl, halogen, and aryl.

The term "heterocyclyl" includes optionally substituted nonaromatic rings having carbon atoms and at least one heteroatom (O, S, N) or heteroatom moiety ($SO_2$, CO, CONH, COO) in the ring. A heterocyclyl may be saturated, partially saturated, nonaromatic, or fused. Examples of heterocyclyl include cyclohexylimino, imdazolidinyl, imidazolinyl, morpholinyl, piperazinyl, piperidyl, pyridyl, pyranyl, pyrazolidinyl, pyrazolinyl, pyrrolidinyl, pyrrolinyl, and thienyl.

Unless otherwise indicated, heteroaryl and heterocyclyl may have a valence connecting it to the rest of the molecule through a carbon atom, such as 3-furyl or 2-imidazolyl, or through a heteroatom, such as N-piperidyl or 1-pyrazolyl. Preferably a monocyclic heterocyclyl has between 5 and 7 ring atoms, or between 5 and 6 ring atoms; there may be between 1 and 5 heteroatoms or heteroatom moieties in the ring, and preferably between 1 and 3, or between 1 and 2 heteroatoms or heteroatom moieties.

Heterocyclyl and heteroaryl also include fused, e.g., bicyclic, rings, such as those optionally fused with an optionally substituted carbocyclic or heterocyclic five- or six-membered aromatic ring. For example, "heteroaryl" includes an optionally substituted six-membered heteroaromatic ring containing 1, 2 or 3 nitrogen atoms fused with an optionally substituted five- or six-membered carbocyclic or heterocyclic aromatic ring. Said heterocyclic five- or six-membered aromatic ring fused with the said five- or six-membered aromatic ring may contain 1, 2 or 3 nitrogen atoms where it is a six-membered ring, or 1, 2 or 3 heteroatoms selected from oxygen, nitrogen and sulfur where it is a five-membered ring.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Where chemical moieties are combined, such as in ethoxymethyl or phenylethyl, the term is described in the direction from the periphery to the connection point of the rest of the molecule. For example, ethoxymethyl is $CH_3CH_2OCH_2$— and phenylethyl is a phenyl group linked by —$CH_2CH_2$— to the rest of the molecule (and not a phenyl group linked to the molecule with a $CH_3CH_2$ group as a substituent on the phenyl.) Where parentheses are used, they indicate a peripheral substitution.

As used herein, the term "composition" is intended to encompass a product comprising the specified ingredients in the specified amounts, as well as any product which results, directly or indirectly, from combinations of the specified ingredients in the specified amounts.

Compounds of the invention are further described in the next section.

B. Compounds

The present invention features compositions containing and methods of using compounds of Formula (I) as described above. Unless otherwise noted, in Formula (I), each hydrocarbyl (alkyl, alkenyl, alkynyl, cycloalkyl, cycloalkenyl, etc) or heterocarbyl (heterocyclyl, heteroaryl, heteroatom moiety such as sulfonyl, amino, amido, etc.) may be substituted or unsubstituted, for example, "alkyl" includes substituted and unsubstituted alkyl and "heterocyclyl" and "aryl" and "alkoxy" and so on, may also be substituted or unsubstituted. For example, where $R_4$ is "methyl or methoxy", unless otherwise indicated, these terms collectively include: methyl, methoxy, trifluoromethyl, trifluoromethoxy, difluoromethyl, difluoromethoxy, fluoromethyl, fluoromethoxy, chlorodifluoromethyl, chlorodifluoromethoxy, dichlorofluoromethyl, and dichlorofluoromethoxy, and so on.

Examples of compounds of the invention include compounds of Formula (I) wherein: (a) m is 1 or 2; (b) m is 1; (c) n is 1; (d) X is O; Y is S or O; (e) Y is S; (f) $R_1$ is selected from H, $C_{1-2}$ alkyl, $C_{1-2}$ alkoxy and halo; (g) $R_1$ is selected from halo, methyl, and methoxy, and if methyl or methoxy, $R_1$ may be substituted or unsubstituted; (h) $R_2$ is H, halo, methoxy, or methyl; (i) $R_2$ is H, fluoro, or chloro; (j) each of $R_3$ and $R_4$ is independently selected from H, halo, $C_{1-4}$alkyl, $C_{1-3}$ alkoxy, and $NR_cR_d$; (k) each of $R_3$ and $R_4$ is independently selected from H, fluoro, chloro, $C_{1-2}$ alkyl, and $C_{1-2}$ alkoxy; (l) each of $R_3$ and $R_4$ is independently selected from H, fluoro, chloro, methyl, methoxy, trifluoromethyl, trifluoromethoxy, difluoromethyl, difluoromethoxy, fluoromethyl, fluoromethoxy, trifluoroethyl, and trifluoroethoxy; (m) each of $R_5$ and $R_6$ is independently selected from H, $C_{1-3}$ alkyl, and $C_{1-3}$ alkoxy; (n) at least one of $R_5$ and $R_6$ Is methyl, methoxy, ethyl, and ethoxy; and the other is selected from H, methoxy, methyl, ethyl, and ethoxy; (o) each of $R_7$ and $R_8$ is independently selected from H and $C_{1-3}$ alkyl; (p) one of $R_7$ and $R_8$ is H and the other is H, methyl, or ethyl; (q) each of $R_7$ and $R_8$ is H; (r) X is O; Y is S or O; $R_1$ is selected from H, $C_{1-2}$ alkyl, $C_{1-2}$ alkoxy, and halo; each of $R_5$ and $R_6$ is independently selected from H, $C_{1-3}$ alkyl, and $C_{1-3}$ alkoxy; and each of $R_7$ and $R_8$ is independently selected from H and $C_{1-3}$ alkyl; (s) m is 1 or 2 and n is 1; (t) each of $R_3$ and $R_4$ is independently selected from H, fluoro, chloro, $C_{1-2}$ alkyl, and $C_{1-2}$ alkoxy; and $R_1$ is selected from H, $C_{1-2}$ alkyl, $C_{1-2}$ alkoxy and halo; (u) each of $R_3$ and $R_4$ is independently selected from H, fluoro, chloro, methyl, methoxy, trifluoromethyl, trifluoromethoxy, trifluoroethyl, and trifluoroethoxy; or combinations of the above.

Examples of compounds of formula (I) also include those wherein: (v) m is 1 or 2; n is 0 or 1; X is S or O; Y is S, $CH_2$ or O; $R_1$ and $R_2$ are independently selected from H, $C_{1-4}$ alkyl, $C_{1-3}$ alkoxy, halo, and —$NR_aR_b$, wherein each of $R_a$ and $R_b$ is independently selected from H and $C_{1-4}$ alkyl; each of $R_3$ and $R_4$ is independently selected from H, halo, cyano, $C_{1-4}$ alkyl, $C_{1-3}$ alkoxy, and $NR_cR_d$, wherein each of $R_c$ and $R_d$ is independently selected from H and $C_{1-4}$ alkyl; and wherein at least one of $R_3$ and $R_4$ is not H; and each of $R_5$ and $R_6$ is independently selected from H, $C_{1-5}$ alkyl, $C_{1-5}$ alkoxy, $C_{3-5}$ cycloalkyl, ($C_{3-5}$ cycloalkyl)$C_{1-3}$ alkyl, and $NR_eR_f$, wherein each of $R_e$ and $R_f$ is independently selected from H and $C_{1-4}$ alkyl; or $R_5$ and $R_6$ together to form spiro $C_{3-6}$ cycloalkyl; and each of $R_7$ and $R_8$ is independently selected from H and $C_{1-2}$ alkyl.

Example of compounds of formula (I) also include those compounds wherein: (w) m is 1 or 2; n is 0 or 1; X is S or O; Y is S or O; $R_1$ and $R_2$ are independently selected from H, $C_{1-2}$ alkyl, $C_{1-2}$ alkoxy, halo, and —$NR_aR_b$, wherein each of $R_a$ and $R_b$ is independently selected from H and $C_{1-4}$ alkyl; each of $R_3$ and $R_4$ is independently selected from H, halo, cyano, $C_{1-4}$ alkyl, $C_{1-3}$ alkoxy, and $NR_cR_d$, wherein each of $R_c$ and $R_d$ is independently selected from H and $C_{1-4}$ alkyl; and wherein at least one of $R_3$ and $R_4$ is not H; and each of $R_5$ and $R_6$ is independently selected from H, $C_{1-3}$ alkyl, $C_{1-2}$ alkoxy; and each of $R_7$ and $R_8$ is H.

Specific examples of compounds of formula (I) include:
2-Methyl-2-[2-methyl-4-(3-p-tolyl-[1,2,4]thiadiazol-5-ylmethylsulfanyl)-phenoxy]-propionic acid;
2-Methyl-2-{2-methyl-4-[3-(4-trifluoromethyl-phenyl)-[1,2,4]thiadiazol-5-ylmethoxy]-phenoxy}-propionic acid
2-{4-[3-(4-tert-Butyl-phenyl)-[1,2,4]thiadiazol-5-ylmethylsulfanyl]-2-methyl-phenoxy}-2-methyl-propionic acid;
2-{4-[3-(4-Chloro-phenyl)-[1,2,4]thiadiazol-5-ylmethylsulfanyl]-2-methyl-phenoxy}-2-methyl-propionic acid;
2-{4-[3-(3-Chloro-4-trifluoromethoxy-phenyl)-[1,2,4]thiadiazol-5-ylmethylsulfanyl]-2-methyl-phenoxy}-2-methyl-propionic acid;
2-{4-[3-(3,4-Dichloro-phenyl)-[1,2,4]thiadiazol-5-ylmethylsulfanyl]-2-methyl-phenoxy}-2-methyl-propionic acid;
2-{4-[3-(2,4-Dichloro-phenyl)-[1,2,4]thiadiazol-5-ylmethylsulfanyl]-2-methyl-phenoxy}-2-methyl-propionic acid;
2-{4-[3-(3,4-Dimethyl-phenyl)-[1,2,4]thiadiazol-5-ylmethylsulfanyl]-2-methyl-phenoxy}-2-methyl-propionic acid;
2-{4-[3-(3-Chloro-4-methyl-phenyl)-[1,2,4]thiadiazol-5-ylmethylsulfanyl]-2-methyl-phenoxy}-2-methyl-propionic acid;
2-{4-[3-(3-Fluoro-4-trifluoromethyl-phenyl)-[1,2,4]thiadiazol-5-ylmethylsulfanyl]-2-methyl-phenoxy}-2-methyl-propionic acid;
1-{2-Methyl-4-[3-(4-trifluoromethoxy-phenyl)-[1,2,4]thiadiazol-5-ylmethylsulfanyl]-phenoxy}-cyclopentanecarboxylic acid;
1-{4-[3-(3,4-Dichloro-phenyl)-[1,2,4]thiadiazol-5-ylmethylsulfanyl]-2-methyl-phenoxy}-cyclopentanecarboxylic acid;
2-Methyl-2-{2-methyl-4-[5-(4-trifluoromethyl-phenyl)-[1,2,4]thiadiazol-3-ylmethylsulfanyl]-phenoxy}-propionic acid;
2-{4-[5-(4-Chloro-phenyl)-[1,2,4]thiadiazol-3-ylmethylsulfanyl]-2-methyl-phenoxy}-2-methyl-propionic acid;
2-{4-[5-(4-Isopropyl-phenyl)-[1,2,4]thiadiazol-3-ylmethylsulfanyl]-2-methyl-phenoxy}-2-methyl-propionic acid;
2-Methyl-2-{2-methyl-4-[5-(4-trifluoromethoxy-phenyl)-[1,2,4]thiadiazol-3-ylmethylsulfanyl]-phenoxy}-propionic acid;
2-{4-[5-(4-tert-Butyl-phenyl)-[1,2,4]thiadiazol-3-ylmethylsulfanyl]-2-methyl-phenoxy}-2-methyl-propionic acid;
2-Methyl-2-{2-methyl-4-[3-(4-trifluoromethoxy-phenyl)-[1,2,4]thiadiazol-5-ylmethylsulfanyl]-phenoxy}-propionic acid;
{2-Methyl-4-[3-(4-trifluoromethyl-phenyl)-[1,2,4]thiadiazol-5-ylmethylsulfanyl]-phenoxy}-acetic acid;
2-Methyl-2-{2-methyl-4-[3-(4-trifluoromethyl-phenyl)-[1,2,4]thiadiazol-5-ylmethylsulfanyl]-phenoxy}-propionic acid; and
2-Methyl-2-{4-[3-(4-trifluoromethyl-phenyl)-[1,2,4]thiadiazol-5-ylmethylsulfanyl]-phenoxy}-propionic acid.

According to one aspect, preferred compounds include
2-Methyl-2-{2-methyl-4-[3-(4-trifluoromethyl-phenyl)-[1,2,4]thiadiazol-5-ylmethoxy]-phenoxy}-propionic acid
2-Methyl-2-{2-methyl-4-[3-(4-trifluoromethoxy-phenyl)-[1,2,4]thiadiazol-5-ylmethylsulfanyl]-phenoxy}-propionic acid
2-{4-[3-(3-Chloro-4-trifluoromethoxy-phenyl)-[1,2,4]thiadiazol-5-ylmethylsulfanyl]-2-methyl-phenoxy}-2-methyl-propionic acid
2-{4-[3-(3,4-Dichloro-phenyl)-[1,2,4]thiadiazol-5-ylmethylsulfanyl]-2-methyl-phenoxy}-2-methyl-propionic acid
2-Methyl-2-{2-methyl-4-[3-(4-trifluoromethoxy-phenyl)-[1,2,4]thiadiazol-5-ylmethylsulfanyl]-phenylsulfanyl}-propionic acid
2-{4-[3-(3,4-Dichloro-phenyl)-[1,2,4]thiadiazol-5-ylmethylsulfanyl]-2-methyl-phenylsulfanyl}-2-methyl-propionic acid 2-{4-[3-(3-Chloro-4-trifluoromethoxy-phenyl)-[1,2,4]thiadiazol-5-ylmethylsulfanyl]-2-methyl-phenylsulfanyl}-2-methyl-propionic acid 2-{4-[3-(4-tert-Butyl-phenyl)-[1,2,4]thiadiazol-5-ylmethylsulfanyl]-2-methyl-phenylsulfanyl}-2-methyl-propionic acid and 2-Methyl-2-(2-methyl-4-{3-[3-(4-trifluoromethoxy-phenyl)-[1,2,4]thiadiazol-5-yl]-propyl}-phenoxy)-propionic acid According to another aspect, preferred compounds include:

2-Methyl-2-{2-methyl-4-[3-(4-trifluoromethyl-phenyl)-[1,2,4]thiadiazol-5-ylmethylsulfanyl]-phenoxy}-propionic acid 2-Methyl-2-(2-methyl-4-{2-[3-(4-trifluoromethyl-phenyl)-[1,2,4]thiadiazol-5-yl]-ethyl}-phenoxy)-propionic acid 2-(4-{2-[3-(3-Chloro-4-trifluoromethyl-phenyl)-[1,2,4]thiadiazol-5-yl]-ethyl}-2-methyl-phenoxy)-2-methyl-propionic acid 2-(4-{2-[3-(3-Fluoro-4-trifluoromethyl-phenyl)-[1,2,4]thiadiazol-5-yl]-ethyl}-2-methyl-phenoxy)-2-methyl-propionic acid 2-(4-{2-[3-(3-Fluoro-4-methyl-phenyl)-[1,2,4]thiadiazol-5-yl]-ethyl}-2-methyl-phenoxy)-2-methyl-propionic acid 2-Methyl-2-(2-methyl-4-{2-[3-(4-trifluoromethyl-phenyl)-[1,2,4]-thiadiazol-5-yl]-ethylsulfanyl}-phenoxy)-propionic acid 2-(4-{2-[3-(3-Chloro-4-trifluoromethyl-phenyl)-[1,2,4]thiadiazol-5-yl]-ethylsulfanyl}-2-methyl-phenoxy)-2-methyl-propionic acid 2-(4-{2-[3-(3-Chloro-4-trifluoromethyl-phenyl)-[1,2,4]thiadiazol-5-yl]-ethylsulfanyl}-2-methyl-phenoxy)-2-methyl-propionic acid 2-Methyl-2-{2-methyl-4-[3-(4-trifluoromethyl-phenyl)-[1,2,4]thiadiazol-5-ylmethylsulfanyl]-phenylsulfanyl}-propionic acid 2-{4-[3-(3-Chloro-4-trifluoromethyl-phenyl)-[1,2,4]thiadiazol-5-yl-methylsulfanyl]-2-methyl-phenylsulfanyl}-2-methyl-propionic acid 2-{4-[3-(3-Fluoro-4-trifluoromethyl-phenyl)-[1,2,4]thiadiazol-5-ylmethylsulfanyl]-2-methyl-phenylsulfanyl}-2-methyl-propionic acid 2-{4-[3-(3-Fluoro-4-methyl-phenyl)-[1,2,4]thiadiazol-5-ylmethylsulfanyl]-2-methyl-phenylsulfanyl}-2-methyl-propionic acid Examples of the most preferred compounds include:

2-Methyl-2-{2-methyl-4-[3-(4-trifluoromethyl-phenyl)-[1,2,4]thiadiazol-5-ylmethoxy]-phenoxy}-propionic acid 2-Methyl-2-{2-methyl-4-[3-(4-trifluoromethoxy-phenyl)-[1,2,4]thiadiazol-5-ylmethoxy]-phenoxy}-propionic acid 2-Methyl-2-{2-methyl-4-[3-(4-trifluoromethoxy-phenyl)-[1,2,4]thiadiazol-5-ylmethylsulfanyl]-phenoxy}-propionic acid 2-{4-[3-(3,4-Dichloro-phenyl)-[1,2,4]thiadiazol-5-ylmethylsulfanyl]-2-methyl-phenoxy}-2-methyl-propionic acid, and 2-{4-[3-(3-Chloro-4-trifluoromethoxy-phenyl)-[1,2,4]thiadiazol-5-ylmethylsulfanyl]-2-methyl-phenoxy}-2-methyl-propionic acid.

Additional preferred compounds include

2-Methyl-2-{2-methyl-4-[3-(4-trifluoromethoxy-phenyl)-[1,2,4]thiadiazol-5-ylmethoxy]-phenoxy}-propionic acid 2-{4-[3-(3,4-Dichloro-phenyl)-[1,2,4]thiadiazol-5-ylmethoxy]-2-methyl-phenoxy}-2-methyl-propionic acid 2-{4-[3-(3-Chloro-4-trifluoromethoxy-phenyl)-[1,2,4]thiadiazol-5-ylmethoxy]-2-methyl-phenoxy}-2-methyl-propionic acid 2-Methyl-2-(2-methyl-4-{2-[3-(4-trifluoromethoxy-phenyl)-[1,2,4]thiadiazol-5-yl]-ethoxy}-phenoxy)-propionic acid 2-(4-{2-[3-(3,4-Dichloro-phenyl)-[1,2,4]thiadiazol-5-yl]-ethyl}-2-methyl-phenoxy)-2-methyl-propionicacid 2-Methyl-2-(2-methyl-4-{2-[3-(4-trifluoromethoxy-phenyl)-[1,2,4]thiadiazol-5-yl]-ethyl}-phenoxy)-propionic acid 2-(4-{2-[3-(3-Chloro-4-trifluoromethoxy-phenyl)-[1,2,4]thiadiazol-5-yl]-ethyl}-2-methyl-phenoxy)-2-methyl-propionic acid 2-(4-{2-[3-(3-Chloro-4-trifluoromethoxy-phenyl)-[1,2,4]thiadiazol-5-yl]-ethoxy}-2-methyl-phenoxy)-2-methyl-propionic acid 2-(4-{2-[3-(3,4-Dichloro-phenyl)-[1,2,4]thiadiazol-5-yl]-ethoxy}-2-methyl-phenoxy)-2-methyl-propionic acid 2-Methyl-2-(2-methyl-4-{2-[3-(4-trifluoromethoxy-phenyl)-[1,2,4]thiadiazol-5-yl]-ethoxy}-phenylsulfanyl)-propionic acid 2-(4-{2-[3-(3-Chloro-4-trifluoromethoxy-phenyl)-[1,2,4]thiadiazol-5-yl]-ethoxy}-2-methyl-phenylsulfanyl)-2-methyl-propionic acid 2-(4-{2-[3-(3,4-Dichloro-phenyl)-[1,2,4]thiadiazol-5-yl]-ethoxy}-2-methyl-phenylsulfanyl)-2-methyl-propionic acid 2-Methyl-2-(2-methyl-4-{2-[3-(4-trifluoromethoxy-phenyl)-[1,2,4]thiadiazol-5-yl]-ethylsulfanyl}-phenylsulfanyl)-propionic acid 2-(4-{2-[3-(3-Chloro-4-trifluoromethoxy-phenyl)-[1,2,4]thiadiazol-5-yl]-ethylsulfanyl}-2-methyl-phenylsulfanyl)-2-methyl-propionic acid 2-(4-{2-[3-(3,4-Dichloro-phenyl)-[1,2,4]thiadiazol-5-yl]-ethylsulfanyl}-2-methyl-phenylsulfanyl)-2-methyl-propionic acid The pharmaceutical compounds of the invention include a pharmaceutical composition, comprising a pharmaceutically acceptable carrier and a compound of claim 1, 20, 22, 24, 25, 26, 27 or 28 as described in the appended claims.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The invention provides the disclosed compounds and closely related, pharmaceutically acceptable forms of the disclosed compounds, such as salts, esters, amides, hydrates or solvated forms thereof; masked or protected forms; and racemic mixtures, or enantiomerically or optically pure forms.

Pharmaceutically acceptable salts, esters, and amides include carboxylate salts (e.g., $C_{1-8}$ alkyl, cycloalkyl, aryl, heteroaryl, or non-aromatic heterocyclic) amino acid addition salts, esters, and amides which are within a reasonable benefit/risk ratio, pharmacologically effective and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See example, S. M. Berge, et al., "Pharmaceutical Salts," J. Pharm. Sci., 1977, 66:1–19, which is incorporated herein by reference. Representative pharmaceutically acceptable amides of the invention include those derived from ammonia, primary $C_{1-6}$ alkyl amines and secondary di ($C_{1-6}$ alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$ alkyl primary amines, and di ($C_{1-2}$ alkyl)amines. Representative pharmaceutically acceptable esters of the invention include $C_{1-7}$ alkyl, $C_{5-7}$ cycloalkyl, phenyl, and phenyl($C_{1-6}$)alkyl esters. Preferred esters include methyl esters.

The invention also includes disclosed compounds having one or more functional groups (e.g., amino, or carboxyl) masked by a protecting group. Some of these masked or protected compounds are pharmaceutically acceptable; others will be useful as intermediates. Synthetic intermediates and processes disclosed herein, and minor modifications thereof, are also within the scope of the invention.

Hydroxyl Protecting Groups

Protection for the hydroxyl group includes methyl ethers, substituted ethyl ethers, substituted ethyl ethers, substitute benzyl ethers, and silyl ethers.

Substituted Methyl Ethers

Examples of substituted methyl ethers include methyoxymethyl, ethylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl and 2,3, 3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(Imidazol-1-ylmethyl)bis(4", 4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate (levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate)

Carbonates

Examples of carbonates include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethyl)ethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate(tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate Sulfonates Examples of sulfonates include sulfate, methanesulfonate (mesylate), benzylsulfonate, and tosylate.

Amino Protecting Groups

Protection for the amino group includes carbamates, amides, and special —NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage

Examples of assisted cleavage include 2-methylthioethyl, 2-methylsulfonylethyl, 2-)p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include phenothiazinyl-(10)-carbonyl derivative, N'-p-toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of amides include:

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenylbenzoyl.

Assisted Cleavage

N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1,1,4,4-tetramethyldisilazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Special—NH Protective Groups

Examples of special NH protective groups include

N-Alkyl and N-Aryl Amines

N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-[(2-pyridyl)mesityl]methylene, and N-(N',N'-dimethylaminomethylene).

Protection for the Carboxyl Group

Esters

Examples of esters include formate, benzoylformate, acetate, trichloroacetate, trifluoroacetate, methoxyacetate, phenoxyacetate, p-chlorophenoxyacetate, benzoate.

Substituted Methyl Esters

Examples of substituted methyl esters include 9-fluorenylmethyl, methbxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

Examples of 2-substituted ethyl esters include 2,2,2-trichloroethyl, 2-haloethyl, ω-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto)phenyl and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl and p-P-benzyl.

Silyl Esters

Examples of silyl esters include trimethylsilyl, triethylsilyl, t-butyidimethylsilyl, i-propyldimethylsilyl, phenyidimethylsilyl and di-t-butylmethylsilyl.

Activated Esters

Examples of activated esters include thiols.

Miscellaneous Derivatives

Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group and pentaaminocobalt(III) complex.

Stannyl Esters

Examples of stannyl esters include triethylstannyl and tri-n-butylstannyl.

C. Synthesis

The invention provides methods of making the disclosed compounds according to traditional organic synthetic methods as well as matrix or combinatorial synthetic methods. Schemes A through G describe suggested synthetic routes. Using these Schemes, the guidelines below, and the examples of compounds 1–28, a person of skill in the art may develop analogous or similar methods for a given compound that are within the invention. These methods are representative of the preferred synthetic schemes, but are not to be construed as limiting the scope of the invention.

One skilled in the art will recognize that synthesis of the compounds of the present invention may be effected by purchasing an intermediate or protected intermediate compounds described in any of the schemes disclosed herein. One skilled in the art will further recognize that during any of the processes for preparation of the compounds in the present invention, it may be necessary and/or desirable to protect sensitive or reactive groups on any of the molecules concerned. This may be achieved by means of conventional protecting groups, such as those described in "Protective Groups in Organic Synthesis", John Wiley & Sons, 1991. These protecting groups may be removed at a convenient stage using methods known from the art.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation. The compounds may also be resolved by formation of diastereomeric esters or amides, followed by chromatographic separation and removal of the chiral auxiliary. Alternatively, the compounds may be resolved using a chiral HPLC column.

Examples of the described synthetic routes include Examples 1 through 38. Compounds analogous to the target compounds of these examples can be made according to similar routes. The disclosed compounds are useful in basic research and as pharmaceutical agents as described in the next section.

General Guidance

Scheme 1.
Synthesis of Intermediate 1-D

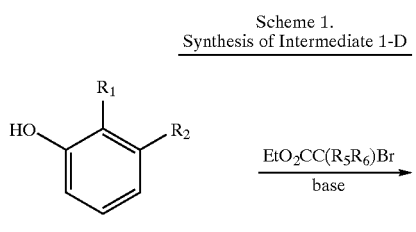

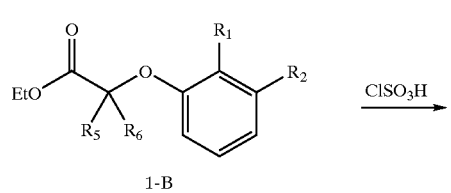

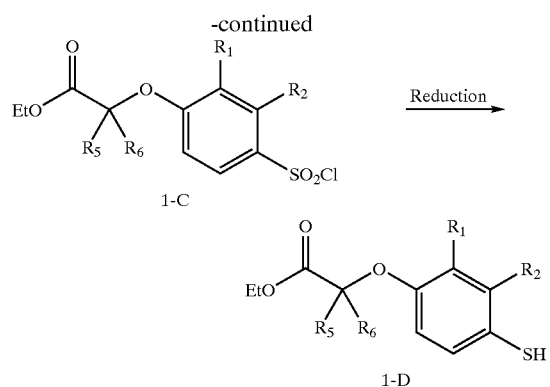

In accordance with Scheme 1, wherein $R_1$, $R_2$, $R_5$ and $R_6$ are as described above (except that $R_5$ and $R_6$ do not form spiro $C_{3-6}$ cycloalkyl or spiro 5- or 6-membered heterocyclyl), phenol 1-A, a variety of which are commercially available (such as 3-methylphenol, 2-ethylphenol, 2-propylphenol, 2,3-dimethylphenol, 2-chlorophenol, 2,3-dichlorophenol, 2-bromophenol, and 2-aminophenol), is alkylated to form phenoxyacetic acid ethyl ester 1-B with a suitable haloacetic acid ester such as bromoacetic acid ethyl ester or 2-bromo-2-methylpropionic acid ethyl ester, in the presence of an appropriate base such as $Cs_2CO_3$, $K_2CO_3$, or NaH, in a suitable solvent such as $CH_3CN$ or THF. Sulfonation of the phenoxyacetic acid ethyl ester 1-B with an appropriate sulfonating agent, such as chlorosulfonic acid, occurs selectively at the para position to provide 4-chlorosulfonylphenoxyacetic acid ethyl ester 1-C. Transformation of the sulfonylchloride 1-C to benzenethiol 1-D is accomplished using a metal as a reducing agent, such as tin or zinc, in an acidic medium such as ethanol or dioxane.

Scheme 2.
Synthesis of Compound 2-F

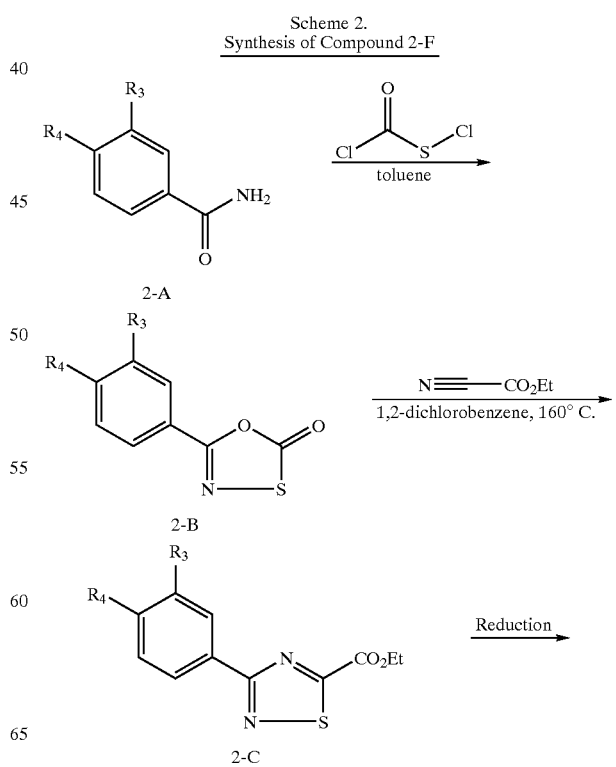

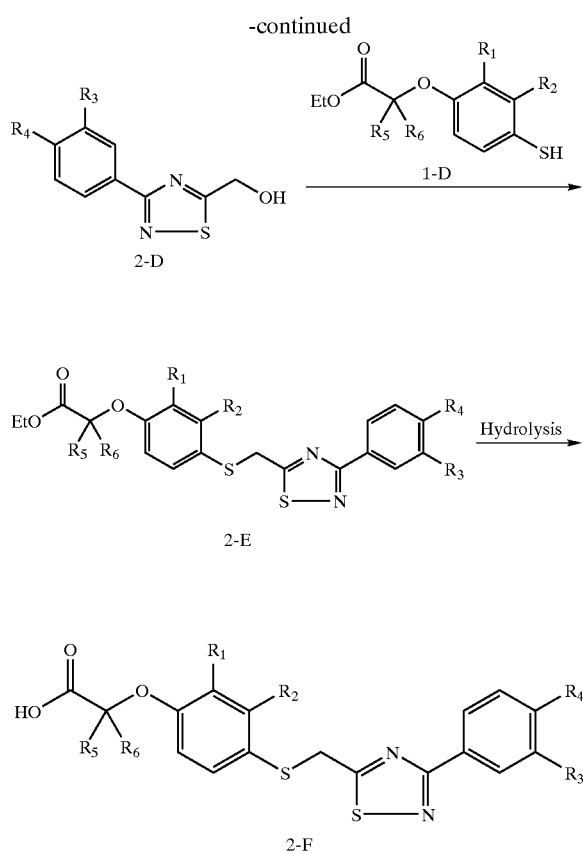

In Scheme 2, wherein $R_1$, $R_2$, $R_3$, $R_4$, $R_5$ and $R_6$ are as described above (except that $R_5$ and $R_6$ do not form spiro $C_{3-6}$ cycloalkyl or spiro 5- or 6-membered heterocyclyl), phenyl oxathiazolone 2-B is formed by reaction of benzamide 2-A, many of which are commercially available (such as $R_3$=$CF_3$, or $R_4$=$OCF_3$, $CF_3$, $OCH_3$, Cl, Br, or I, or $R_3$=$R_4$=Cl), with chlorocarbonylsulfenyl chloride in a suitable solvent such as toluene. Thermolysis of oxathiazolone 2-B and trapping of the generated benzonitrile sulfide with ethyl cyanoformate in a suitable high boiling point solvent such as chlorobenzene or 1,2-dichlorobenzene, furnishes phenyl-[1,2,4]thiadiazole-5-carboxylic acid ethyl esters 2-C. Thiadiazole ester 2-C is reduced to the corresponding alcohol 2-D using a suitable reducing agent such as sodium borohydride, lithium aluminum hydride, or diisobutylaluminium hydride. Phenoxyacetic acid ethyl ester 2-E could be obtained in two steps: (1) conversion of the alcohol 2-D to a mesylate under standard conditions by employing methanesulfonyl chloride and triethyl amine in an appropriate solvent such as $CH_2Cl_2$, or conversion of the alcohol 2-D to a bromide or chloride in the presence of triphenylphosphine and carbon tetrabromide or carbon tetrachloride, (2) alkylation of benzenethiol 1-D, prepared according to Scheme 1 above, with the mesylate, bromide, or chloride intermediate using a suitable base such as $Cs_2CO_3$, $K_2CO_3$, or NaH, in an appropriate solvent such as $CH_3CN$, DMF or THF, under nitrogen. Alternatively, synthesis of phenoxyacetic acid ethyl esters 2-E may be accomplished in one step under standard Mitsunobu conditions. Preferred conditions include using a triarylphosphine such as triphenylphosphine and an azodicarbonyl reagent such as diethyl azodicarboxylate, in a suitable solvent such as THF. Under standard saponification conditions phenoxyacetic acid ethyl ester 2-E is converted to acid 2-F under nitrogen. The preferred hydrolysis conditions include using NaOH as a base in an aqueous alcoholic solvent system such as water-methanol, or using LiOH as a base in a water-THF milder system.

Scheme 3.
Synthesis of Compound 2-F

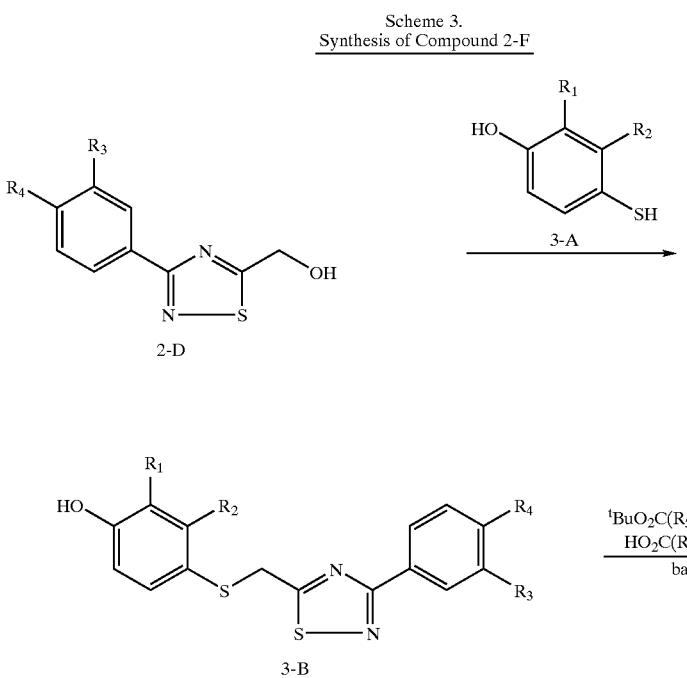

-continued

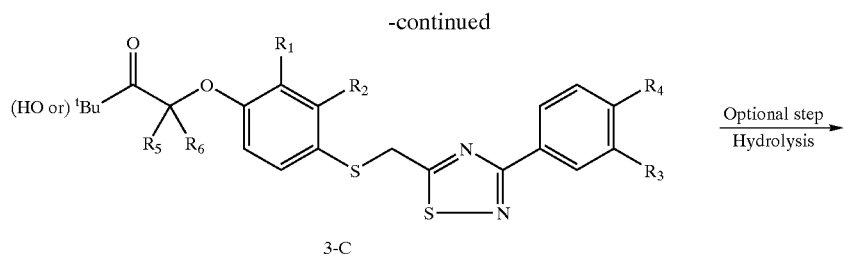

3-C

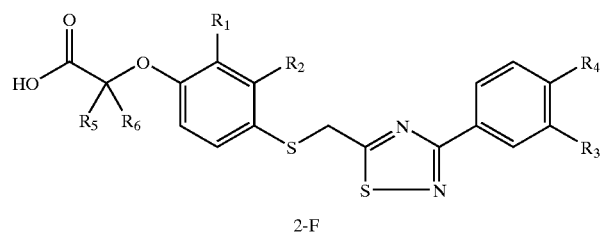

2-F

Alternatively, synthesis of [1,2,4]thiadiazole phenoxyacetic acid 2-F may be carried out as shown in Scheme 3, wherein $R_1$, $R_2$, $R_3$, $R_4$, $R_5$ and $R_6$ are as described above (except that $R_5$ and $R_6$ do not form spiro $C_{3-6}$ cycloalkyl or spiro 5- or 6-membered heterocyclyl), by installing the substituted acetic acid side chain in a later step of the synthesis. Compound 3-B may be obtained in two steps: (1) conversion of the alcohol 2-D to mesylate under standard conditions by employing methanesulfonyl chloride and triethyl amine in an appropriate solvent such as $CH_2Cl_2$, (2) selectively alkylation of 4-mercaptophenol 3-A with the mesylate intermediate using a suitable base such as $Cs_2CO_3$, $K_2CO_3$, or NaH, in an appropriate solvent such as $CH_3CN$ or THF, under nitrogen. Alternatively, synthesis of compound 3-B may be accomplished in one step under standard Mitsunobu conditions. Preferred conditions include using a triarylphosphine such as triphenylphosphine, and an azodicarbonyl reagent such as diethyl azodicarboxylate, in a suitable solvent such as THF. In the presence of an appropriate base such as $Cs_2CO_3$ or NaH, the substituted acetic acid side chain is installed by alkylation of the phenol group in 3-B using a suitable substituted holoacetic acid such as 2-bromoisobutyric acid or holoacetic acid ester such as tert-butyl 2-bromoisobutyrate to give 3-C. When the side chain in 3-C is an acetic acid ester, the carboxylic acid group could be released by using conventional reactions well known in arts. For example, tert-butyl acetate derivative 3-C is converted to acid 2-F by employing a suitable strong acid such as trifluoroacetic acid, in an appropriate solvent such as dichloromethane.

Scheme 4.
Synthesis of Intermediate 4-F

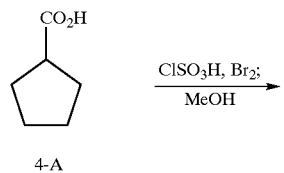

4-A

-continued

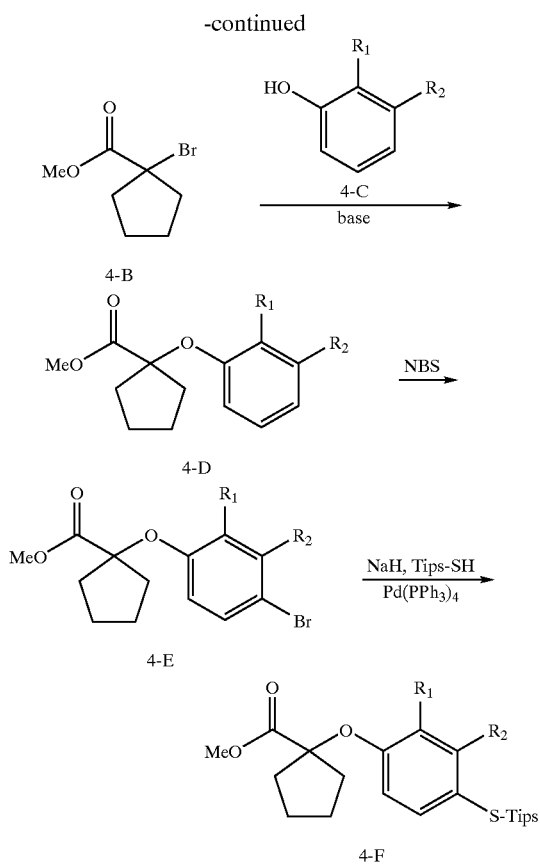

In accordance with Scheme 4, wherein $R_1$ and $R_2$ are as described above in Formula (I), 1-bromocyclopentanecarboxylic acid methyl ester 4-B is prepared by bromination of cyclopentanecarboxylic acid 4-A with bromine in the presence of a strong acid such as chlorosulfonic acid followed by methylation in refluxing methanol. Alkylation of phenol 4-C with 1-bromocyclopentanecarboxylic acid methyl ester 4-B by using a suitable base such as $Cs_2CO_3$ provides 1-phenoxycyclopentanecarboxylic acid methyl ester 4-D. Aromatic bromination of 4-D with N-bromosuccinimide in an appropriate solvent such as $CH_3CN$ occurs to give bromide 4-E. Triisopropylsilanylsulfide 4-F is obtained by reaction of bromide 4-E with triisopropylsilanethiol in the presence of a suitable base such as NaH and a palladium catalyst such as tetrakis(triphenylphosphine)palladium.

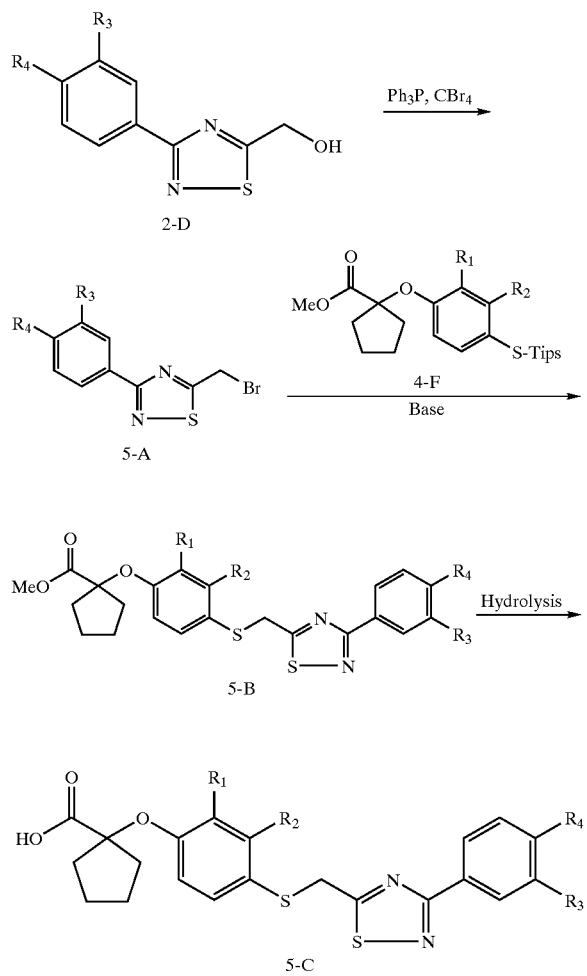

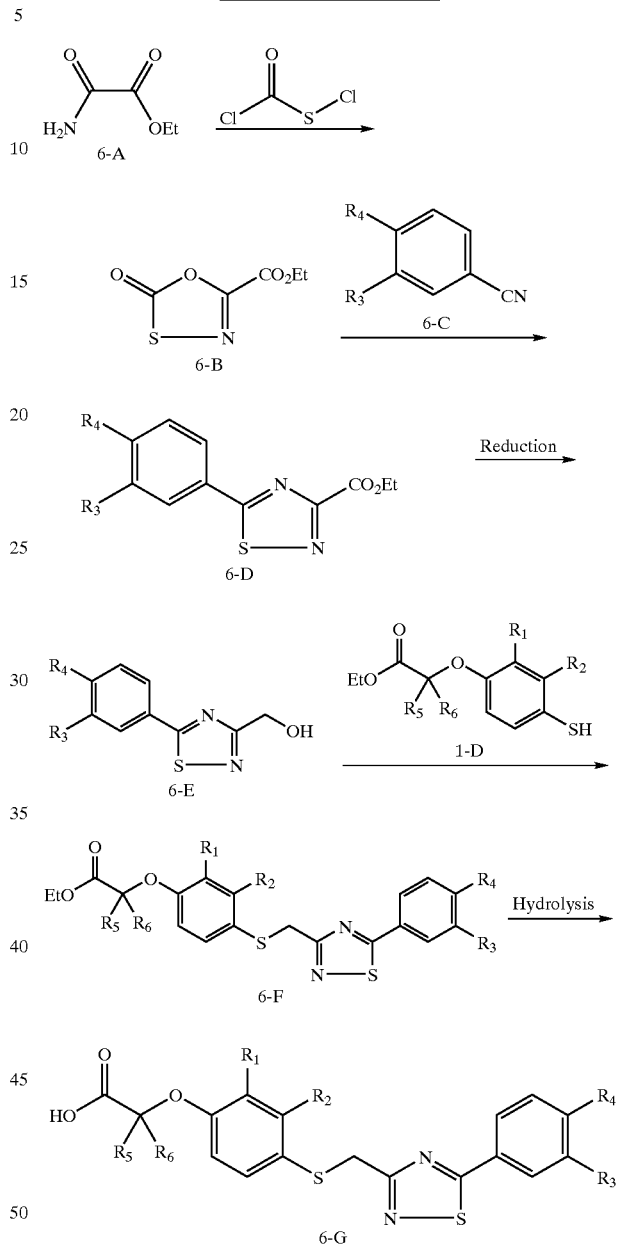

In Scheme 5, wherein $R_1$, $R_2$, $R_3$, and $R_4$ are as described above in Formula (I), alcohol 2-D is converted to bromide 5-A in the presence of triphenylphosphine and carbon tetrabromide. Phenoxycyclopentanecarboxylic acid methyl ester 5-B is obtained by reaction of the bromide 5-A with triisopropylsilanylsulfide 4-F, prepared according to Scheme 4 above, using a suitable base such as $Cs_2CO_3$ or tetrabutylammonium fluoride, in an appropriate solvent such as $CH_3CN$, DMF or THF. Under standard saponification conditions methyl ester 5-B is converted to carboxylic acid 5-C under nitrogen. The preferred hydrolysis conditions include using NaOH as a base in an aqueous alcoholic solvent system such as water-methanol, or using LiOH as a base in a water-THF milder system.

In accordance with Scheme 6, wherein $R_1$, $R_2$, $R_3$, $R_4$, $R_5$ and $R_6$ are as described above in Formula (I), oxathiazolone 6-B is formed by reaction of ethyl oxamate 6-A with chlorocarbonylsulfenyl chloride in a suitable solvent such as toluene. Thermolysis of oxathiazolone 6-B and trapping of the generated nitrile sulfide with benzonitrile 6-C in a suitable high boiling point solvent such as chlorobenzene or 1,2-dichlorobenzene furnishes phenyl-[1,2,4]thiadiazoie-3-carboxylic acid ethyl ester 6-D. Thiadiazole carboxylic ester 6-D is reduced to the corresponding alcohol 6-E using a suitable reducing agent such as sodium borohydride, lithium aluminum hydride, or diisobutylaluminium hydride. Phenoxyacetic acid ethyl ester 6-F can be prepared in two steps:

(1) conversion of the alcohol 6-E to a bromide or chloride in the presence of triphenylphosphine and carbon tetrabromide or carbon tetrachloride, (2) alkylation of benzenethiol 1-D, prepared according to Scheme 1 above, with the bromide or chloride intermediate using a suitable base such as $Cs_2CO_3$, $K_2CO_3$, or NaH, in an appropriate solvent such as $CH_3CN$, DMF or THF, under nitrogen. Under standard saponification conditions phenoxyacetic acid ethyl ester 6-F is converted to carboxylic acid 6-G. The preferred hydrolysis conditions include using NaOH as a base in an aqueous alcoholic solvent system such as water-methanol-THF, or using LiOH as a base in a water-THF milder system.

provides 7-C, which upon oxidation with mCPBA gives 7-D. 7-D is hydrolyzed to give 7-E. Treating with compounds like D39, D44 and D34 leads to 7-F and further hydrolysis gives compounds of 7-G.

EXAMPLES

Example 1

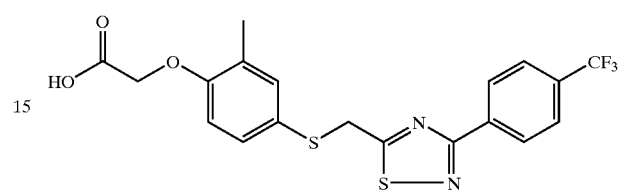

{2-Methyl-4-[3-(4-trifluoromethyl-phenyl)-[1,2,4]thiadiazol-5-ylmethylsulfanyl]-phenoxy}-acetic acid

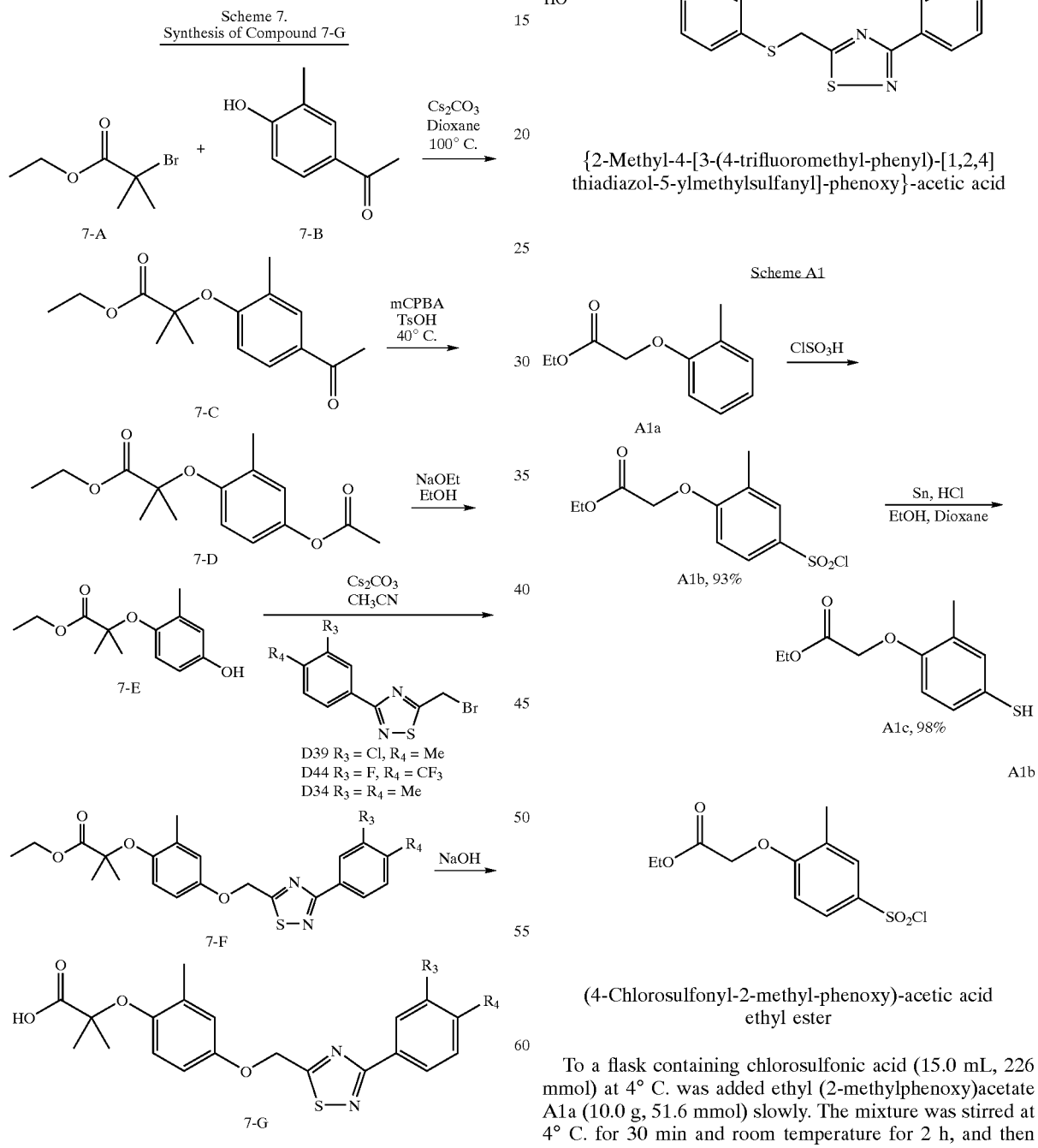

(4-Chlorosulfonyl-2-methyl-phenoxy)-acetic acid ethyl ester

To a flask containing chlorosulfonic acid (15.0 mL, 226 mmol) at 4° C. was added ethyl (2-methylphenoxy)acetate A1a (10.0 g, 51.6 mmol) slowly. The mixture was stirred at 4° C. for 30 min and room temperature for 2 h, and then poured into ice water. The precipitated white solid was filtered, washed with water, and dried under vacuum overnight to provide 14.0 g (93%) of A1b as a white solid; $^1$H In accordance with Scheme 7, wherein $R_3$ and $R_4$ are as described above in Formula (I), reaction of 7-A and 7-B NMR (300 MHz, CDCl$_3$) δ 7.87–7.84 (m, 2 H), 6.80 (d, J=9.5 Hz, 1 H), 4.76 (s, 2 H), 4.29 (q, J=7.1 Hz, 2 H), 2.37 (s, 3 H), 1.31 (t, J=7.1 Hz, 3 H); MS (ES) m/z: 315 (M+Na$^+$).

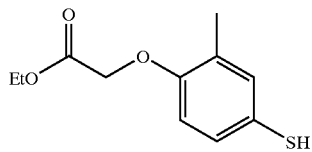

A1c (4-Mercapto-2-methyl-phenoxy)-acetic acid ethyl ester

To a solution of A1b (4.70 g, 16.1 mmol) in EtOH (20 mL) was added 4.0 M HCl in dioxane (20 mL) followed by 100 mesh tin powder (9.80 g, 82.6 mmol) portionwise. The mixture was refluxed for 2 h, poured into CH$_2$Cl$_2$/ice (100 mL), and filtered. The filtrate was separated, and the aqueous layer was extracted with CH$_2$Cl$_2$. The combined organic phases were washed with water, dried, and concentrated to give 3.56 g (98%) of A1c as a yellow oil; $^1$H NMR (300 MHz, CDCl$_3$) δ 7.14–7.03 (m, 2 H), 6.59 (d, J=8.4 Hz, 1 H), 4.60 (s, 2 H), 4.25 (q, J=7.1 Hz, 2 H), 2.24 (s, 3 H), 1.29 (t, J=7.1 Hz, 3 H).

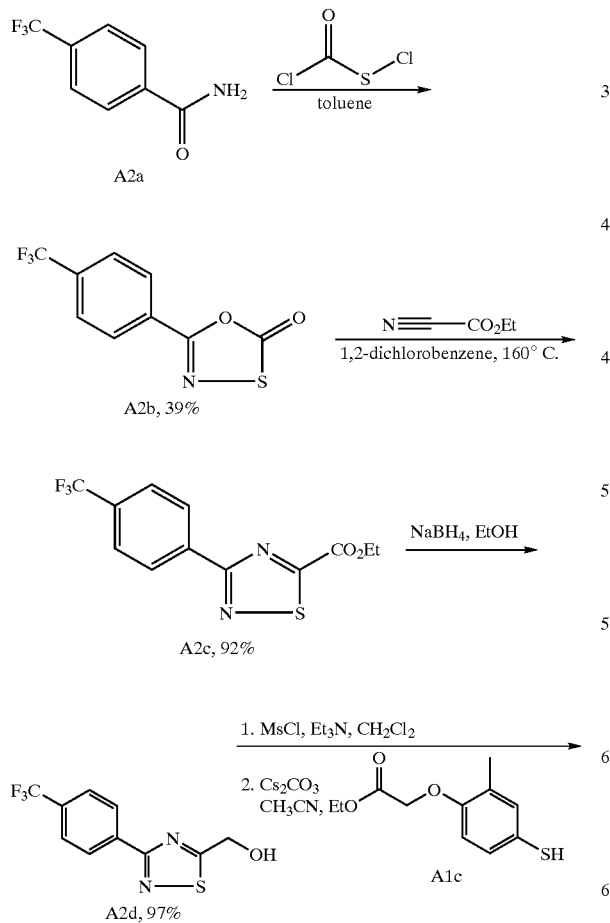

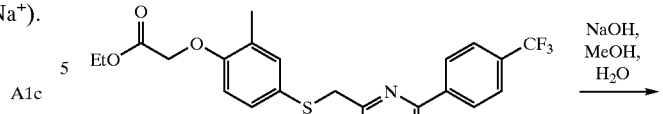

A2e, 64%

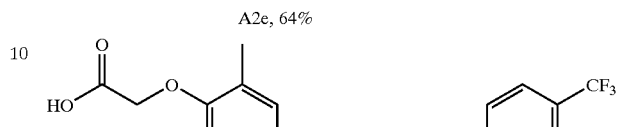

100%

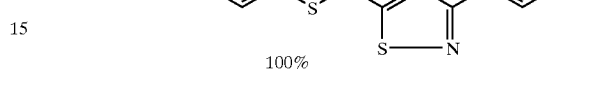

A2B

5(4-Trifluromethyl-phenyl)-[1,3,4]oxathiazol-2-one

The reaction mixture of 4-trifluoromethylbenzamide A2a (2.57 g, 13.6 mmol), chlorocarbonylsulfenyl chloride (3.57 g, 27.2 mmol) in toluene (35 mL) was heated at 60° C. for 15 h and concentrated. CH$_2$Cl$_2$ was added and the mixture was filtered. The white solid was washed with CH$_2$Cl$_2$ and dried under high vacuum to give 922 mg (36%) of 4-trifluoromethylbenzamide A2a as recovered starting material. The filtrate was concentrated and column chromatographed (EtOAc/hexane) to provide 1.31 g (39%) of A2b as white crystals; $^1$H NMR (300 MHz, CDCl$_3$) δ 8.11 (d, J=8.2 Hz, 2 H), 7.77 (d, J=8.3 Hz, 2 H).

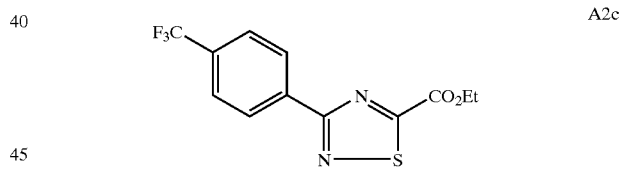

3-(4-Trifluoromethyl-phenyl)-[1,2,4]thiadiazole-5-carboxylic acid ethyl ester

A reaction mixture of A2b (448 mg, 1.81 mmol) and ethyl cyanoformate (722 mg, 7.29 mmol) in 1,2-dichlorobenzene (7 mL) was heated at 160° C. for 20 h. After cooling down to room temperature, the reaction mixture was purified by column chromatography to give 505 mg (92%) of A2c as a yellow solid; $^1$H NMR (300 MHz, CDCl$_3$) δ 8.50 (d, J=8.1 Hz, 2 H), 7.76 (d, J=8.2 Hz, 2 H), 4.57 (q, J=7.1 Hz, 2 H), 1.49 (t, J=7.1 Hz, 3 H); MS (ES) m/z: 303 (M+H$^+$).

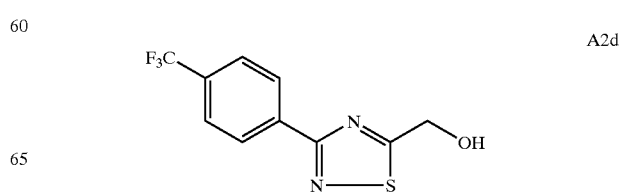

[3-(4-Trifluoromethyl-phenyl)-[1,2,4]thiadiazol-5-yl]-methanol

To a solution of A2c (200 mg, 0.662 mmol) in EtOH (10 mL) at room temperature was added NaBH$_4$ (64 mg, 1.7 mmol). After stirring for 2 h, a few drops of water were added to quench excess of hydride. EtOH was evaporated, and the residue was partitioned between CH$_2$Cl$_2$ and water. The organic phase was dried and concentrated to provide 167 mg (97%) of A2d as off-white crystals; $^1$H NMR (300 MHz, CDCl$_3$) δ 8.40 (d, J=8.1 Hz, 2 H), 7.74 (d, J=8.2 Hz, 2 H), 5.20 (s, 2 H), 2.65 (brs, 1 H); MS (ES) m/z: 261 (M+H$^+$).

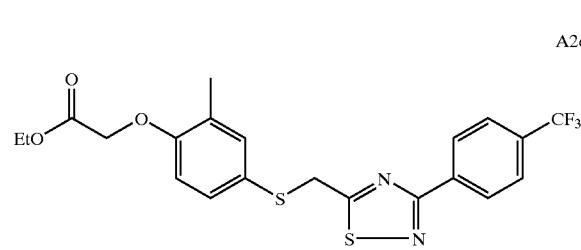

A2e

{2-Methyl-4-[3-(4-trifluoromethyl-phenyl)-[1,2,4]thiadiazol-5-ylmethylsulfanyl]-phenoxy}-acetic acid ethyl ester A mixture of A2d (88 mg, 0.34 mmol), methanesulfonyl chloride (58 mg, 0.51 mmol), and triethylamine (70 mg, 0.69 mmol) in CH$_2$Cl$_2$ (3 mL) was stirred at room temperature for 1.5 h. The mixture was washed with water and the aqueous phase was back extracted with CH$_2$Cl$_2$. The combined organic layers were dried and concentrated to provide 111 mg of the mesylate as a yellow solid.

A mixture of the crude mesylate (111 mg) and (4-mercapto-2-methyl-phenoxy)acetic acid ethyl ester A1c (111 mg, 0.491 mmol) in CH$_3$CN (4 mL) was degassed under N$_2$ for about 15 min. After the addition of Cs$_2$CO$_3$ (214 mg, 0.656 mmol), the mixture was stirred overnight under N$_2$, concentrated, and purified by column chromatography (EtOAc/hexane) to give 102 mg (64%, 3 steps) of A2e as a white solid; $^1$H NMR (300 MHz, CDCl$_3$) δ 8.35 (d, J=8.1 Hz, 2 H), 7.71 (d, J=8.2 Hz, 2 H), 7.30 (d, J=1.7 Hz, 1 H), 7.23 (dd, J=8.6, 2.2 Hz, 1 H), 6.62 (d, J=8.5 Hz, 1 H), 4.61 (s, 2 H), 4.41 (s, 2 H), 4.24 (q, J=7.1 Hz, 2 H), 2.25 (s, 3 H), 1.27 (t, J=7.1 Hz, 3 H); MS (ES) m/z: 491 (M+Na$^+$).

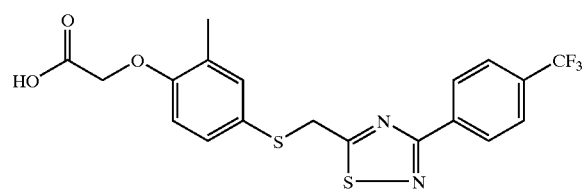

{2-Methyl-4-[3-(4-trifluoromethyl-phenyl)-[1,2,4]thiadiazol-5-ylmethylsulfanyl]-phenoxy}-acetic acid A mixture of A2e (77 mg, 0.16 mmol) and 2 M NaOH (0.30 mL, 0.60 mmol) in MeOH (4 mL) was stirred under N$_2$ for 30 min and concentrated. EtOAc and water were added, and the mixture was acidified with concentrated HCl. The organic phase was separated and the aqueous phase was extracted with EtOAc. The combined organic layers were dried and concentrated to give 70 mg (97%) of the target compound, Compound 1, as an off-white solid; $^1$H NMR (300 MHz, MeOH-d$_4$) δ 8.37 (d, J=8.1 Hz, 2 H), 7.78 (d, =8.3 Hz, 2 H), 7.28 (s, 1 H), 7.26 (m, 1 H), 6.76 (d, J=8.3 Hz, 1 H), 4.66 (s, 2 H), 4.53 (s, 2 H), 2.20 (s, 3 H); MS (ES) m/z: 441 (M+H$^+$); FAB-HRMS (M$^+$). Calcd 440.0476, found 440.0465.

Example 2

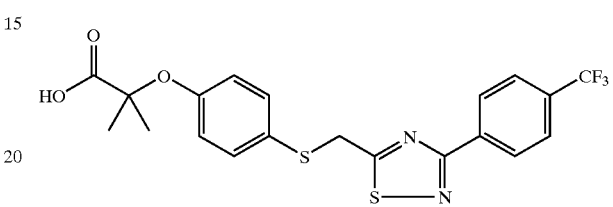

2-Methyl-2-{4-[3-(4-trifluoromethyl-phenyl)-[1,2,4]thiadiazol-5-ylmethylsulfanyl]-phenoxy}-propionic acid Scheme B

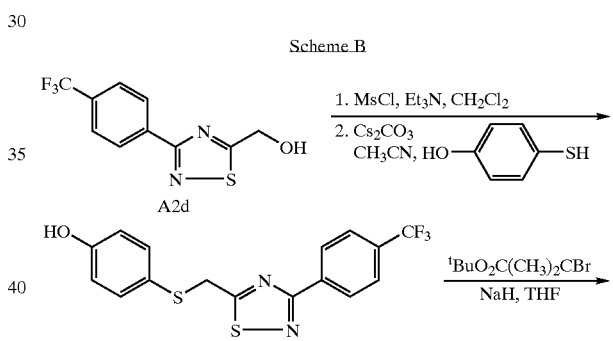

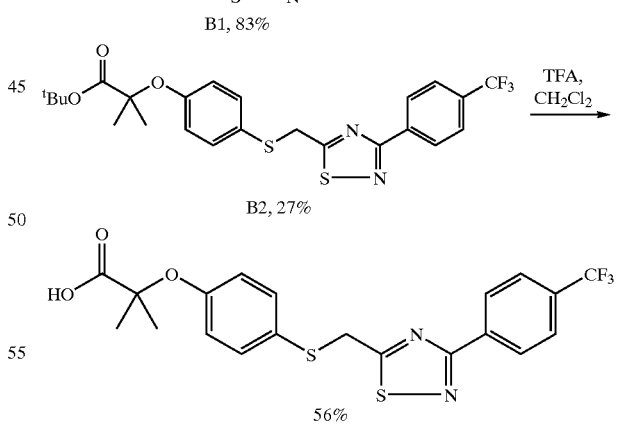

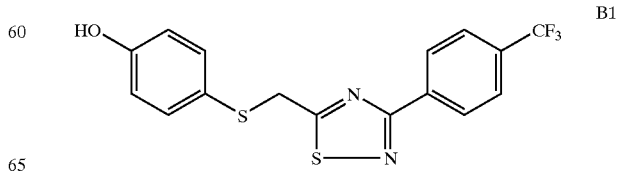

4-[3-(4-Trifluoromethyl-phenyl)-[1,2,4]thiadiazol-5-ylmethylsulfanyl]phenol

To a solution of A2d (795 mg, 3.06 mmol) in CH$_2$Cl$_2$ (30 mL) at 0° C. were added methanesulfonyl chloride (518 mg, 4.52 mmol) and triethylamine (617 mg, 6.11 mmol). The mixture was stirred at room temperature for 1 h and then partitioned between water and CH$_2$Cl$_2$ (80 mL). The organic layer was washed with brine, dried, concentrated, and column chromatographed (EtOAc/hexane) to provide 859 mg (83%) of the mesylate as a white solid.

A mixture of the mesylate (210 mg, 0.621 mmol) and 4-mercaptophenol (113 mg, 0.897 mmol) in CH$_3$CN (8 mL) was degassed under N$_2$ for about 10 min. After the addition of Cs$_2$CO$_3$ (242 mg, 0.742 mmol), the mixture was stirred at room temperature for 40 min, concentrated, and purified by column chromatography (EtOAc/hexane) to give 228 mg (100%) of B1 as a white crystalline solid; $^1$H NMR (300 MHz, CDCl$_3$) δ 8.35 (d, J=8.1 Hz, 2 H), 7.71 (d, J=8.3 Hz, 2 H), 7.36 (d, J=8.7 Hz, 2 H), 6.78 (d, J=8.7 Hz, 2 H), 4.97 (s, 1H), 4.40 (s, 2 H); MS (ES) m/z: 369 (M+H$^+$).

B2

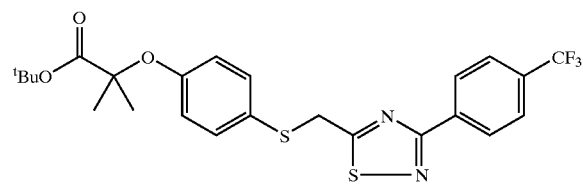

2-Methyl-2-{4-[3-(4-trifluoromethyl-phenyl)-[1,2,4]thiadiazol-5-ylmethylsulfanyl]-phenoxy}-propionic acid tert-butyl ester To a three-necked flask containing NaH (36 mg, 0.90 mmol; 60% in mineral oil) was added a solution of B1 (220 mg, 0.598 mmol) in THF. To the mixture at 40° C. was added tert-butyl 2-bromoisobutyrate (287 mg, 1.29 mmol). After heating at 70° C. for 2 h, more tert-butyl 2-bromoisobutyrate (215 mg, 0.970 mmol) was added and the heating was continued overnight. The mixture was quenched with water (0.1 mL), concentrated, and chromatographed (EtOAc/hexane) to give 81 mg (27%) of B2; $^1$H NMR (300 MHz, CDCl$_3$) δ 8.35 (d, J=8.2 Hz, 2 H), 7.71 (d, J=8.2 Hz, 2 H), 7.34 (d, J=8.8 Hz, 2 H), 6.78 (d, J=8.7 Hz, 2 H), 4.42 (s, 2 H), 1.55 (s, 6 H), 1.38 (s, 9 H); MS (ES) m/z: 511 (M+H$^+$).

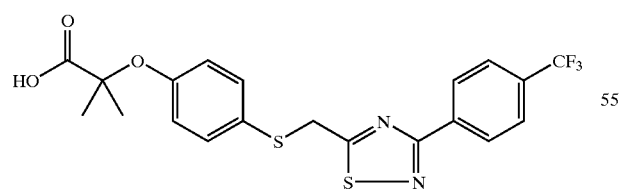

2-Methyl-2-{4-[3-(4-trifluoromethyl-phenyl)-[1,2,4]thiadiazol-5-ylmethylsulfanyl]-phenoxy}-propionic acid The mixture of B2 (80 mg, 0.16 mmol) in CH$_2$Cl$_2$ (1.5 mL) and trifluoroacetic acid (0.5 mL) was stirred at room temperature for 1.5 h, concentrated, and column chromatographed twice (EtOAc/hexane, CH$_2$Cl$_2$/MeOH) to give 40 mg (56%) of the target compound, Compound 2, as a light yellow solid; $^1$H NMR (300 MHz, CDCl$_3$) δ 8.34 (d, J=8.0 Hz, 2 H), 7.71 (d, J=8.2 Hz, 2 H), 7.37 (d, J=8.8 Hz, 2 H), 6.87 (d, J=8.8 Hz, 2 H), 4.45 (s, 2 H), 1.59 (s, 6 H); MS (ES) m/z: 453 (M−H$^+$).

Example 3

2-Methyl-2-{2-methyl-4-[3-(4-trifluoromethyl-phenyl)-[1,2,4]thiadiazol-5-ylmethylsulfanyl]-phenoxy}-propionic acid

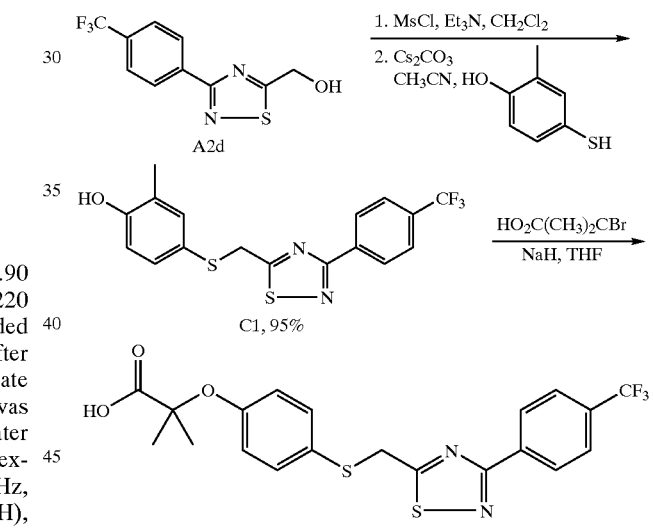

2-Methyl-4-[3-(4-trifluoromethyl-phenyl)-[1,2,4]thiadiazol-5-ylmethylsulfanyl]-phenol Replacing 4-mercaptophenol with 4-mercapto-2-methylphenol and following the same procedure as in the preparation of B1 gave C1 (95%, white crystalline solid); $^1$H NMR (300 MHz, CDCl$_3$) δ 8.35 (d, J=8.0 Hz, 2 H), 7.71 (d, J=8.2 Hz, 2 H), 7.26 (s, 1 H), 7.20 (dd, J=8.0, 2.1 Hz, 1 H), 6.71 (d, J=8.2 Hz, 1 H), 4.83 (s,1 H), 4.40 (s, 2 H), 2.21 (s, 3 H); MS (ES) m/z: 383 (M+H⁺).

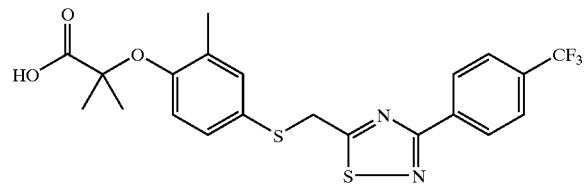

2-Methyl-2-{2-methyl-4-[3-(4-trifluoromethyl-phenyl)-[1,2,4]thiadiazol-5-ylmethylsulfanyl]-phenoxy}-propionic acid To a solution of C1 (39 mg, 0.10 mmol) in THF (1 mL) was added NaH (20 mg, 0.50 mmol; 60% in mineral oil) and the mixture was heated at 60° C. for 30 min, during which the solution changed to blue then brown color. 2-Bromoisobutyric. acid (34 mg, 0.20 mmol) was added, and the mixture was heated at the same temperature for 1 h, acidified with 1 N HCl, and diluted with CH₂Cl₂. The organic phase was separated, washed with brine, dried, concentrated, and column chromatographed (EtOAc/hexane) to isolate 10 mg (21%) of the target compound, Compound 3, as a yellow oil; ¹H NMR (300 MHz, CDCl₃) δ 8.35 (d, J=8.0 Hz, 2 H), 7.71 (d, J=8.2 Hz, 2 H), 7.28 (m, 1 H), 7.18 (dd, J=8.4, 2.4 Hz, 1 H), 6.72 (d, J=8.5 Hz, 1 H), 4.43 (s, 2 H), 2.20 (s, 3 H), 1.61 (s, 6 H); MS (ES) m/z: 469 (M+H⁺). Anal. Calcd. For C₂₁H₁₉F₃N₂O₃S₂.0.30 H₂O: C, 53.22; H, 4.17; N, 5.91. Found: C, 53.36; H, 3.88; N, 5.62.

Example 4

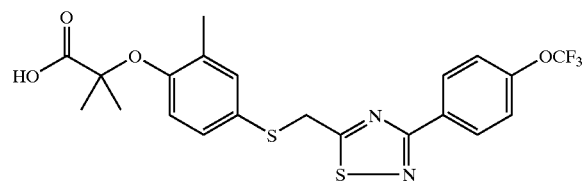

2-Methyl-2-{2-methyl-4-[3-(4-trifluoromethoxyphenyl)-[1,2,4]thiadiazol-5-ylmethylsulfanyl]-phenoxy}-propionic acid Scheme D1

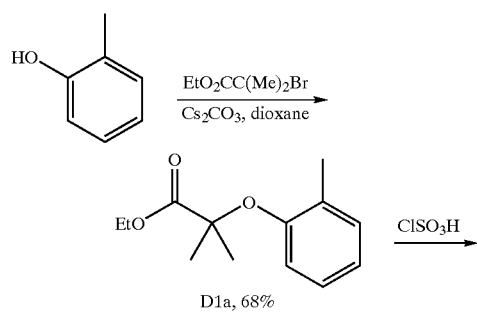

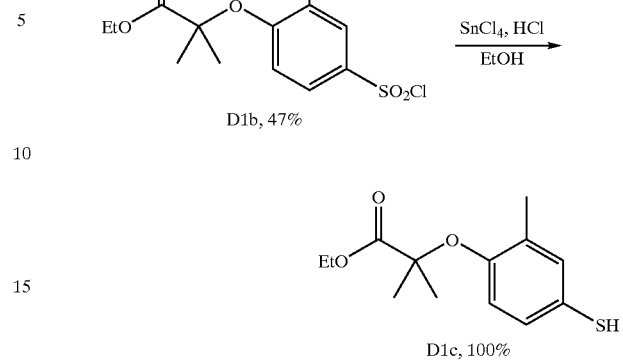

2-Methyl-2-o-tolyloxy-propionic acid ethyl ester

To a mixture of 2-bromo-2-methylpropionic acid ethyl ester (8.27 mL, 64.0 mmol) and 2-methylphenol (7.60 g, 70.2 mmol) in dioxane (100 mL) was added Cs₂CO₃ (31.3 g, 96.0 mmol). After the mixture was refluxed at 100° C. for 4 hours and allowed to cool down to room temperature, the solvent was evaporated under reduced pressure. The residue was dissolved in Et₂O, washed with 1 N NaOH, dried, and concentrated to give 9.69 g (68%) of D1a; ¹H NMR (300 MHz, CDCl₃) δ 7.13 (d, J=7.3 Hz, 1 H), 7.03 (t, J=7.6 Hz, 1 H), 6.87 (t, J=7.3 Hz, 1 H), 6.66 (d, J=8.2 Hz, 1 H), 4.24 (q, J=7.1 Hz, 2 H), 2.23 (s, 3 H), 1.59 (s, 6 H), 1.25 (t, J=7.1 Hz).

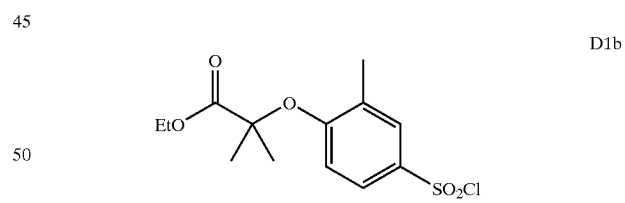

2-(4-Chlorosulfonyl-2-methyl-phenoxy)-2-methyl-propionic acid ethyl ester

To a flask containing D1a (11.3 g, 0.0510 mol) at 0° C. was slowly added ClSO₃H (15.2 mL, 0.229 mol). The temperature was allowed to warm to room temperature and the solution was stirred for 1 hour. Upon stirring, the reaction mixture was poured into ice. The solid was filtered, washed with water, and vacuum dried to give 7.7 g (47%) of D1b; ¹H NMR (300 MHz, CDCl₃) δ 7.82 (d, J=2.5 Hz, 1 H), 7.75 (dd, J=8.9, 2.5 Hz, 1 H), 6.67 (d, J=8.8 Hz, 1 H), 4.23 (q, J=7.1 Hz, 2 H), 2.31 (s, 3 H), 1.70 (s, 6 H), 1.22 (t, J=7.1 Hz); MS (ES) m/z: 343 (M+Na⁺).

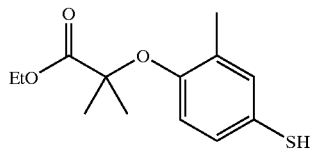

D1c

2-(4-Mercapto-2-methyl-phenoxy)-2-methyl-propionic acid ethyl ester

To a solution of D1b (2.00 g, 6.25 mmol) in EtOH (7.8 mL) were added HCl in dioxane (4.0 M, 7.8 mL, 31 mmol) and tin powder (3.70 g, 31.2 mmol). The mixture was refluxed for 3 hours, poured into ice, and extracted with $CH_2Cl_2$ (50 mL×3). The organic layers were combined and dried over $Na_2SO_4$. After filtration, the filtrate was concentrated to give 3.37 g (~100%) of D1c; $^1$H NMR (300 MHz, $CDCl_3$) δ 7.12 (d, J=2.0 Hz, 1 H), 7.00 (dd, J=8.4, 2.4 Hz, 1 H), 6.56 (d, J=8.4 Hz, 1 H), 4.23 (q, J=7.1 Hz, 2 H), 3.31 (s, 1 H), 2.18 (s, 3 H), 1.57 (s, 6 H), 1.25 (t, J=7.1 Hz); MS (ES) m/z: 255 (M+H$^+$).

Scheme D2

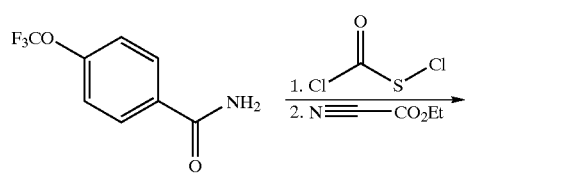

D2a

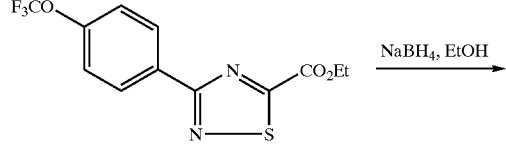

D2b, 83%

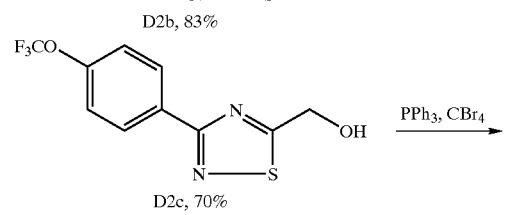

D2c, 70%

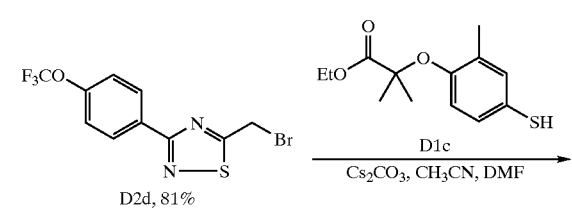

D2d, 81%

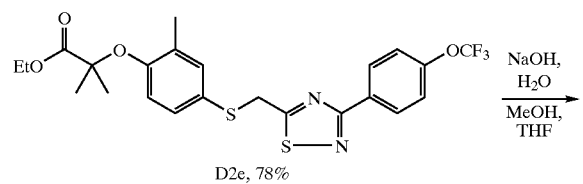

D2e, 78%

-continued

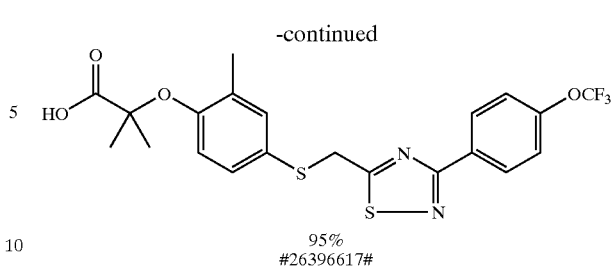

95%
26396617#

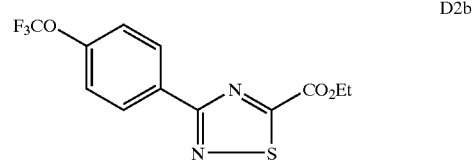

D2b

3-(4-Trifluoromethoxy-phenyl)-[1,2,4]thiadiazole-5-carboxylic acid ethyl ester Following the same procedure as in the preparation of A2c gave D2b (white solid, 97%); $^1$H NMR (300 MHz, $CDCl_3$) δ 8.42 (m, 2 H), 7.33 (dd, J=8.9, 0.8 Hz, 2 H), 4.56 (q, J=7.1 Hz, 2 H), 1.49 (t, J=7.1 Hz, 3 H).

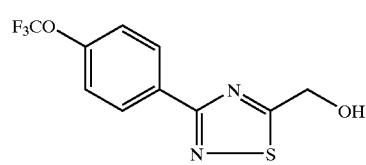

D2c

[3-(4-Trifluoromethoxy-phenyl)-[1,2,4]thiadiazol-5-yl]-methanol

Following the same procedure as in the preparation of A2d gave D2c (white solid, 70%); $^1$H NMR (300 MHz, $CDCl_3$) δ 8.32 (m, 2 H), 7.31 (d, J=8.1 Hz, 2 H), 5.17 (d, J=5.8 Hz, 2 H), 1.26 (t, J=7.1 Hz, 1 H); MS (ES) m/z: 277 (M+H$^+$).

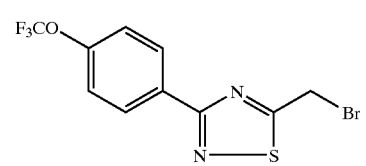

D2d

5-Bromomethyl-3-(4-trifluoromethoxy-phenyl)-[1,2,4]thiadiazole

To a solution of D2c (679 mg, 2.46 mmol) in $CH_2Cl_2$ (10 mL) were added carbon tetrabromide (896 mg, 2.70 mmol) and triphenylphosphine (707 mg, 2.70 mmol). The mixture was stirred at 0° C. for 1 h and room temperature for 1 h, concentrated, and purified by column chromatography to give 678 mg (81%) of D2d as a white solid; $^1$H NMR (300 MHz, CDCl$_3$) δ 8.32 (m, 2 H), 7.31 (dd, J=8.9, 0.8 Hz, 2 H), 4.82 (s, 2 H); MS (ES) m/z: 339 (M+H$^+$).

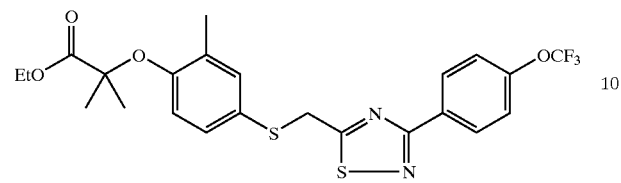

D2e

2-Methyl-2-{2-methyl-4-[3-(4-trifluoromethoxy-phenyl)-[1,2,4]thiadiazol-5-ylmethylsulfanyl]-phenoxy}-propionic acid ethyl ester To a mixture of D2d (73 mg, 0.22 mmol) and 2-(4-mercapto-2-methyl-phenoxy)-2-methyl-propionic acid ethyl ester D1c (52 mg, 0.21 mmol) in CH$_3$CN (1.5 mL) and DMF (0.1 mL) was added Cs$_2$CO$_3$ (100 mg, 0.31 mmol). After stirring at room temperature for 15 min, the mixture was concentrated. The residue was diluted with EtOAc, washed with water and brine, dried, concentrated, and column chromatographed to give 82 mg (78%) of D2e; $^1$H NMR (300 MHz, CDCl$_3$) δ 8.27 (d, J=8.9 Hz, 2 H), 7.29 (dd, J=8.9, 0.9 Hz, 1 H), 7.26 (m, 2 H), 7.13 (dd, J=8.5, 2.4 Hz, 1 H), 6.56 (d, J=8.5 Hz, 1 H), 4.40 (s, 2 H), 4.20 (q, J=7.1 Hz, 2 H), 2.18 (s, 3 H), 1.58 (s, 6 H), 1.20 (t, J=7.1 Hz, 3 H); MS (ES) m/z: 513 (M+H$^+$). Anal. Calcd. For C$_{23}$H$_{23}$F$_3$N$_2$O$_4$S$_2$: C, 53.90; H, 4.52; N, 5.47. Found: C, 54.25; H, 4.37; N, 5.40.

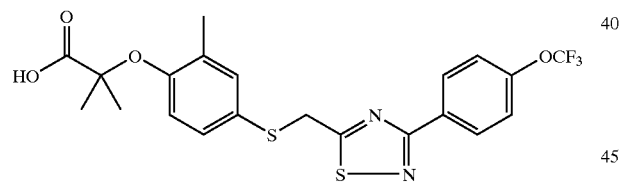

2-Methyl-2-{2-methyl-4-[3-(4-trifluoromethoxy-phenyl)-[1,2,4]thiadiazol-5-ylmethylsulfanyl]-phenoxy}-propionic acid A solution of D2e (80 mg, 0.16 mmol) in MeOH (1.0 mL) and THF (1.0 mL) was treated with 2 N NaOH (1.0 mL, 2.0 mmol) for 4 h and concentrated. The residue was diluted with EtOAc and water, and acidified with concentrated HCl. The organic layer was separated and the aqueous layer was extracted with EtOAc. The combined organic phases were washed with brine, dried, concentrated, and column chromatographed to provide 71 mg (95%) of Compound 4, $^1$H NMR (400 MHz, CDCl$_3$) δ 8.27 (d, J=8.8 Hz, 2 H), 7.30–7.23 (m, 3 H), 7.17 (d, J=8.4 Hz, 1 H), 6.72 (d, J=8.4 Hz, 1 H), 4.42 (s, 2 H), 2.20 (s, 3 H), 1.60 (s, 6 H); MS (ES) m/z: 507 (M+Na$^+$). Anal. Calcd. For C$_{21}$H$_{19}$F$_3$N$_2$O$_4$S$_2$: C, 52.06; H, 3.95; N, 5.78. Found: C, 52.38; H, 3.74; N, 5.52.

Example 5

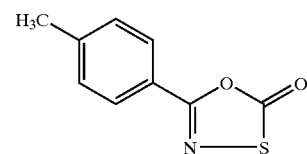

D1

5-p-Tolyl-[1,3,4]oxathiazol-2-one

Following the same procedure as in the preparation of A2b gave D1; $^1$H NMR (300 MHz, CDCl$_3$) δ 7.86 (d, J=8.0 Hz, 2 H), 7.29 (d, J=8.0 Hz, 2 H), 2.43 (s, 3 H).

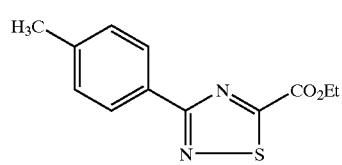

D2

3-p-Tolyl-[1,2,4]thiadiazole-5-carboxylic acid ethyl ester

Following the same procedure as in the preparation of A2c gave D2; $^1$H NMR (400 MHz, CDCl$_3$) δ 8.25 (d, J=8.2 Hz, 2 H), 7.30 (d, J=8.0 Hz, 2 H), 4.55 (q, J=7.1 Hz, 2 H), 2.42 (s, 3 H), 1.49 (t, J=7.1 Hz, 3 H).

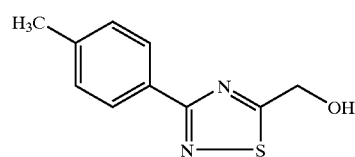

D3

(3-p-Tolyl-[1,2,4]thiadiazol-5-yl)-methanol

Following the same procedure as in the preparation of A2d gave D3; $^1$H NMR (300 MHz, CDCl$_3$) δ 8.16 (d, J=8.2 Hz, 2 H), 7.28 (d, J=8.0 Hz, 2 H), 5.16 (s, 2 H), 2.69 (brs, 1 H), 2.41 (s, 3 H); MS (ES) m/z: 207 (M+H$^+$).

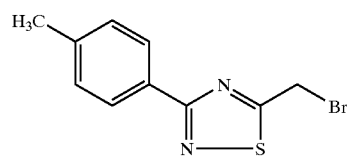

D4

5-Bromomethyl-3-p-tolyl-[1,2,4]thiadiazole

Following the same procedure as in the preparation of D2d gave D4; $^1$H NMR (300 MHz, CDCl$_3$) δ 8.16 (d, J=8.2 Hz, 2 H), 7.28 (d, J=8.1 Hz, 2 H), 4.82 (s, 2 H), 2.42 (s, 3 H); MS (ES) m/z: 271 (M+H$^+$).

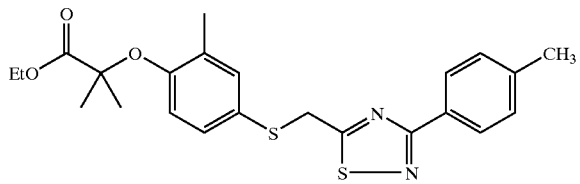

2-Methyl-2-[2-methyl-4-(3-p-tolyl-[1,2,4]thiadiazol-5-ylmethylsulfanyl)-phenoxy]-propionic acid ethyl ester Following the same procedure as in the preparation of D2e gave D5; $^1$H NMR (300 MHz, CDCl$_3$) δ 8.12 (d, J=8.2 Hz, 2 H), 7.27–7.24 (m, 3 H), 7.14 (dd, J=8.5, 2.3 Hz, 1 H), 6.56 (d, J=8.5 Hz, 1 H), 4.40 (s, 2 H), 4.19 (q, J=7.1 Hz, 2 H), 2.40 (s, 3 H), 2.18 (s, 3 H), 1.58 (s, 6 H), 1.19 (t, J=7.1 Hz, 3 H); MS (ES) m/z: 443 (M+H$^+$).

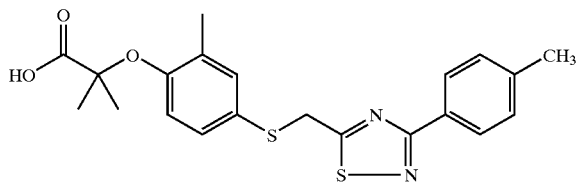

2-Methyl-2-[2-methyl-4-(3-p-tolyl-[1,2,4]thiadiazol-5-ylmethylsulfanyl)-phenoxy]-propionic acid Following the same procedure as in the preparation of Compound 4 gave Compound 5; $^1$H NMR (300 MHz, CDCl$_3$) δ 8.11 (d, J=8.2 Hz, 2 H), 7.28–7.24 (m, 3 H), 7.17 (dd, J=8.4, 2.2 Hz, 1 H), 6.71 (d, J=8.5 Hz, 1 H), 4.42 (s, 2 H), 2.40 (s, 3 H), 2.05 (s, 3 H), 1.59 (s, 6 H); MS (ES) m/z: 415 (M+H$^+$).

Example 6

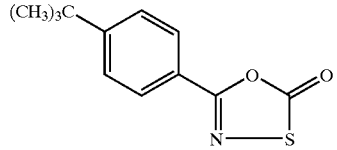

5-(4-tert-Butyl-phenyl)-[1,3,4]oxathiazol-2-one

D6 (clear oil, 70%); $^1$H NMR (300 MHz, CDCl$_3$) δ 7.90 (m, 2 H), 7.50 (m, 2 H), 1.35 (s, 9 H).

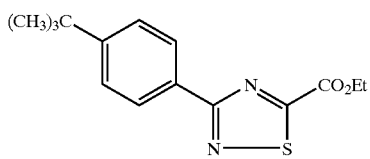

3-(4-tert-Butyl-phenyl)-[1,2,4]thiadiazole-5-carboxylic acid ethyl ester

D7 (yellow crystal, 81%); $^1$H NMR (300 MHz, CDCl$_3$) δ 8.29 (m, 2 H), 7.51 (m, 2 H), 4.55 (q, J=7.1 Hz, 2 H), 1.48 (t, J=7.1 Hz, 3 H), 1.37 (s, 9 H); MS (ES) m/z: 291 (M+H$^+$).

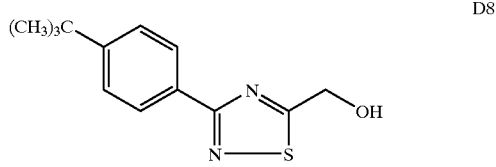

[3-(4-tert-Butyl-phenyl)-[1,2,4]thiadiazol-5-yl]-methanol

D8 (100%); $^1$H NMR (300 MHz, CDCl$_3$) δ 8.19 (m, 2 H), 7.50 (m, 2 H), 5.16 (s, 2 H), 1.36 (s, 9 H); MS (ES) m/z: 249 (M+H$^+$).

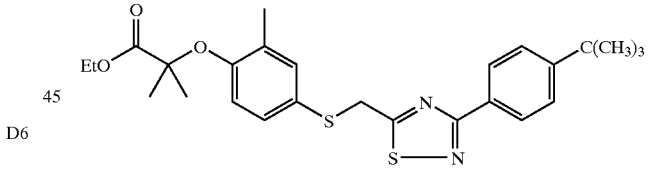

5-Bromomethyl-3-(4-tert-butyl-phenyl)-[1,2,4]thiadiazole

D9 (white crystal, 55%); $^1$H NMR (300 MHz, CDCl$_3$) δ 8.19 (m, 2 H), 7.49 (m, 2 H), 4.82 (s, 2 H), 1.36 (s, 9 H); MS (ES) m/z: 313 (M+H$^+$).

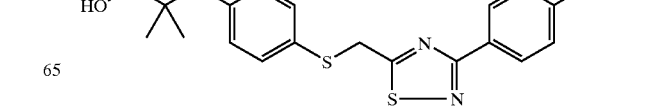

2-{4-[3-(4-tert-Butyl-phenyl)-[1,2,4]thiadiazol-5-ylmethylsulfanyl]-2-methyl-phenoxy}-2-methyl-propionic acid ethyl ester D10 (light yellow oil, 58%); $^1$H NMR (300 MHz, CDCl$_3$) δ 8.15 (m, 2 H), 7.47 (m, 2 H), 7.26 (m, 1 H), 7.13 (dd, J=8.5, 2.4 Hz, 1 H), 6.56 (d, J=8.5 Hz, 1 H), 4.40 (s, 2 H), 4.20 (q, J=7.1 Hz, 2 H), 2.18 (s, 3 H), 1.57 (s, 6 H), 1.35 (s, 9 H), 1.19 (t, J=7.1 Hz, 3 H); MS (ES) m/z: 485 (M+H$^+$).

2-{4-[3-(4-tert-Butyl-phenyl)-[1,2,4]thiadiazol-5-ylmethylsulfanyl]-2-methyl-phenoxy}-2-methyl-propionic acid Compound 6 (yellow gummy material, 81%); $^1$H NMR (400 MHz, CDCl$_3$) δ 8.14 (m, 2 H), 7.47 (m, 2 H), 7.28 (d, J=2.3 Hz, 1 H), 7.17 (dd, J=8.5, 2.4 Hz, 1 H), 6.72 (d, J=8.5 Hz, 1 H), 4.43 (s, 2 H), 2.19 (s, 3 H), 1.60 (s, 6 H), 1.35 (s, 9 H); MS (ES) m/z: 457 (M+H$^+$). Anal. Calcd. For C$_{24}$H$_{28}$N$_2$O$_3$S$_2$: C, 62.27; H, 6.25; N, 6.05. Found: C, 62.48; H, 6.11; N, 5.83.

Example 7

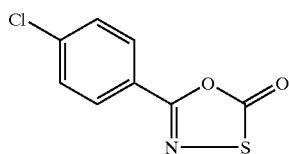

5-(4-Chloro-phenyl)-[1,3,4]oxathiazol-2-one

D11 (pale beige crystalline solid, 63%); $^1$H NMR (300 MHz, CDCl$_3$) δ 7.91 (d, J=8.6 Hz, 2 H), 7.48 (d, J=8.6 Hz, 2 H).

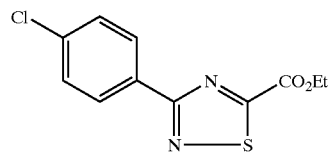

3-(4-Chloro-phenyl)-[1,2,4]thiadiazole-5-carboxylic acid ethyl ester

D12 (white solid, 94%); $^1$H NMR (300 MHz, CDCl$_3$) δ 8.31 (m, 2 H), 7.47 (m, 2 H), 4.55 (q, J=7.1 Hz, 2 H), 1.48 (t, J=7.1 Hz, 3 H); MS (ES) m/z: 269 (M+H$^+$).

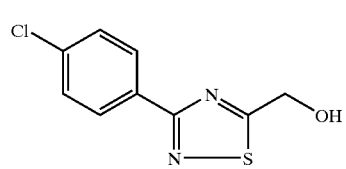

[3-(4-Chloro-phenyl)-[1,2,4]thiadiazol-5-yl]-methanol

D13 (off-white solid, 87%); $^1$H NMR (300 MHz, CDCl$_3$) δ 8.22 (m, 2 H), 7.45 (m, 2 H), 5.17 (s, 2 H); MS (ES) m/z: 227 (M+H$^+$).

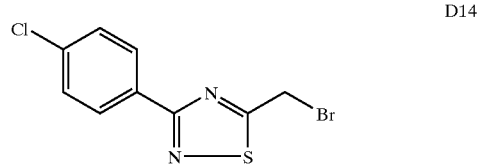

5-Bromomethyl-3-(4-chloro-phenyl)-[1,2,4]thiadiazole

D14 (white solid, 65%); $^1$H NMR (300 MHz, CDCl$_3$) δ 8.22 (m, 2 H), 7.45 (m, 2 H), 4.81 (s, 2 H).

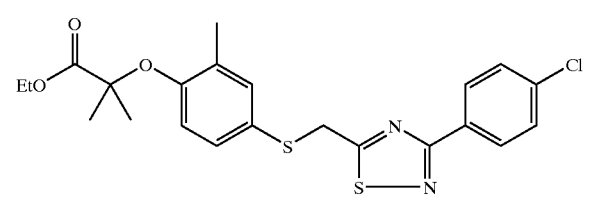

2-{4-[3-(4-Chloro-phenyl)-[1,2,4]thiadiazol-5-ylmethylsulfanyl]-2-methyl-phenoxy}-2-methyl-propionic acid ethyl ester D15 (light yellow oil, 92%); $^1$H NMR (300 MHz, CDCl$_3$) δ 8.17 (m, 2 H), 7.42 (m, 2 H), 7.26 (m, 1 H), 7.14 (dd, J=8.5, 2.4 Hz, 1 H), 6.56 (d, J=8.5 Hz, 1 H), 4.39 (s, 2 H), 4.20 (q, J=7.1 Hz, 2 H), 2.18 (s, 3 H), 1.58 (s, 6 H), 1.19 (t, J=7.1 Hz, 3 H); MS (ES) m/z: 463 (M+H$^+$).

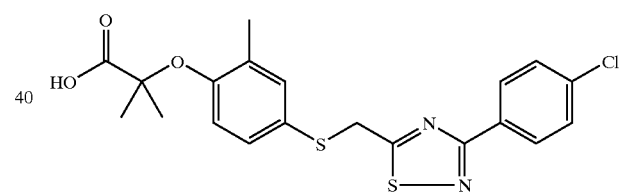

2-{4-[3-(4-Chloro-phenyl)-[1,2,4]thiadiazol-5-ylmethylsulfanyl]-2-methyl-phenoxy}-2-methyl-propionic acid Compound 7 (light yellow solid, 70%); $^1$H NMR (400 MHz, CDCl$_3$) δ 8.17 (m, 2 H), 7.42 (m, 2 H), 7.28 (d, J=2.2 Hz, 1 H), 7.18 (dd, J=8.5, 2.4 Hz, 1 H), 6.72 (d, J=8.5 Hz, 1 H), 4.42 (s, 2 H), 2.19 (s, 3 H), 1.61 (s, 6 H); MS (ES) m/z: 435 (M+H$^+$). Anal. Calcd. For C$_{20}$H$_{19}$ClN$_2$O$_3$S$_2$: C, 55.23; H, 4.40; N, 6.44. Found: C, 54.87; H, 4.20; N, 6.24.

Example 8

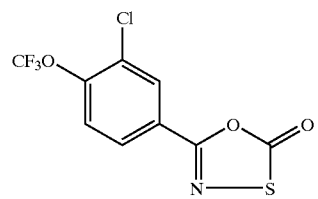

5-(3-Chloro-4-trifluoromethoxy-phenyl)-[1,3,4]oxathiazol-2-one

D16 (beige solid, 88%); $^1$H NMR (300 MHz, CDCl$_3$) δ 8.12 (d, J=2.0 Hz, 1 H), 7.92 (dd, J=8.7, 2.0 Hz, 1 H), 7.45 (dd, J=8.6, 1.1, 1 H).

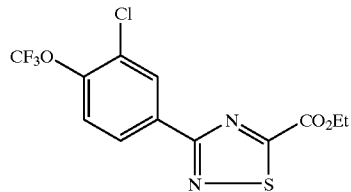

3-(3-Chloro-4-trifluoromethoxy-phenyl)-[1,2,4]thiadiazole-5-carboxylic acid ethyl ester D17 (white crystal, 36%); $^1$H NMR (300 MHz, CDCl$_3$) δ 8.52 (d, J=2.1 Hz, 1 H), 8.31 (dd, J=8.6, 2.1 Hz, 1 H), 7.44 (dd, J=8.6, 1.4, 1 H), 4.56 (q, J=7.1 Hz, 2 H), 1.49 (t, J=7.1 Hz, 3 H); MS (ES) m/z: 375 (M+Na$^+$).

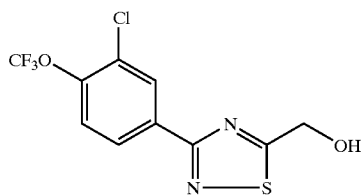

[3-(3-Chloro-4-trifluoromethoxy-phenyl)-[1,2,4]thiadiazol-5-yl]-methanol

D18 (beige solid, 93%); $^1$H NMR (300 MHz, CDCl$_3$) δ 8.42 (d, J=2.1 Hz, 1 H), 8.21 (dd, J=8.6, 2.1 Hz, 1 H), 7.42 (dd, J=8.6, 1.4, 1 H), 5.18 (s, 2 H).

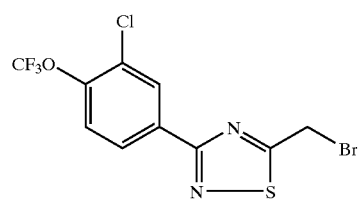

5-Bromomethyl-3-(3-chloro-4-trifluoromethoxy-phenyl)-[1,2,4]thiadiazole

D19 (65%); $^1$H NMR (300 MHz, CDCl$_3$) δ 8.42 (d, J=2.1 Hz, 1 H), 8.21 (dd, J=8.6, 2.1 Hz, 1 H), 7.42 (dd, J=8.6, 1.5, 1 H), 4.81 (s, 2 H).

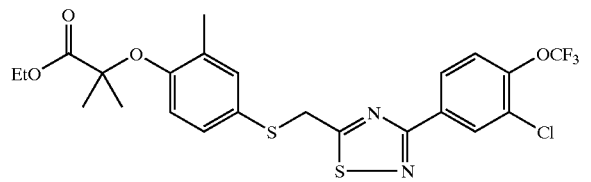

2-{4-[3-(3-Chloro-4-trifluoromethoxy-phenyl)-[1,2,4]thiadiazol-5-ylmethylsulfanyl]-2-methyl-phenoxy}-2-methyl-propionic acid ethyl ester D20 (pale yellow oil, 90%); $^1$H NMR (300 MHz, CDCl$_3$) δ 8.37 (d, J=2.0 Hz, 1 H), 8.16 (dd, J=8.6, 2.1 Hz, 1 H), 7.40 (dd, J=8.6, 1.4 Hz, 1 H), 7.26 (m, 1 H), 7.13 (dd, J=8.5, 2.3 Hz, 1 H), 6.56 (d, J=8.5 Hz, 1 H), 4.39 (s, 2 H), 4.20 (q, J=7.1 Hz, 2 H), 2.19 (s, 3 H), 1.58 (s, 6 H), 1.20 (t, J=7.1 Hz, 3 H); MS (ES) m/z: 547 (M+H$^+$).

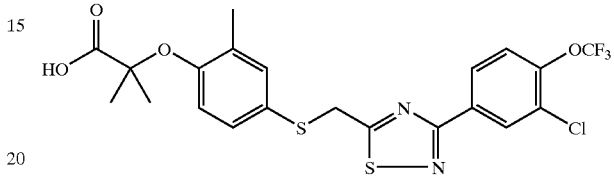

2-{4-[3-(3-Chloro-4-trifluoromethoxy-phenyl)-[1,2,4]thiadiazol-5-ylmethylsulfanyl]-2-methyl-phenoxy}-2-methyl-propionic acid Compound 8 (pale yellow gummy material, 34%); $^1$H NMR (300 MHz, CDCl$_3$) δ 8.37 (d, J=2.1 Hz, 1 H), 8.16 (dd, J=8.6, 2.1 Hz, 1 H), 7.40 (dd, J=8.6, 1.5 Hz, 1 H), 7.28 (d, J=2.0 Hz, 1 H), 7.17 (dd, J=8.4, 2.3 Hz, 1 H), 6.72 (d, J=8.5 Hz, 1 H), 4.42 (s, 2 H), 2.20 (s, 3 H), 1.61 (s, 6 H); MS (ES) m/z: 519 (M+H$^+$).

Example 9

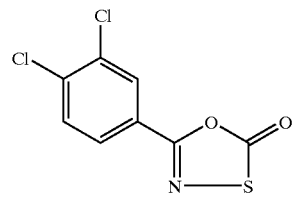

5-(3,4-Dichloro-phenyl)-[1,3,4]oxathiazol-2-one

D21 (off-white solid, 94%); $^1$H NMR (300 MHz, CDCl$_3$) δ 8.07 (d, J=2.0 Hz, 1 H), 7.80 (dd, J=8.4, 2.0 Hz, 1 H), 7.58 (d, J=8.4, 1 H).

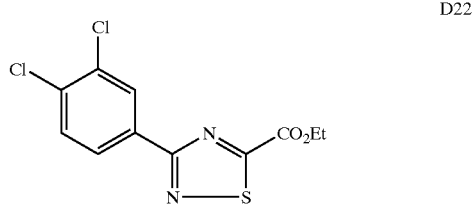

3-(3,4-Dichloro-phenyl)-[1,2,4]thiadiazole-5-carboxylic acid ethyl ester

D22 (yellow solid, 91%); $^1$H NMR (300 MHz, CDCl$_3$) δ 8.48 (d, J=2.0 Hz, 1 H), 8.20 (dd, J=8.4, 2.0 Hz, 1 H), 7.57 (d, J=8.4,1 H), 4.56 (q, J=7.1 Hz, 2 H), 1.49 (t, J=7.1 Hz, 3 H); MS (ES) m/z: 303 (M+H$^+$).

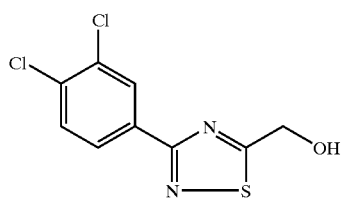

[3-(3,4-Dichloro-phenyl)-[1,2,4]thiadiazol-5-yl]-methanol

D23 (pale yellow solid, 86%); $^1$H NMR (400 MHz, DMSO-d$_6$) δ 8.33 (d, J=1.9 Hz, 1 H), 8.15 (m, 1 H), 7.82 (d, J=8.4,1 H), 4.99 (s, 2 H).

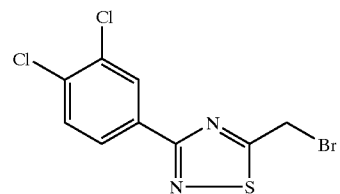

5-Bromomethyl-3-(3,4-dichloro-phenyl)-[1,2,4]thiadiazole

D24 (white solid, 57%); $^1$H NMR (300 MHz, CDCl$_3$) δ 8.39 (d, J=2.0 Hz, 1 H), 8.11 (dd, J=8.4, 2.0 Hz, 1 H), 7.55 (d, J=8.4, 1 H), 4.81 (s, 2 H).

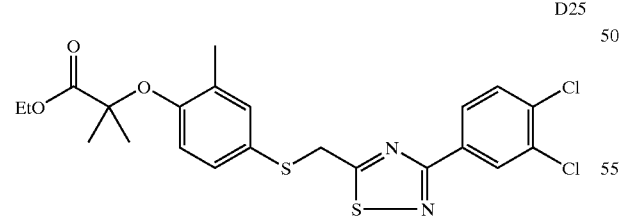

2-{4-[3-(3,4-Dichloro-phenyl)-[1,2,4]thiadiazol-5-ylmethylsulfanyl]-2-methyl-phenoxy}-2-methyl-propionic acid ethyl ester D25 (light yellow oil, 99%); $^1$H NMR (400 MHz, CDCl$_3$) δ 8.34 (d, J=2.0 Hz, 1 H), 8.06 (dd, J=8.4, 2.0 Hz, 1 H), 7.53 (d, J=8.4 Hz, 1 H), 7.27 (m, 1 H), 7.13 (dd, J=8.5, 2.4 Hz, 1 H), 6.56 (d, J=8.5 Hz, 1 H), 4.39 (s, 2 H), 4.20 (q, J=7.1 Hz, 2 H), 2.19 (s, 3 H), 1.58 (s, 6 H), 1.20 (t, J=7.1 Hz, 3 H); MS (ES) m/z: 497 (M+H$^+$).

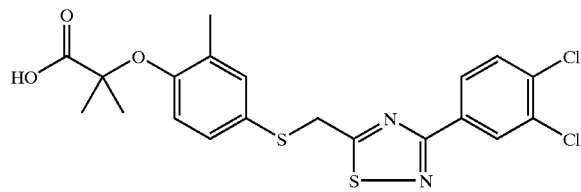

2-{4-[3-(3,4-Dichloro-phenyl)-[1,2,4]thiadiazol-5-ylmethylsulfanyl]-2-methyl-phenoxy}-2-methyl-propionic acid Compound 9 (light yellow solid, 82%); $^1$H NMR (300 MHz, CDCl$_3$) δ 8.34 (d, J=2.0 Hz, 1 H), 8.06 (dd, J=8.4, 2.0 Hz, 1 H), 7.52 (d, J=8.4 Hz, 1 H), 7.28 (d, J=2.1 Hz, 1 H), 7.17 (dd, J=8.4, 2.4 Hz, 1 H), 6.73 (d, J=8.5 Hz, 1 H), 4.4 (s, 2 H), 2.20 (s, 3 H), 1.61 (s, 6 H); MS (ES) m/z: 469 (M+H$^+$). Anal. Calcd. For C$_{20}$H$_{18}$Cl$_2$N$_2$O$_3$S0.10 H$_2$O: C, 50.98; H, 3.89; N, 5.94. Found: C, 50.60; H, 3.53; N, 5.71.

Example 10

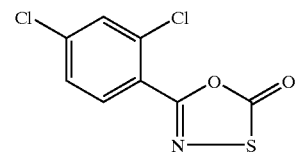

5-(2,4-Dichloro-phenyl)-[1,3,4]oxathiazol-2-one

D26 (off-white solid, 54%); $^1$H NMR (300 MHz, CDCl$_3$) δ 7.81 (d, J=8.5 Hz, 1 H), 7.56 (d, J=2.1 Hz, 1 H), 7.39 (m, 1 H).

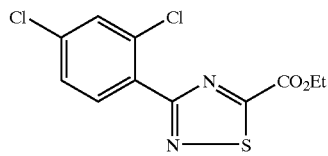

3-(2,4-Dichloro-phenyl)-[1,2,4]thiadiazole-5-carboxylic acid ethyl ester

D27 (beige solid, 55%); $^1$H NMR (300 MHz, CDCl$_3$) δ 7.99 (d, J=8.4 Hz, 1 H), 7.56 (d, J=2.0 Hz, 1 H), 7.38 (dd, J=8.4, 2.0 Hz, 1 H), 4.56 (q, J=7.1 Hz, 2 H), 1.48 (t, J=7.1 Hz, 3 H); MS (ES) m/z: 303 (M+H$^+$).

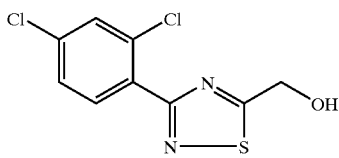

[3-(2,4-Dichloro-phenyl)-
[1,2,4]thiadiazol-5-yl]-methanol

D28 (white solid, 56%); $^1$H NMR (300 MHz, CDCl$_3$) δ 7.91 (d, J=8.4 Hz, 1 H), 7.55 (d, J=2.1 Hz, 1 H), 7.36 (dd, J=8.4, 2.1 Hz, 1 H), 5.20 (s, 2 H); MS (ES) m/z: 261 (M+H$^+$).

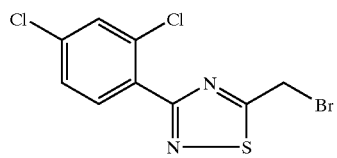

5-Bromomethyl-3-
(2,4-dichloro-phenyl)-[1,2,4]thiadiazole

D29 (white solid, 87%); $^1$H NMR (400 MHz, CDCl$_3$) δ 7.92 (d, J=8.4 Hz, 1 H), 7.55 (d, J=2.1 Hz, 1 H), 7.37 (dd, J=8.4, 2.1 Hz, 1 H), 4.84 (s, 2 H); MS (ES) m/z: 325 (M+H$^+$).

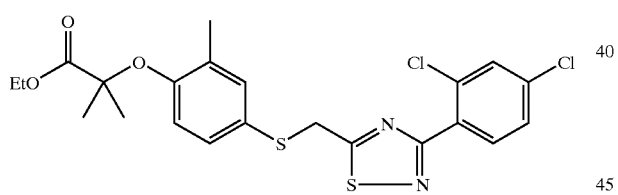

2-{4-[3-(2,4-Dichloro-phenyl)-[1,2,4]thiadiazol-5-ylmethylsulfanyl]-2-methyl-phenoxy}-2-methyl-propionic acid ethyl ester D30 (clear oil, 88%); $^1$H NMR (300 MHz, CDCl$_3$) δ 7.85 (d, J=8.4 Hz, 1 H), 7.52 (d, J=2.1 Hz, 1 H), 7.33 (dd, J=8.4, 2.1 Hz, 1 H), 7.25 (m, -1 H), 7.15 (dd, J=8.5, 2.4 Hz, 1 H), 6.57 (d, J=8.5 Hz, 1 H), 4.41 (s, 2 H), 4.21 (q, J=7.1 Hz, 2 H), 2.19 (s, 3 H), 1.59 (s, 6 H), 1.21 (t, J=7.1 Hz, 3 H); MS (ES) m/z: 497 (M+H$^+$).

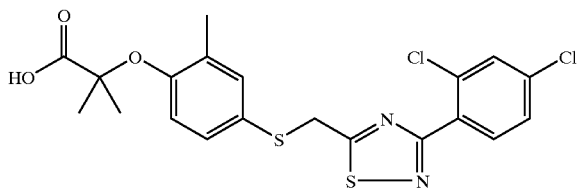

2-{4-[3-(2,4-Dichloro-phenyl)-[1,2,4]thiadiazol-5-ylmethylsulfanyl]-2-methyl-phenoxy}-2-methyl-propionic acid Compound 10 (pale yellow solid, 81%); $^1$H NMR (300 MHz, CDCl$_3$) δ 7.85 (d, J=8.4 Hz, 1 H), 7.52 (d, J=2.0 Hz, 1 H), 7.33 (dd, J=8.4, 2.1 Hz, 1 H), 7.28 (d, J=2.2 Hz, 1 H), 7.19 (dd, J=8.4, 2.4 Hz, 1 H), 6.73 (d, J -=8.5 Hz, 1 H), 4.44 (s, 2 H), 2.20 (s, 3 H), 1.61 (s, 6 H); MS (ES) m/z: 469 (M+H$^+$). Anal. Calcd. For C$_{20}$H$_{18}$Cl$_2$N$_2$O$_3$S$_2$: C, 51.17; H, 3.87; N, 5.97. Found: C, 50.80; H, 3.53; N, 5.72.

Example 11

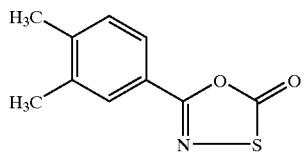

5-(3,4-Dimethyl-phenyl)-[1,3,4]oxathiazol-2-one

D31 (white solid, 47%); $^1$H NMR (400 MHz, CDCl$_3$) δ 7.74 (s, 1 H), 7.69 (d, J=7.9 Hz, 1 H), 7.24 (d, J=8.2 Hz, 1 H), 2.33 (s, 6 H).

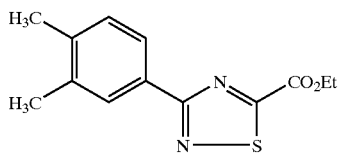

3-(3,4-Dimethyl-phenyl)-[1,2,4]thiadiazole-5-carboxylic acid ethyl ester

D32 (brown crystal, 47%); $^1$H NMR (300 MHz, CDCl$_3$) δ 8.15 (s, 1 H), 8.09 (d, J=7.9 Hz, 1 H), 7.24 (m, 1 H), 4.55 (q, J=7.1 Hz, 2 H), 2.35 (s, 3 H), 2.3 (s, 3 H), 1.48 (t, J=7.1 Hz, 3 H); MS (ES) m/z: 263 (M+H$^+$).

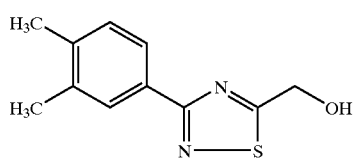

[3-(3,4-Dimethyl-phenyl)-
[1,2,4]thiadiazol-5-yl]-methanol

D33 (white solid, 85%); $^1$H NMR (300 MHz, CDCl$_3$) δ 8.06 (s, 1 H), 8.00 (d, J=7.8 Hz, 1 H), 7.24 (d, J=7.9 Hz, 1 H), 5.17 (s, 2 H), 2.62 (brs, 1 H), 2.34 (s, 3 H), 2.32 (s, 3 H); MS (ES) m/z: 221 (M+H$^+$).

Example 12

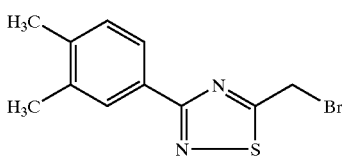
D34

5-Bromomethyl-3-(3,4-dimethyl-phenyl)-[1,2,4]thiadiazole

D34 (white solid, 91%); $^1$H NMR (300 MHz, CDCl$_3$) δ 8.05 (s, 1 H), 7.99 (d, J=7.8 Hz, 1 H), 7.23 (d, J=7.9 Hz, 1 H), 4.82 (s, 2 H), 2.34 (s, 3 H), 2.32 (s, 3 H); MS (ES) m/z: 285 (M+H$^+$).

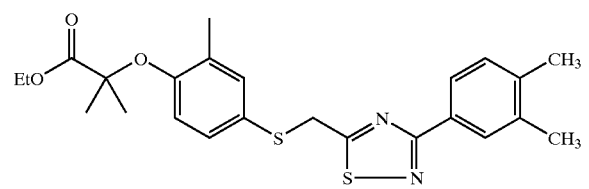
D35

2-{4-[3-(3,4-Dimethyl-phenyl)-[1,2,4]thiadiazol-5-ylmethylsulfanyl]-2-methyl-phenoxy}-2-methyl-propionic acid ethyl ester D35 (clear oil, 97%); $^1$H NMR (400 MHz, CDCl$_3$) δ 8.01 (s, 1 H), 7.96 (d, J=7.9 Hz, 1 H), 7.29 (s, 1 H), 7.22 (d, J=8.0 Hz, 1 H), 7.15 (dd, J=8.4, 2.4 Hz, 1 H), 6.56 (d, J=8.3 Hz, 1 H), 4.41 (s, 2 H), 4.20 (q, J=7.1 Hz, 2 H), 2.34 (s, 3 H), 2.32 (s, 3 H), 2.19 (s, 3 H), 1.58 (s, 6 H), 1.20 (t, J=7.1 Hz, 3 H); MS (ES) m/z: 457 (M+H$^+$).

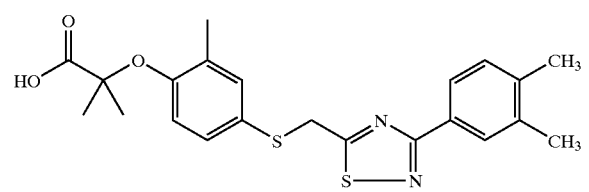

2-{4-[3-(3,4-Dimethyl-phenyl)-[1,2,4]thiadiazol-5-ylmethylsultanyl]-2-methyl-phenoxy}-2-methyl-propionic acid Compound 11 (light yellow solid, 76%); $^1$H NMR (400 MHz, CDCl$_3$) δ 8.00 (s, 1 H), 7.94 (dd, J=7.8, 1.5 Hz, 1 H), 7.28 (d, J=1.9 Hz, 1 H), 7.21 (d, J=7.8 Hz, 1 H), 7.17 (dd, J=8.5, 2.2 Hz, 1 H), 6.71 (d, J=8.5 Hz, 1 H), 4.42 (s, 2 H), 2.32 (s, 3 H), 2.31 (s, 3 H), 2.19 (s, 3 H), 1.59 (s, 6 H); MS (ES) m/z: 429 (M+H$^+$).

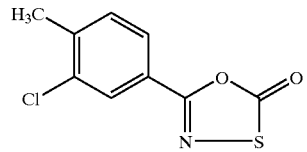
D36

5-(3-Chloro-4-methyl-phenyl)-[1,3,4]oxathiazol-2-one

D36 (light brown solid, 57%); $^1$H NMR (300 MHz, CDCl$_3$) δ 7.96 (d, J=1.7 Hz, 1 H), 7.75 (dd, J=8.0, 1.8 Hz, 1 H), 7.35 (d, J=8.0 Hz, 1 H).

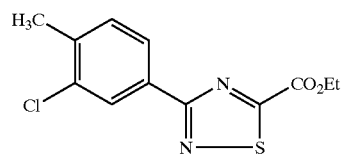
D37

3-(3-Chloro-4-methyl-phenyl)-[1,2,4]thiadiazole-5-carboxylic acid ethyl ester

D37 (white solid, 87%); $^1$H NMR (300 MHz, CDCl$_3$) δ 8.37 (d, J=1.7 Hz, 1 H), 8.15 (dd, J=7.9, 1.7 Hz, 1 H), 7.35 (d, J=7.9 Hz, 1 H), 4.55 (q, J=7.1 Hz, 2 H), 2.44 (s, 3 H), 1.49 (t, J=7.1 Hz, 3 H); MS (ES) m/z: 283 (M+H$^+$).

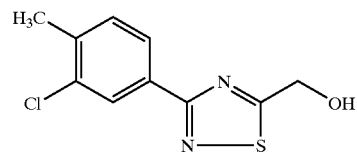
D38

[3-(3-Chloro-4-methyl-phenyl)-[1,2,4]thiadiazol-5-yl]-methanol

D38 (white solid, 90%); $^1$H NMR (400 MHz, CDCl$_3$) δ 8.28 (d, J=1.7 Hz, 1 H), 8.06 (dd, J=7.9, 1.7 Hz, 1 H), 7.33 (d, J=8.0 Hz, 1 H), 5.17 (s, 2 H), 2.44 (s, 3 H); MS (ES) m/z: 241 (M+H$^+$).

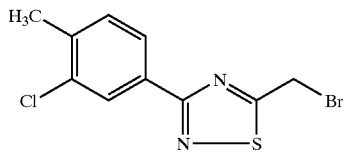
D39

5-Bromomethyl-3-(3-chloro-4-methyl-phenyl)-[1,2,4]thiadiazole

D39 (white solid, 75%); $^1$H NMR (300 MHz, CDCl$_3$) δ 8.27 (d, J=1.7 Hz, 1 H), 8.05 (dd, J=7.9, 1.7 Hz, 1 H), 7.33 (d, J=7.9 Hz, 1 H), 4.81 (s, 2 H), 2.44 (s, 3 H); MS (ES) m/z: 305 (M+H$^+$).

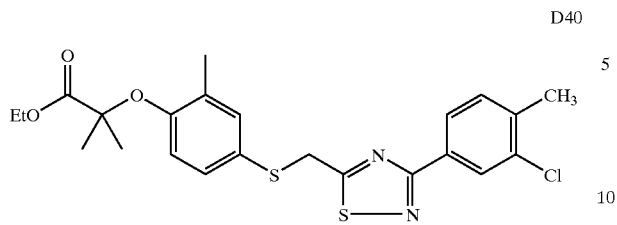

D40

2-{4-[3-(3-Chloro-4-methyl-phenyl)-[1,2,4]thiadiazol-5-ylmethylsulfanyl]-2-methyl-phenoxy}-2-methyl-propionic acid ethyl ester D40 (white solid, 98%); $^1$H NMR (300 MHz, CDCl$_3$) δ 8.22 (d, J=1.7 Hz, 1 H), 8.01 (dd, J=7.9, 1.7 Hz, 1 H), 7.30 (d, J=7.9 Hz, 1 H), 7.26 (s, 1 H), 7.14 (dd, J=8.5, 2.5 Hz, 1 H), 6.56 (d, J=8.5 Hz, 1 H), 4.39 (s, 2 H), 4.20 (q, J=7.1 Hz, 2 H), 2.42 (s, 3 H), 2.18 (s, 3 H), 1.58 (s, 6 H), 1.20 (t, J=7.1 Hz, 3 H); MS (ES) m/z: 477 (M+H$^+$).

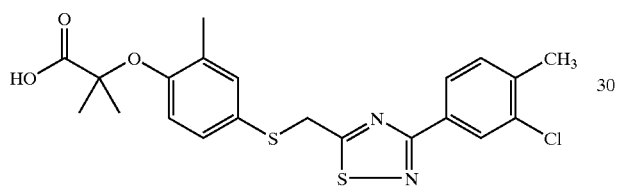

2-{4-[3-(3-Chloro-4-methyl-phenyl)-[1,2,4]thiadiazol-5-ylmethylsulfanyl]-2-methyl-phenoxy}-2-methyl-propionic acid Compound 12 (light yellow solid, 75%); $^1$H NMR (300 MHz, CDCl$_3$) δ 8.21 (d, J=1.7 Hz, 1 H), 8.01 (dd, J=8.0, 1.7 Hz, 1 H), 7.30 (d, J=8.2 Hz, 1 H), 7.27 (s, 1 H), 7.17 (dd, J=8.5, 2.2 Hz, 1 H), 6.72 (d, J=8.5 Hz, 1 H), 4.41 (s, 2 H), 2.42 (s, 3 H), 2.19 (s, 3 H), 1.59 (s, 6 H).

Example 13

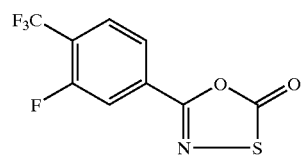

D41

5-(3-Fluoro-4-trifluoromethyl-phenyl)-[1,3,4]oxathiazol-2-one

D41 (off-white solid, 96%); $^1$H NMR (400 MHz, CDCl$_3$) δ 7.87 (d, J=8.2 Hz, 1 H), 7.83 (d, J=10.6 Hz, 1 H), 7.77 (m, 1 H).

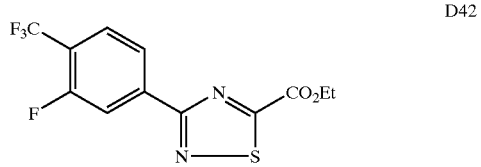

D42

3-(3-Fluoro-4-trifluoromethyl-phenyl)-[1,2,4]thiadiazole-5-carboxylic acid ethyl ester D42 (brown crystal, 69%); $^1$H NMR (400 MHz, CDCl$_3$) δ 8.26 (d, J=8.2 Hz, 1 H), 8.22 (d, J=11.2 Hz, 1 H), 7.74 (t, J=7.6 Hz, 1 H), 4.57 (q, J=7.1 Hz, 2 H), 1.50 (t, J=7.1 Hz, 3 H); MS (ES) m/z: 321 (M+H$^+$).

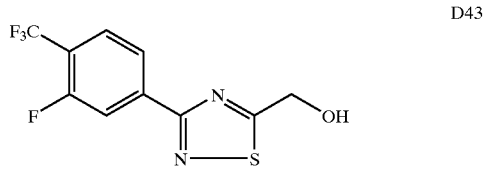

D43

[3-(3-Fluoro-4-trifluoromethyl-phenyl)-[1,2,4]thiadiazol-5-yl]-methanol

D43 (yellow oil, 88%); $^1$H NMR (300 MHz, CDCl$_3$) δ 8.17 (d, J=8.5 Hz, 1 H), 8.13 (d, J=11.6 Hz, 1 H), 7.71 (m, 1 H), 5.19 (s, 2 H); MS (ES) m/z: 279 (M+H$^+$).

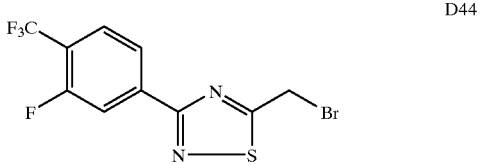

D44

5-Bromomethyl-3-(3-fluoro-4-trifluoromethyl-phenyl)-[1,2,4]thiadiazole

D44 (white solid, 66%); $^1$H NMR (300 MHz, CDCl$_3$) δ 8.17 (d, J=8.4 Hz, 1 H), 8.12 (d, J=11.5 Hz, 1 H), 7.72 (t, J=7.6 Hz, 1 H), 4.82 (s, 2 H); MS (ES) m/z: 343 (M+H$^+$).

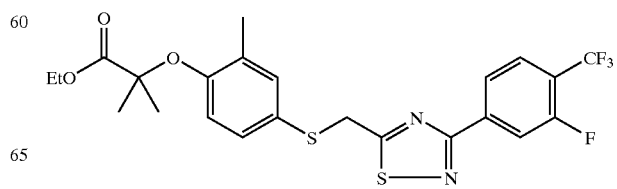

D45

2-{4-[3-(3-Fluoro-4-trifluoromethyl-phenyl)-[1,2,4]
thiadiazol-5-ylmethylsulfanyl]-2-methyl-phenoxy}-
2-methyl-propionic acid ethyl ester D45 (clear oil, 79%); $^1$H NMR (300 MHz, CDCl$_3$) δ 8.11 (d, J=8.4 Hz, 1 H), 8.07 (d, J=11.3 Hz, 1 H), 7.69 (t, J=7.7 Hz, 1 H), 7.26 (m, 1 H), 7.14 (dd, J=8.5, 2.5 Hz, 1 H), 6.57 (d, J=8.5 Hz, 1 H), 4.40 (s, 2 H), 4.20 (q, J=7.1 Hz, 2 H), 2.19 (s, 3 H), 1.58 (s, 6 H), 1.20 (t, J=7.1 Hz, 3 H); MS (ES) m/z: 515 (M+H$^+$).

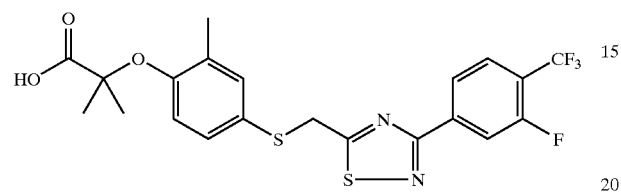

2-{4-[3-(3-Fluoro-4-trifluoromethyl-phenyl)-[1,2,4]
thiadiazol-5-ylmethylsulfanyl]-2-methyl-phenoxy}-
2-methyl-propionic acid Compound 13 (yellow oil, 99%); $^1$H NMR (300 MHz, CDCl$_3$) δ 8.11 (d, J=8.1 Hz, 1 H), 8.06 (d, J=11.3 Hz, 1 H), 7.69 (t, J=7.6 Hz, 1 H), 7.28 (m, 1 H), 7.17 (dd, J=8.6, 2.5 Hz, 1 H), 6.72 (d, J=8.5 Hz, 1 H), 4.42 (s, 2 H), 2.20 (s, 3 H), 1.61 (s, 6 H); MS (ES) m/z: 487 (M+H$^+$).

Example 14

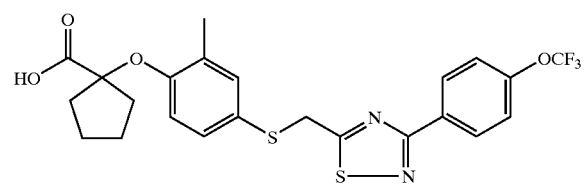

1-{2-Methyl-4-[3-(4-trifluoromethoxy-phenyl)-[1,2,
4]thiadiazol-5-ylmethylsulfanyl]-phenoxy}-cyclo-
pentanecarboxylic acid Scheme E1

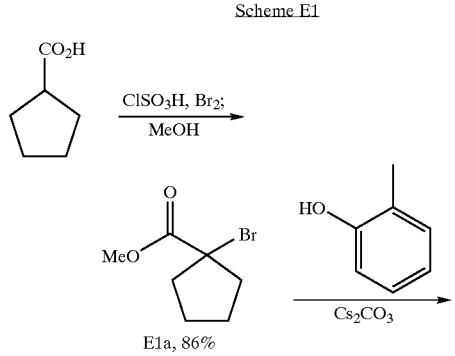

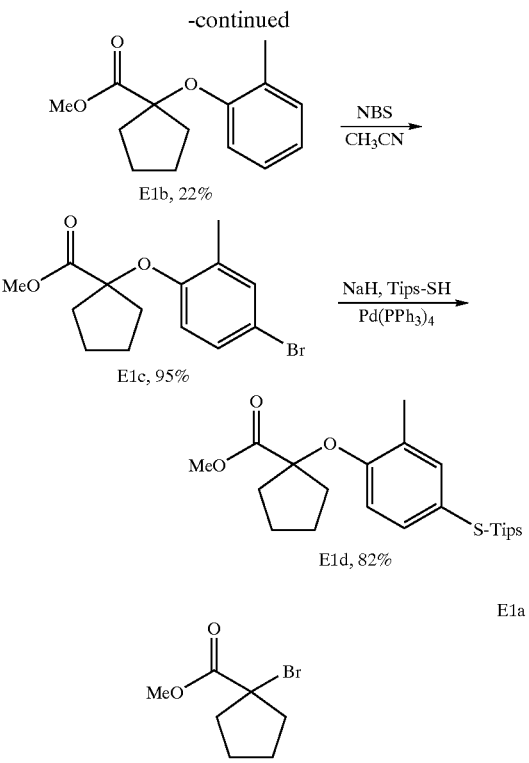

1-Bromo-cyclopentanecarboxylic acid methyl ester

To a solution of cyclopentanecarboxylic acid (1.14 g, 10.0 mmol) in 1,2-dichloroethane (50 mL) were added bromine (1.60 g, 10.0 mmol) and chlorosulfonic acid (1.17 g, 10.0 mmol). The reaction mixture was refluxed for 2 h and concentrated. The residue was dissolved in MeOH (30 mL) and the mixture was refluxed overnight. After removal of the solvent, the residue was diluted with Et$_2$O, washed with water (×2) and brine, dried over Na$_2$SO$_4$, filtered, and concentrated to give 1.79 g (86%) of E1a; $^1$H NMR (300 MHz, CDCl$_3$) δ 3.80 (s, 3 H), 2.33–2.28 (m, 4 H), 2.03–1.95 (m, 2 H), 1.85–1.75 (m, 2 H).

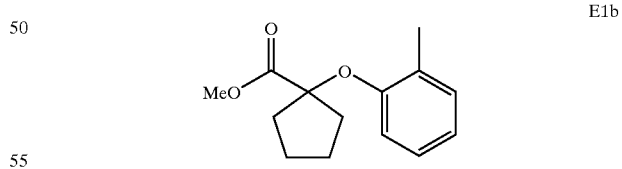

1-o-Tolyloxy-cyclopentanecarboxylic acid methyl ester

To a solution of 2-methylphenol (90 mg, 0.83 mmol) in CH$_3$CN (2 mL) was added CS$_2$CO$_3$ (678 mg, 2.08 mmol) followed by E1a (207 mg, 1.00 mmol). The mixture was heated at 70° C. for 4.5 h, diluted with water, and extracted with Et$_2$O. The extracts were dried, concentrated, and column chromatographed (EtOAc/hexane: 1/12) to give 52 mg (22%) of E1b; ¹H NMR (300 MHz, CDCl₃) δ 7.13 (d, J=7.3 Hz, 1 H), 7.03 (m, 1 H), 6.83 (td, J=7.4, 0.7 Hz, 1 H), 6.45 (d, J=8.1 Hz, 1 H), 3.73 (s, 3 H), 2.29–2.17 (m, 4 H), 2.23 (s, 3 H), 1.84–1.76 (m, 4 H); MS (ES) m/z: 235 (M+H⁺).

E1c

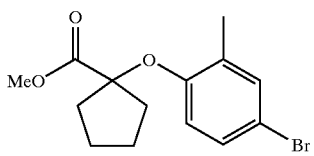

1-(4-Bromo-2-methyl-phenoxy)-cyclopentanecarboxylic acid methyl ester

To a solution of E1b (76 mg, 0.32 mmol) in CH₃CN (1.5 mL) was added N-bromosuccinimide (63 mg, 0.35 mmol). After stirring at room temperature for 1.5 h, additional N-bromosuccinimide (29 mg, 0.16 mmol) was added and the mixture was stirred for another 1 h. After removal of the solvent under reduced pressure, the residue was purified by column chromatography (CH₂Cl₂/hexane: 1/1) to provide 95 mg (95%) of E1c; ¹H NMR (300 MHz, CDCl₃) δ 7.25 (d, J=0.5 Hz, 1 H), 7.13 (dd, J=8.6, 2.4 Hz, 1 H), 6.32 (d, J=8.7 Hz, 1 H), 3.73 (s, 3 H), 2.28–2.12 (m, 4 H), 2.19 (s, 3 H), 1.82–1.77 (m, 4 H); MS (ES) m/z: 314 (M+H⁺).

E1d

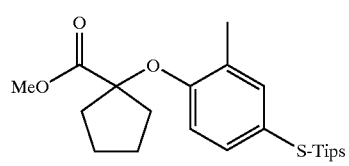

1(2-Methyl-4-triisopropylsilanylsulfanyl-phenoxy)-cyclopentanecarboxylic acid methyl ester To a suspension of NaH (17 mg, 0.43 mmol; 60% in mineral oil) in toluene (1.5 mL) was added triisopropylsilanethiol (82 mg, 0.43 mmol). After stirring at room temperature for 30 min, to the mixture a solution of E1c (122 mg, 0.390 mmol) in THF (1 mL) and tetrakis(triphenylphosphine) palladium (45 mg, 0.039 mmol) were added, and the mixture was degassed under N₂. After heating at 90° C. for 4 h, the solvents were evaporated and the residue was purified by column chromatography (EtOAc/hexane: 1/8) to afford 135 mg (82%) of E1d; ¹H NMR (300 MHz, CDCl₃) δ 7.25 (d, J=1.8 Hz, 1 H), 7.13 (dd, J=8.5, 2.3 Hz, 1 H), 6.32 (d, J=8.5 Hz, 1 H), 3.70 (s, 3 H), 2.25–2.13 (m, 4 H), 2.16 (s, 3 H), 1.82–1.77 (m, 4 H), 1.27–1.19 (m, 3 H), 1.07 (s, 9 H), 1.04 (s, 9 H); MS (ES) m/z: 423 (M+H⁺).

Scheme E2

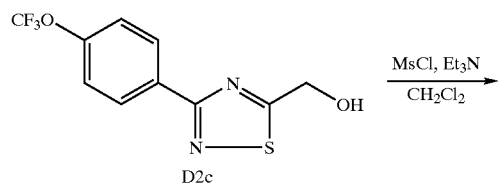

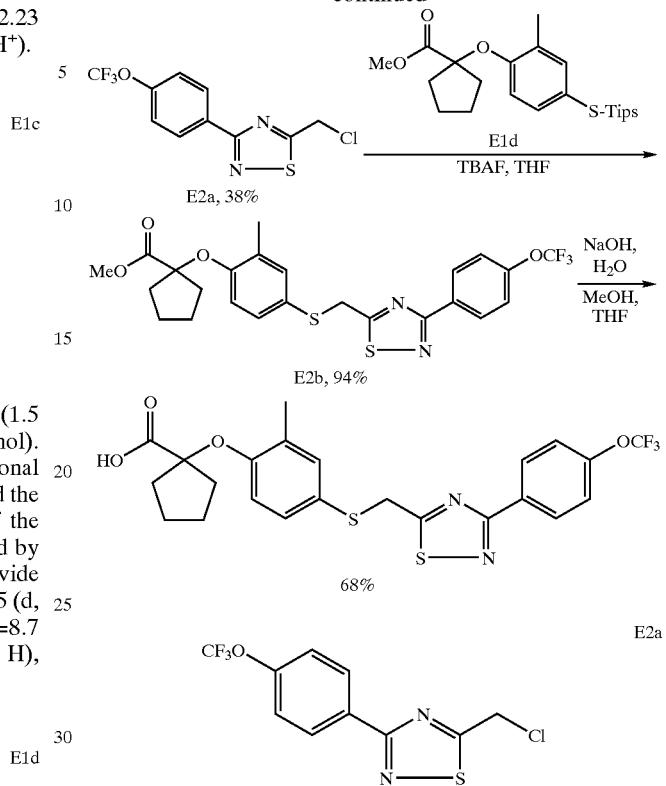

5-Chloromethyl-3-(4-trifluoromethoxy-phenyl)-[1,2,4]thiadiazole

To a solution of D2c (483 mg, 1.75 mmol) in CH₂Cl₂ (6 mL) at 0° C. were added methanesulfonyl chloride (607 mg, 5.30 mmol) and triethylamine (886 mg, 8.77 mmol). The mixture was stirred at room temperature for 23 h and partitioned between water and CH₂Cl₂. The organic phase was washed with brine, dried, concentrated, and column chromatographed to provide 197 mg (38%) of E2a as a light yellow solid; ¹H NMR (400 MHz, CDCl₃) δ 8.32 (m, 2 H), 7.32 (dd, J=8.9, 0.9 Hz, 2 H), 4.99 (s, 2 H); MS (ES) m/z: 295 (M+H⁺).

E2b

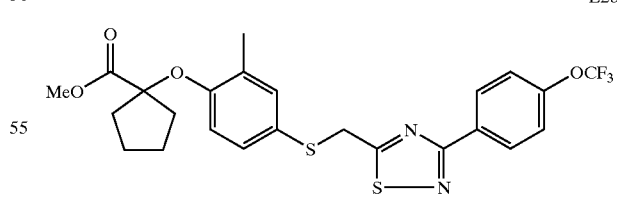

1-{2-Methyl-4-[3-(4-trifluoromethoxy-phenyl)-[1,2,4]thiadiazol-5-ylmethylsulfanyl]-phenoxy}-cyclopentanecarboxylic acid methyl ester To a mixture of E2a (53 mg, 0.18 mmol) and E1d (76 mg, 0.18 mmol) in THF (0.5 mL) at 0° C. was added 1.0 M tetrabutylammonium fluoride (0.18 mL, 0.18 mmol) in THF dropwise. After stirring at the same temperature for 15 min, the mixture was concentrated and the residue was purified by column chromatography to afford 88 mg (94%) of E2b as a clear oil; $^1$H NMR (300 MHz, CDCl$_3$) δ 8.27 (d, J=8.9 Hz, 2 H), 7.30–7.26 (m, 3 H), 7.14 (dd, J=8.5, 2.2 Hz, 1 H), 6.37 (d, J=8.5 Hz, 1 H), 4.39 (s, 2 H), 3.70 (s, 3 H), 2.27–2.12 (m, 4 H), 2.18 (s, 3 H), 1.80–1.76 (m, 4 H); MS (ES) m/z: 525 (M+H$^+$).

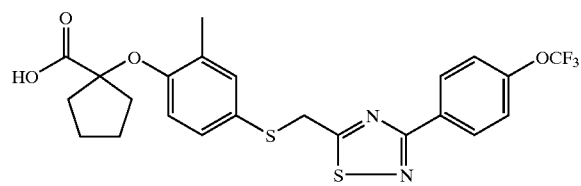

1-{2-Methyl-4-[3-(4-trifluoromethoxy-phenyl)-[1,2,4]thiadiazol-5-ylmethylsulfanyl]-phenoxy}-cyclopentanecarboxylic acid Compound 14 (68%); $^1$H NMR (400 MHz, CDCl$_3$) δ 8.27 (m, 2 H), 7.30–7.27 (m, 3 H), 7.17 (dd, J=8.5, 2.3 Hz, 1 H), 6.50 (d, J=8.5 Hz, 1 H), 4.40 (s, 2 H), 2.36–2.27 (m, 2 H), 2.21–2.15 (m, 2 H), 2.18 (s, 3 H), 1.82–1.78 (m, 4 H)

Anal. Calcd. For C$_{23}$H$_{21}$F$_3$N$_2$O$_4$S$_2$: C, 54.11; H, 4.15; N, 5.49. Found: C, 53.98; H, 4.15; N, 5.29.

Example 15

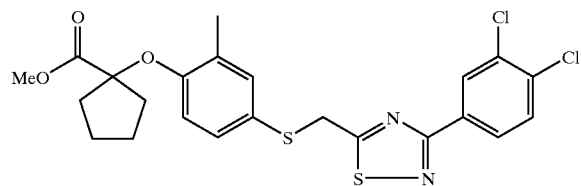

1-{4-[3-(3,4-Dichloro-phenyl)-[1,2,4]thiadiazol-5-ylmethylsulfanyl]-2-methyl-phenoxy}-cyclopentanecarboxylic acid methyl ester E2c (pale yellow oil, 93%); $^1$H NMR (300 MHz, CDCl$_3$) δ 8.35 (d, J=2.0 Hz, 1 H), 8.07 (dd, J=8.4, 2.0 Hz, 1 H), 7.53 (d, J=8.4 Hz, 1 H), 7.26 (s, 1 H), 7.13 (dd, J=8.5, 2.4 Hz, 1 H), 6.37 (d, J=8.5 Hz, 1 H), 4.38 (s, 2 H), 3.70 (s, 3 H), 2.28–2.12 (m, 4 H), 2.18 (s, 3 H), 1.81–1.76 (m, 4 H); MS (ES) m/z: 509 (M+H$^+$).

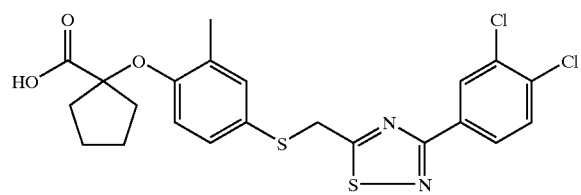

1-{4-[3-(3,4-Dichloro-phenyl)-[1,2,4]thiadiazol-5-ylmethylsulfanyl]-2-methyl-phenoxy}-cyclopentanecarboxylic acid Compound 15 (light yellow oil, 35%); $^1$H NMR (400 MHz, CDCl$_3$) δ 8.34 (d, J=2.0 Hz, 1 H), 8.06 (dd, J=8.4, 2.0 Hz, 1 H), 7.52 (d, J=8.4 Hz, 1 H), 7.28–7.26 (m, 1 H), 7.17 (dd, J=8.4, 2.3 Hz, 1 H), 6.50 (d, J=8.5 Hz, 1 H), 4.39 (s, 2 H), 2.36–2.27 (m, 2 H), 2.21–2.15 (m, 2 H), 2.17 (s, 3 H), 1.82–1.79 (m, 4 H); MS (ES) m/z: 495 (M+H$^+$).

Example 16

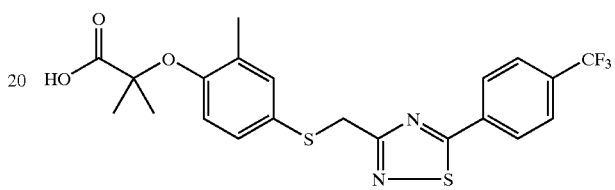

2-Methyl-2-{2-methyl-4-[5-(4-trifluoromethyl-phenyl)-[1,2,4]thiadiazol-3-ylmethylsulfanyl]-phenoxy}-propionic acid Scheme F

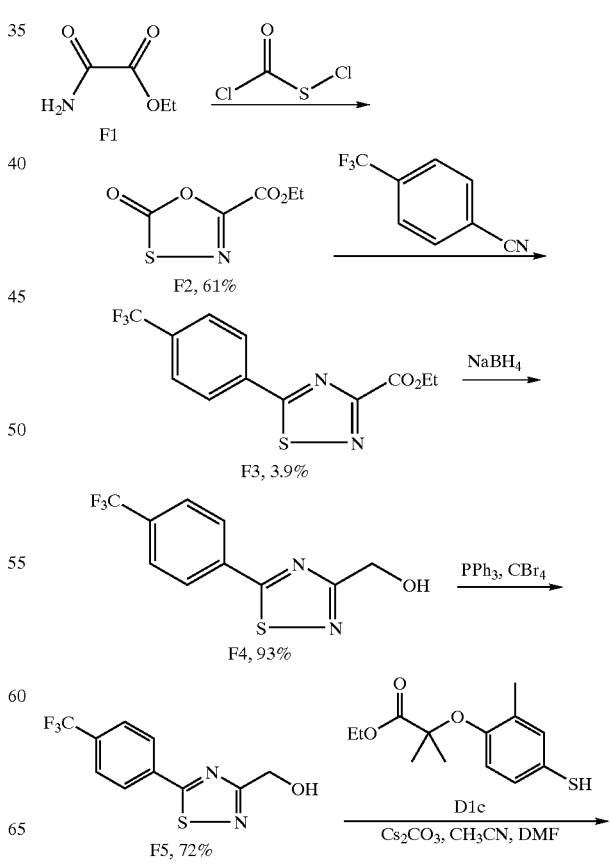

-continued

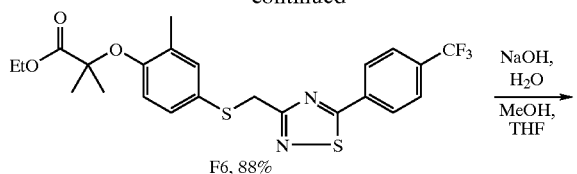
F6, 88%

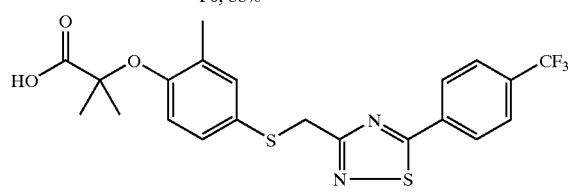
56%

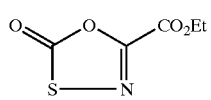
F2

2-Oxo-[1,3,4]oxathiazole-5-carboxylic acid ethyl ester

To a suspension of ethyl oxamate (8.80 g, 75.2 mmol) in toluene (75 mL) was added chlorocarbonylsulfenyl chloride (8.85 g, 67.5 mmol). The mixture was refluxed for 7 h and then stirred at room temperature overnight. The unreacted ethyl oxamate as white precipitate was filtered off and the filtrate was concentrated. The residue was dissolved in toluene, washed with saturated $NaHCO_3$ and brine, dried over $MgSO_4$, and concentrated to give 8.02 g (61%) of F2 as a light brown oil; $^1$H NMR (400 MHz, $CDCl_3$) δ 4.47 (q, J=7.1 Hz, 2 H), 1.43 (t, J=7.1 Hz, 3 H).

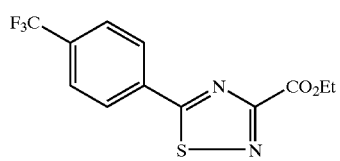

5-(4-Trifluoromethyl-phenyl)-[1,2,4]thiadiazole-3-carboxylic acid ethyl ester

A mixture of F2 (1.77 g, 10.1 mmol) and 4-trifluoromethylbenzonitrile (8.63 g, 50.5 mmol) in 1,2-dichlorobenzene (10 mL) was heated at 160° C. for 4 days. After cooling down to room temperature, the mixture was purified by column chromatography to provide 120 mg (3.9%) of F3 as light brown crystals; $^1$H NMR (300 MHz, $CDCl_3$) δ 8.17 (d, J=8.1 Hz, 2 H), 7.80 (d, J=8.2 Hz, 2 H), 4.56 (q, J=7.1 Hz, 2 H), 1.50 (t, J=7.1 Hz, 3 H); MS (ES) m/z: 303 (M+H$^+$).

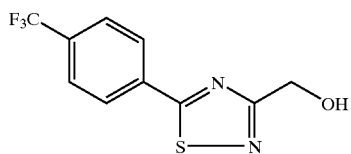
F4

[5-(4-Trifluoromethyl-phenyl)-[1,2,4]thiadiazol-3-yl]-methanol

Following the same procedure as in the preparation of A2d gave F4 (yellow solid, 93%); $^1$H NMR (300 MHz, $CDCl_3$) δ 8.09 (d, J=8.1 Hz, 2 H), 7.78 (d, J=8.2 Hz, 2 H), 5.01 (s, 2 H); MS (ES) m/z: 261 (M+H$^+$).

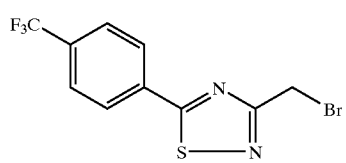
F5

3-Bromomethyl-5-(4-trifluoromethyl-phenyl)-[1,2,4]thiadiazole

Following the same procedure as in the preparation of D2d gave F5 (light yellow oil, 72%); $^1$H NMR (400 MHz, $CDCl_3$) δ 8.10 (d, J=8.2 Hz, 2 H), 7.78 (d, J=8.2 Hz, 2 H), 4.71 (s, 2 H); MS (ES) m/z: 323 (M+H$^+$).

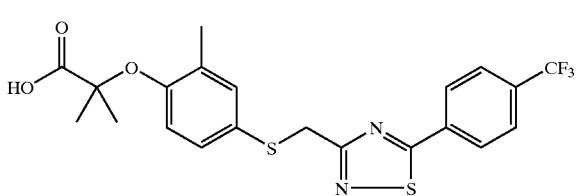
F6

2-Methyl-2-{2-methyl-4-[5-(4-trifluoromethyl-phenyl)-[1,2,4]thiadiazol-3-ylmethylsulfanyl]-phenoxy}-propionic acid ethyl ester Following the same procedure as in the preparation of D2e gave F6 (clear oil, 88%); $^1$H NMR (300 MHz, $CDCl_3$) δ 8.05 (d, J=8.1 Hz, 2 H), 7.76 (d, J=8.2 Hz, 2 H), 7.24 (d, J=1.9 Hz, 1 H), 7.11 (dd, J=8.5, 2.4 Hz, 1 H), 6.55 (d, J=8.5 Hz, 1 H), 4.34 (s, 2 H), 4.22 (q, J=7.1 Hz, 2 H), 2.17 (s, 3 H), 1.58 (s, 6 H), 1.22 (t, J=7.1 Hz, 3 H); MS (ES) m/z: 497 (M+H$^+$).

2-Methyl-2-{2-methyl-4-[5-(4-trifluoromethyl-phenyl)-[1,2,4]thiadiazol-3-ylmethylsulfanyl]-phenoxy}-propionic acid Compound 16 (56%); $^1$H NMR (300 MHz, $CDCl_3$) δ 8.05 (d, J=8.1 Hz, 2 H), 7.76 (d, J=8.2 Hz, 2 H), 7.28 (d, J=2.3 Hz, 1 H), 7.18 (dd, J=8.5, 2.3 Hz, 1 H), 6.73 (d, J=8.5 Hz, 1 H), 4.37 (s, 2 H), 2.19 (s, 3 H), 1.60 (s, 6 H); MS (ES) m/z: 469 (M+H$^+$). Anal. Calcd. For $C_{21}H_{19}F_3N_2O_3S_2$: C, 53.84; H, 4.09; N, 5.98. Found: C, 54.26; H, 4.12; N, 5.68.

Example 17

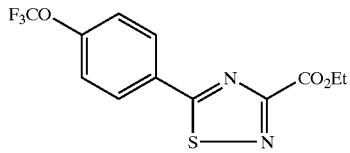

5-(4-Trifluoromethoxy-phenyl)-[1,2,4]thiadiazole-3-carboxylic acid ethyl ester

F7 (white solid, 34%); $^1$H NMR (300 MHz, CDCl$_3$) δ 8.10 (m, 2 H), 7.37 (d, J=8.0 Hz, 2 H), 4.55 (q, J=7.1 Hz, 2 H), 1.49 (t, J=7.1 Hz, 3 H); MS (ES) m/z: 319 (M+H$^+$).

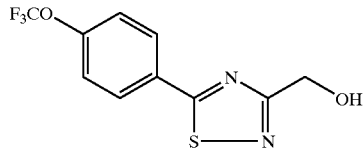

[5-(4-Trifluoromethoxy-phenyl)-[1,2,4]thiadiazol-3-yl]-methanol

F8 (white solid, 94%); $^1$H NMR (400 MHz, CDCl$_3$) δ 8.01 (m, 2 H), 7.35 (d, J=8.2 Hz, 2 H), 4.99 (s, 2 H), 2.70 (brs, 1 H).

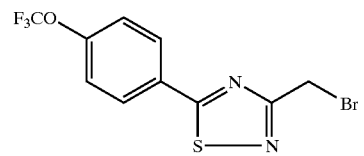

3-Bromomethyl-5-(4-trifluoromethoxy-phenyl)-[1,2,4]thiadiazole

F9 (clear oil, 87%); $^1$H NMR (300 MHz, CDCl$_3$) δ 8.02 (m, 2 H), 7.35 (d, J=8.1 Hz, 2 H), 4.69 (s, 2 H); MS (ES) m/z: 341 (M+H$^+$).

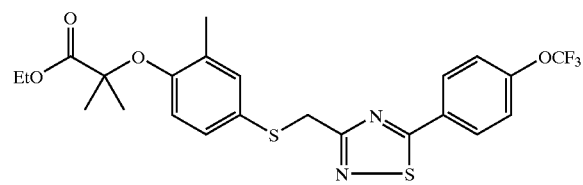

2-Methyl-2-{2-methyl-4-[5-(4-trifluoromethoxy-phenyl)-[1,2,4]thiadiazol-3-ylmethylsulfanyl]-phenoxy}-propionic acid ethyl ester F10 (clear oil, 92%); $^1$H NMR (300 MHz, CDCl$_3$) δ 7.97 (m, 2 H), 7.33 (d, J=8.1 Hz, 2 H), 7.24 (d, J=2.1 Hz, 1 H), 7.11 (dd, J=8.5, 2.3 Hz, 1 H), 6.55 (d, J=8.5 Hz, 1 H), 4.32 (s, 2 H), 4.22 (q, J=7.1 Hz, 2 H), 2.17 (s, 3 H), 1.57 (s, 6 H), 1.23 (t, J=7.1 Hz, 3 H); MS (ES) m/z: 513 (M+H$^+$).

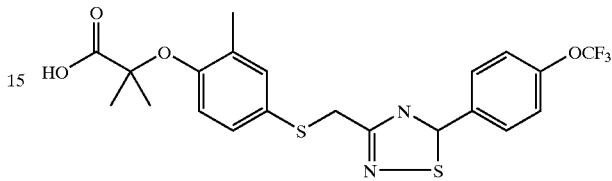

2-Methyl-2-{2-methyl-4-[5-(4-trifluoromethoxy-phenyl)-[1,2,4]thiadiazol-3-ylmethylsulfanyl]-phenoxy}-propionic acid Compound 17 (clear gummy material, 80%); $^1$H NMR (300 MHz, CDCl$_3$) δ 7.97 (m, 2 H), 7.33 (d, J=8.1 Hz, 2 H), 7.27 (s, 1 H), 7.17 (dd, J=8.5, 2.4 Hz, 1 H), 6.73 (d, J=8.5 Hz, 1 H), 4.35 (s, 2 H), 2.19 (s, 3 H), 1.60 (s, 6 H); MS (ES) m/z: 485 (M+H$^+$). Anal. Calcd. For C$_{21}$H$_{19}$F$_3$N$_2$O$_4$S$_2$: C, 52.06; H, 3.95; N, 5.78.
Found: C, 52.16; H, 3.70; N, 5.63.

Example 18

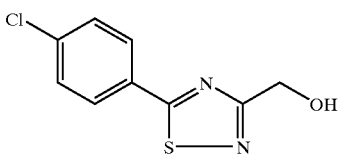

5-(4-Chloro-phenyl)-[1,2,4]thiadiazole-3-carboxylic acid ethyl ester

F11 (beige solid, 13%); $^1$H NMR (400 MHz, CDCl$_3$) δ 7.99 (d, J=8.6 Hz, 2 H), 7.51 (d, J=8.6 Hz, 2 H), 4.55 (q, J=7.1 Hz, 2 H), 1.49 (t, J=7.1 Hz, 3 H); MS (ES) m/z: 269 (M+H$^+$).

[5-(4-Chloro-phenyl)-[1,2,4]thiadiazol-3-yl]-methanol

F12 (97%); $^1$H NMR (400 MHz, CDCl$_3$) δ 7.91 (d, J=8.6 Hz, 2 H), 7.49 (d, J=8.6 Hz, 2 H), 4.98 (s, 2 H); MS (ES) m/z: 227 (M+H$^+$).

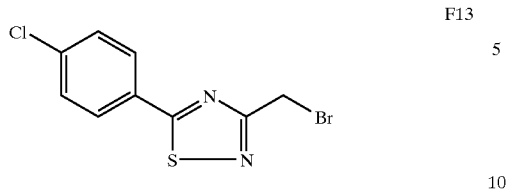

3-Bromomethyl-5-(4-chloro-phenyl)-[1,2,4]thiadiazole

F13 (white solid, 84%); $^1$H NMR (300 MHz, CDCl$_3$) δ 7.92 (d, J=8.6 Hz, 2 H), 7.49 (d, J=8.6 Hz, 2 H), 4.68 (s, 2 H); MS (ES) m/z: 289 (M+H$^+$).

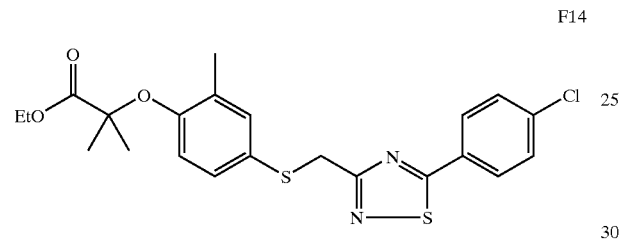

2-{4-[5-(4-Chloro-phenyl)-[1,2,4]thiadiazol-3-ylmethylsulfanyl]-2-methyl-phenoxy}-2-methyl-propionic acid ethyl ester F14 (clear oil, 83%); $^1$H NMR (300 MHz, CDCl$_3$) δ 7.87 (m, 2 H), 7.47 (m, 2 H), 7.24 (d, J=1.9 Hz, 1 H), 7.11 (dd, J=8.5, 2.3 Hz, 1 H), 6.55 (d, J=8.5 Hz, 1 H), 4.32 (s, 2 H), 4.22 (q, J=7.1 Hz, 2 H), 2.17 (s, 3 H), 1.58 (s, 6 H), 1.23 (t, J=7.1 Hz, 3 H); MS (ES) m/z: 463 (M+H$^+$).

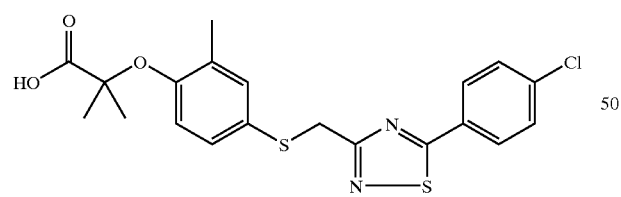

2-{4-[5-(4-Chloro-phenyl)-[1,2,4]thiadiazol-3-ylmethylsulfanyl]-2-methyl-phenoxy}-2-methyl-propionic acid Compound 18 (clear gummy material, 55%); $^1$H NMR (300 MHz, CDCl$_3$) δ 7.87 (m, 2 H), 7.47 (m, 2 H), 7.27 (m, 1 H), 7.18 (dd, J=8.4, 2.3 Hz, 1 H), 6.73 (d, J=8.5 Hz, 1 H), 4.34 (s, 2 H), 2.19 (s, 3 H), 1.60 (s, 6 H); MS (ES) m/z: 435 (M+H$^+$).

Example 19

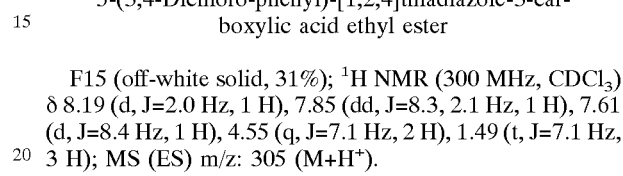

5-(3,4-Dichloro-phenyl)-[1,2,4]thiadiazole-3-carboxylic acid ethyl ester

F15 (off-white solid, 31%); $^1$H NMR (300 MHz, CDCl$_3$) δ 8.19 (d, J=2.0 Hz, 1 H), 7.85 (dd, J=8.3, 2.1 Hz, 1 H), 7.61 (d, J=8.4 Hz, 1 H), 4.55 (q, J=7.1 Hz, 2 H), 1.49 (t, J=7.1 Hz, 3 H); MS (ES) m/z: 305 (M+H$^+$).

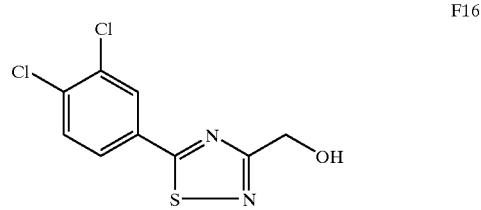

[5-(3,4-Dichloro-phenyl)-[1,2,4]thiadiazol-3-yl]-methanol

F16 (white solid, 84%); $^1$H NMR (300 MHz, CDCl$_3$) δ 8.09 (d, J=2.1 Hz, 1 H), 7.78 (dd, J=8.4, 2.1 Hz, 1 H), 7.59 (d, J=8.4 Hz, 1 H), 4.99 (s, 2 H); MS (ES) m/z: 261 (M+H$^+$).

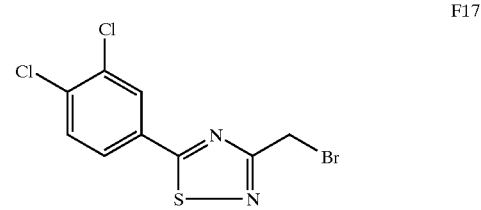

3-Bromomethyl-5-(3,4-dichloro-phenyl)-[1,2,4]thiadiazole

F17 (white solid, 83%); $^1$H NMR (300 MHz, CDCl$_3$) δ 8.03 (d, J=2.1 Hz, 1 H), 7.71 (dd, J=8.3, 2.1 Hz, 1 H), 7.52 (d, J=8.3 Hz, 1 H), 4.61 (s, 2 H); MS (ES) m/z: 349 (M+Na$^+$).

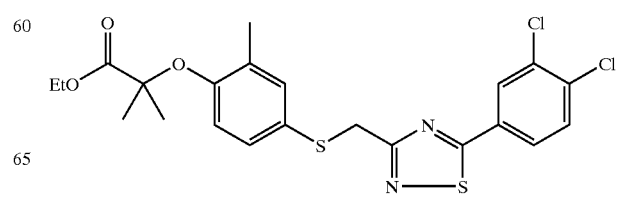

2-{4-[5-(3,4- Dichloro-phenyl)-[1,2,4]thiadiazol-3-ylmethylsulfanyl]-2-methyl-phenoxy}-2-methyl-propionic acid ethyl ester F18 (clear oil, 79%); ¹H NMR (300 MHz, CDCl₃) δ 8.06 (d, J=2.0 Hz, 1 H), 7.74 (dd, J=8.3, 2.1 Hz, 1 H), 7.57 (d, J=8.3 Hz, 1 H), 7.24 (d, J=1.9 Hz, 1 H), 7.10 (dd, J=8.5, 2.4 Hz, 1 H), 6.55 (d, J=8.5 Hz, 1 H), 4.32 (s, 2 H), 4.22 (q, J=7.1 Hz, 2 H), 2.18 (s, 3 H), 1.58 (s, 6 H), 1.23 (t, J=7.1 Hz, 3 H); MS (ES) m/z: 497 (M+H⁺).

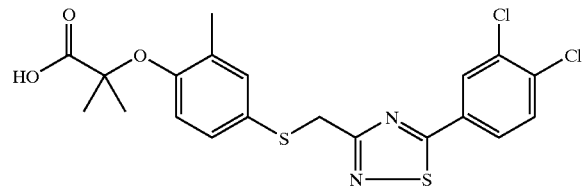

2-{4-[5-(3,4-Dichloro-phenyl)-[1,2,4]thiadiazol-3-ylmethylsulfanyl]-2-methyl-phenoxy}-2-methyl-propionic acid Compound 19 (white gummy material, 86%); ¹H NMR (400 MHz, CDCl₃) δ 8.06 (d, J=2.0 Hz, 1 H), 7.73 (dd, J=8.3, 2.0 Hz, 1 H), 7.57 (d, J=8.3 Hz, 1 H), 7.26 (m, 1 H), 7.16 (m, 1 H), 6.72 (d, J=8.4 Hz, 1 H), 4.34 (s, 2 H), 2.20 (s, 3 H), 1.60 (s, 6 H); MS (ES) m/z: 469 (M+H⁺). Anal. Calcd. For $C_{20}H_{18}Cl_2N_2O_3S_2$: C, 51.17; H, 3.87; N, 5.97. Found: C, 51.06; H, 3.68; N, 5.63.

Example 20

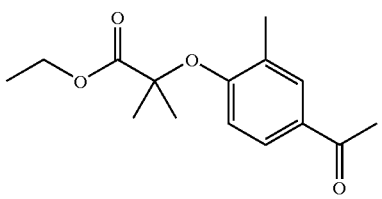

7-C 2-(4-Acetyl-2-methyl-phenoxy)-2-methyl-propionic acid ethyl ester

As shown in Scheme 7 hereinabove, mixture of compound 7-A (7.93 g, 40.65 mmol), 7-B (6.10 g, 40.65 mmol) and cesium carbonate (13.2 g, 40.65 mmol) was refluxed in dioxane (100 mL) for 18 h. After cooling, the mixture was partitioned between ethyl acetate and water. The organic layers were dried and concentrated. Purification by column chromatography (EtOAc/Hexane) gave compound 7-C (6.169 g, 57%) as a colorless oil: ¹HNMR(300 MHz, CDCl₃) δ 7.78 (d, J=.1.5 Hz, 1H), 7.67–7.70 (dd, J=2.1, 8.6 Hz, 1H), 6.60–6.63 (d, J=8.6 Hz, 1H), 4.19–4.26 (q, J=7.1 Hz, 2H), 2.53 (s, 3H), 2.27 (s, 3H), 1.66 (s, 6H), 1.24 (t, J=7.1 Hz, 3H); MS (ES) m/z: 265 (M+H⁺).

Example 21

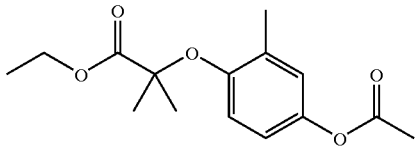

7-D 2-(4-Acetoxy-2-methyl-phenoxy)-2-methyl-propionic acid ethyl ester

Compound 7-C (2.14 g, 8.10 mmol) was dissolved in CH₂Cl₂ (25 mL). mCPBA (77 wt %, 3.18 g, 14.17 mmol) and TsOH monohydrate (154 mg, 0.81 mmol) were added. The mixture was stirred at refluxing for 4 h and cooled. Solid Na₂S₂O₃ was added, followed by saturated aqueous Na₂S₂O₃, NaHCO₃ and brine. The organic phase was dried and evaporated. Purification by column chromatography eluting with EtOAc/Hexane gave compound 7-D (1.858 g, 82%) as a light yellow oil: ¹HNMR (300 MHz, CDCl₃) δ 6.88 (d, J=2.8 Hz,1H), 6.74– 6.78 (dd, J=2.8, 8.8 Hz, 1H), 6.66 (d, J=8.8 Hz, 1H), 4.20–4.27 (q, J=7.1 Hz, 2H), 2.26 (s, 3H), 2.22 (s, 3H), 1.58 (s, 6H), 1.23–1.27 (t, J=7.1 Hz, 3H); MS (ES) m/z: 298 (M+H⁺).

Example 22

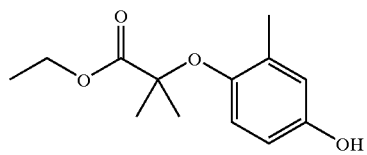

7-E 2-(4-Hydroxy-2-methyl-phenoxy)-2-methyl-propionic acid ethyl ester

Compound 7-D (1.858 g, 6.63 mmol) was mixed with THF (10 mL). NaOEt in EtOH (2.68 M, 6.63 mmol) was added. The mixture was stirred at r.t. for 2 h and concentrated. The residue was partitioned between EtOAc and H₂O. The organic phase was dried and concentrated. Purification by column chromatography eluting with EtOAc/Hexane provided compound 7-E (1.28 g, 81%) as a light yellow oil: ¹HNMR (300 MHz, CDCl₃) δ 6.62–6.65 (m, 2H), 6.48–6.52 (dd, J=3.0, 8.7 Hz, 1H), 4.51 (s,1H), 4.22–4.29 (q, J=7.1 Hz, 2H), 2.19 (s, 3H), 1.53 (s, 6H), 1.26–1.30 (t, J=7.1 Hz, 3H); MS (ES) m/z: 261 (M+Na)

Example 23

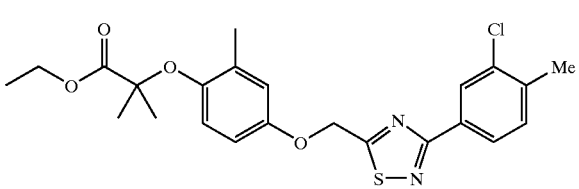

7F1

2-{4-[3-(3-Chloro-4-methyl-phenyl)-[1,2,4]thiadiazol-5-ylmethoxy]-2-methyl-phenoxy}-2-methyl-propionic acid ethyl ester Compound 7-E (124 mg, 0.521 mmol) and compound D39 (157 mg, 0.521 mmol) were mixed with MeCN. After adding cesium carbonate (340 mg, 1.04 mmol), the mixture was stirred at r.t. for 2 h and then partitioned between EtOAc and water. The organic phase was dried and evaporated. The residue was purified by column chromatography eluting with EtOAc/Hexane to give compound 7F1 (198 mg, 83%) as a white solid: $^1$HNMR (400 MHz, CDCl$_3$) δ 8.29 (d, J=1.6 Hz, 1H), 8.06–8.08 (dd, J=1.6, 7.9 Hz, 1H), 7.34 (d, J=7.9 Hz, 1H), 6.85 (s, 1 H), 6.71 (s, 2H), 5.44 (s, 2H), 4.23–4.28 (q, J=7.1 Hz, 2H), 2.44 (s, 3H), 2.24 (s, 3H), 1.55 (s, 6H), 1.26–1.30 (t, J=7.1 Hz, 3H); MS (ES) m/z: 461 (M+H$^+$).

Example 24

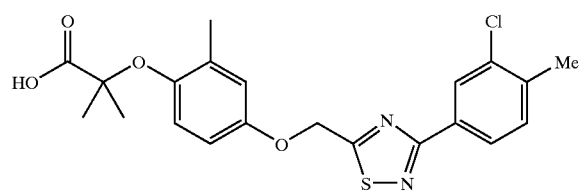

7G1

2-{4-[3-(3-Chloro-4-methyl-phenyl)-[1,2,4]thiadiazol-5-ylmethoxy]-2-methyl-phenoxy}-2-methyl-propionic acid To a solution of compound 7F1 (183 mg, 0.398 mmol) in THF (2.0 mL) and MeOH (1.0 mL) was added 2N NaOH. The resulting red solution was stirred at r.t. for 5.5 h and then acidified with 1 N HCl. The mixture was extracted with EtOAc and the organic extracts were dried and concentrated. Purification with column chromatography eluting with CH$_2$Cl$_2$/MeOH provided compound 7G1 (compound 20, 71 mg, 41%) as a light yellow solid: $^1$HNMR (400 MHz, CD$_3$OD) δ 6.72 (s, 1H), 6.57 (d, J=7.9 Hz, 1H), 5.89 (d, J=7.7 Hz, 1H), 5.40 (s, 1H), 5.26–5.33 (m, 2H), 4.0 (d, J=1.5 Hz, 2H), 1.77 (s, 6H), 0.90 (s, 3H), 0.70 (s, 3H); MS (ES) m/z: 433 (M+H$^+$). Anal. Calcd. for C$_{21}$H$_{21}$ClN$_2$O$_4$S: C, 58.26; H, 4.89; N, 6.47; Found: C, 57.85, H, 4.86; N, 6.46.

Example 25

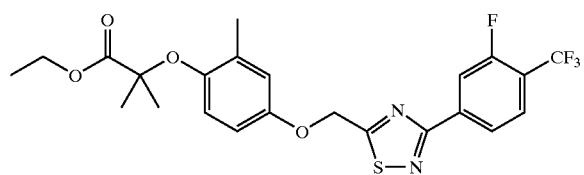

7F2

2-{4-[3-(3-Fluoro-4-trifluoromethyl-phenyl)-[1,2,4]thiadiazol-5-ylmethoxy]-2-methyl-phenoxy}-2-methyl-propionic acid ethyl ester Compound 7F2 was prepared following the same procedure as described for compound 7F1 (78%) as a colorless oil. $^1$HNMR (300 MHz, CDCl$_3$) δ 8.12–8.20 (m, 2H), 7.69–7.75 (t, J=6.6 Hz, 1H), 6.86 (s,1H), 6.71 (s, 2H), 5.4 (s, 2H), 4.22–4.29 (q, J=7.1 Hz, 2H), 2.25 (s, 3H), 1.56 (s, 6H), 1.25–1.30 (t, J=7.1 Hz, 3H); MS(ES) m/z: 499 (M+H$^+$).

Example 26

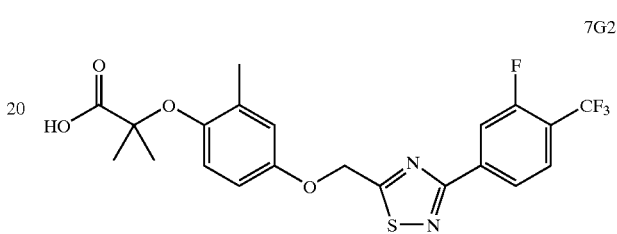

7G2

2-{4-[3-(3-Fluoro-4-trifluoromethyl-phenyl)-[1,2,4]thiadiazol-5-ylmethoxy]-2-methyl-phenoxy}-2-methyl-propionic acid Compound 7G2 (compound 21) was prepared following the same procedure as described for compound 7G1 (78%) as a colorless oil: $^1$HNMR (400 MHz, DMSO-d$_6$) δ 8.18–8.26 (m, 2H), 7.99–8.03 (t, J=7.9 Hz, 1H), 7.00 (d, J=3.0 Hz, 1H), 6.87–6.90 (m, 1H), 6.74 (d, J=8.9 Hz, 1H), 5.66 (s, 2H), 2.17 (s, 3H), 1.46 (s, 6H); MS (ES) m/z: 471 (M+H$^+$), 469 (M−H$^+$); HRMS for C$_{21}$H$_{18}$F$_4$N$_2$O$_4$S: Found 470.0914 (calcd. 470.0923).

Example 27

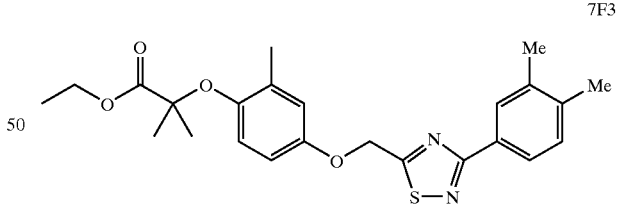

7F3

2-{4-[3-(3,4-Dimethyl-phenyl)-[1,2,4]thiadiazol-5-ylmethoxy]-2-methyl-ethyl-phenoxy}-2-methyl-propionic acid ethyl ester Compound 7F3 was prepared according to the procedure used for compound 7F1 (77%) as a white solid: $^1$HNMR (300 MHz, CDCl$_3$) δ 8.07 (s,1H), 8.01 (d, J=7.9 Hz, 1H), 7.23 (s, 1H), 6.85 (s, 1H), 6.70 (d, J=1.3 Hz, 2H), 5.45 (s, 2H), 4.22–4.29 (q, J=7.1 Hz, 2H), 2.34 (d, J=7.1 Hz, 6H), 2.24 (s, 3H), 1.53 (s, 6H), 1.25–1.30 (t, J=7.1 Hz, 3H); MS(ES) m/z: 441 (M+H$^+$).

Example 28

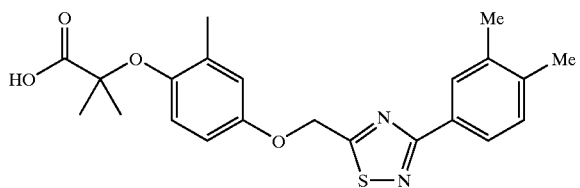

2-{4-[3-(3,4-Dimethyl-phenyl)-[1,2,4]thiadiazol-5-ylmethoxy]-2-methyl-phenoxy}-2-methyl-propionic acid Compound 7G3 (compound 22) was prepared according to the procedure used for compound 7G1 (24%) as a white solid: $^1$HNMR (300 MHz, CDCl$_3$) δ 8.07 (s, 1 H), 8.02 (d, J=7.7 Hz, 1H), 7.23 (s, 1 H), 6.85–6.91 (m, 2H), 6.75–6.79 (dd, J=3.2, 8.7 Hz, 1H), 5.48 (s, 2H), 2.34 (d, J=7.0 Hz, 6H), 2.26 (s, 3H), 1.57 (s, 6H); MS (ES) m/z: 411 (M−H$^+$), 413 (M+H$^+$); HRMS (M+H$^+$ for $C_{22}H_{24}N_2O_4S$: 413.1533 (calcd. 413.1535).

Example 29

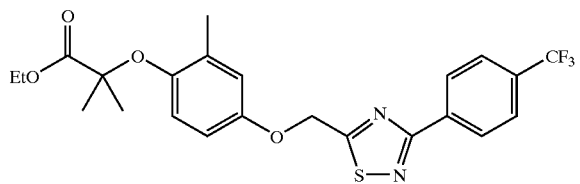

2-Methyl-2-{2-methyl-4-[3-(4-trifluoromethyl-phenyl)-[1,2,4]thiadiazol-5-ylmethoxy]-phenoxy}-propionic acid ethyl ester Compound 7F4 was prepared following the same procedure as described for compound 7F1 (72%) as a white solid; $^1$H NMR (300 MHz, CDCl$_3$) δ 8.39 (d, J=8.1 Hz, 2 H), 7.73 (d, J=8.2 Hz, 2 H), 6.88 (s, 1 H), 6.70 (s, 2 H), 5.45 (s, 2 H), 4.25 (q, J=7.1 Hz, 2 H), 2.24 (s, 3 H), 1.56 (s, 6 H), 1.28 (t, J=7.1 Hz, 3 H; MS (ES) m/z: 481 (M+H$^+$).

Example 30

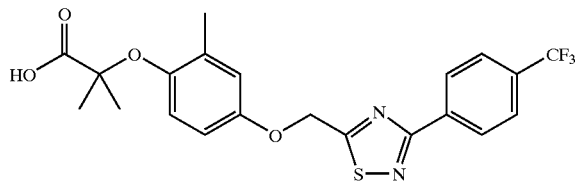

2-Methyl-2-{2-methyl-4-[3-(4-trifluoromethyl-phenyl)-[1,2,4]thiadiazol-5-ylmethoxy]-phenoxy}-propionic acid Compound 7G4 (compound 23) was prepared following the same procedure as described for compound 7G1 (99%) as a white solid; $^1$H NMR (300 MHz, MeOH-d$_4$) δ 8.48 (d, J=8.2 Hz, 2 H), 7.81 (d, J=8.3 Hz, 2 H), 6.95 (s, 1 H), 6.83 (s, 2 H), 5.56 (s, 2 H), 2.23 (s, 3 H), 1.54 (s, 6 H); MS (ES) m/z: 453 (M+H$^+$). Anal. Calcd. For $C_{21}H_{19}F_3N_2O_4S$: C, 55.75; H, 4.23; N, 6.19. Found: C, 55.57; H, 4.00; N, 6.03.

Example 31

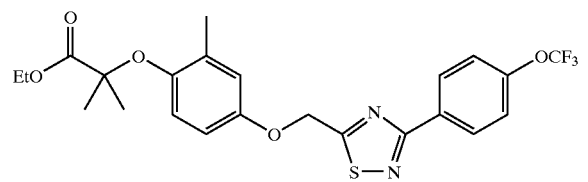

2-Methyl-2-{2-methyl-4-[3-(4-trifluoromethoxy-phenyl)-[1,2,4]thiadiazol-5-ylmethoxy]-phenoxy}-propionic acid ethyl ester Compound 7F5 was prepared following the same procedure as described for compound 7F1 (92%, white crystalline solid); $^1$H NMR (300 MHz, CDCl$_3$) δ 8.33 (d, J=8.9 Hz, 2 H), 7.32 (d, J=8.1 Hz, 2 H), 6.85 (s, 1 H), 6.71 (s, 2 H), 5.45 (s, 2 H), 4.25 (q, J=7.1 Hz, 2 H), 2.24 (s, 3 H), 1.56 (s, 6 H), 1.28 (t, J=7.1 Hz, 3 H); MS (ES) m/z: 497 (M+H$^+$).

Example 32

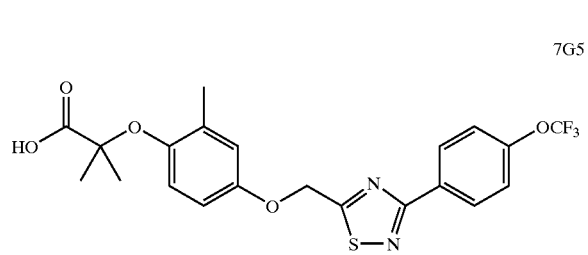

2-Methyl-2-{2-methyl-4-[3-(4-trifluoromethoxy-phenyl)-[1,2,4]thiadiazol-5-ylmethoxy]-phenoxy}-propionic acid Compound 7G5 (compound 24) was prepared following the same procedure as described for compound 7G1 (78%, white crystalline solid); $^1$H NMR (300 MHz, CD$_3$OD) δ 8.39 (d, J=8.8 Hz, 2 H), 7.41 (d, J=8.4 Hz, 2 H), 6.94 (d, J=2.5 Hz, 1 H), 6.83 (m, 2 H), 5.54 (s, 2 H), 2.23 (s, 3 H), 1.53 (s, 6 H); MS (ES) m/z: 469 (M+H$^+$). Anal. Calcd. For $C_{21}H_{19}F_3N_2O_5S$: C, 53.84; H, 4.09; N, 5.98. Found: C, 53.69; H, 3.91; N, 5.82.

Example 33

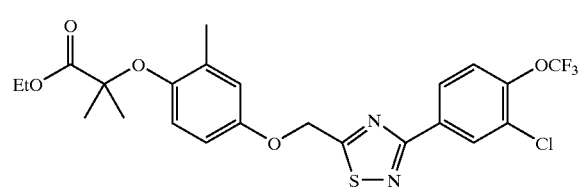

2-{4-[3-(3-Chloro-4-trifluoromethoxy-phenyl)-[1,2,4]thiadiazol-5-ylmethoxy]-2-methyl-phenoxy}-2-methyl-propionic acid ethyl ester Compound 7F6 was prepared following the same procedure as described for compound 7F1 (90%, white crystalline solid); $^1$H NMR (300 MHz, CDCl$_3$) δ 8.41 (d, J=2.0 Hz, 1 H), 8.19 (dd, J=8.6, 2.1 Hz, 1 H), 7.40 (d, J=8.6, 1 H), 6.81 (s, 1 H), 6.70 (s, 2 H), 5.41 (s, 2 H), 4.25 (q, J=7.1 Hz, 2 H), 2.26 (s, 3 H), 1.55 (s, 6 H), 1.28 (t, J=7.1 Hz, 3 H); MS (ES) m/z: 531 (M+H$^+$).

Example 34

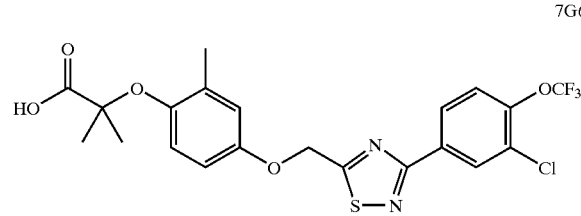

7G6

2-Methyl-2-{2-methyl-4-[3-(4-trifluoromethoxy-phenyl)-[1,2,4]thiadiazol-5-ylmethoxy]-phenoxy}-propionic acid Compound 7G6 (compound 25) was prepared following the same procedure as described for compound 7G1 (88%, white crystalline solid); $^1$H NMR (300 MHz, CD$_3$OD) δ 8.47 (d, J=2.0 Hz, 1 H), 8.32 (dd, J=8.6, 2.1 Hz, 1 H), 7.58 (dd, J=8.6, 1.4 Hz, 1 H), 6.94 (s, 1 H), 6.83–6.82 (m, 2 H), 5.55 (s, 2 H), 2.23 (s, 3 H), 1.53 (s, 6 H); MS (ES) m/z: 503 (M+H$^+$). Anal. Calcd. For C$_{21}$H$_{18}$ClF$_3$N$_2$O$_5$S: C, 50.16; H, 3.61; N, 5.57. Found: C, 50.16; H, 3.33; N, 5.43.

Example 35

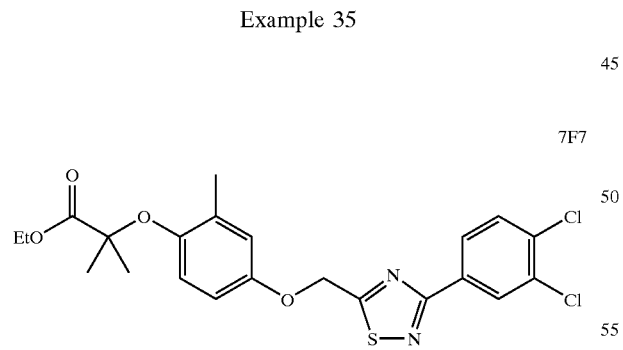

7F7

2-{4-[3-(3,4-Dichloro-phenyl)-[1,2,4]thiadiazol-5-ylmethoxy]-2-methyl-phenoxy}-2-methyl-propionic acid ethyl ester Compound 7F7 was prepared following the same procedure as described for compound 7F1 (76%, white crystalline solid); $^1$H NMR (300 MHz, CDCl$_3$) δ 8.40 (d, J=2.0 Hz, 1 H), 8.11 (dd, J=8.4, 2.1 Hz, 1 H), 7.53 (d, J=8.4 Hz, 1 H), 6.85 (s, 1 H), 6.71 (m, 2 H), 5.42 (s, 2 H), 4.22 (q, J=7.1 Hz, 2 H), 2.23 (s, 3 H), 1.55 (s, 6 H); MS (ES) m/z: 481 (M+H$^+$).

Example 36

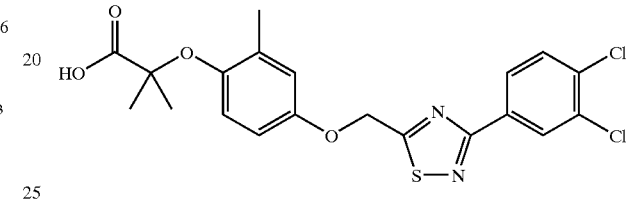

7G7

2-{4-[3-(3,4-Dichloro-phenyl)-[1,2,4]thiadiazol-5-ylmethoxy]-2-methyl-phenoxy}-2-methyl-propionic acid Compound 7G7 (compound 27) was prepared following the same procedure as described for compound 7G1 (35%, white crystalline solid); $^1$H NMR (300 MHz, CD$_3$OD) δ 8.40 (s, 1 H), 8.19 (d, J=8.4 Hz, 1 H), 7.66 (d, J=8.4 Hz, 1 H), 6.92 (d, J=2.6 Hz, 1 H), 6.87 (d, J=8.5 Hz, 1 H), 6.79 (d, J=8.4 Hz, 1 H), 5.53 (s, 2 H), 2.23 (s, 3 H), 1.52 (s, 6 H); MS (ES) m/z: 453 (M+H$^+$).

Example 37

8E 2-(4-{2-[3-(3,4-Dichloro-phenyl)-[1,2,4]thiadiazol-5-yl]-ethylsulfanyl}-2-methyl-phenoxy)-2-methyl-propionic acid

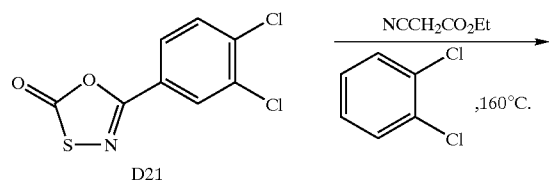

D21

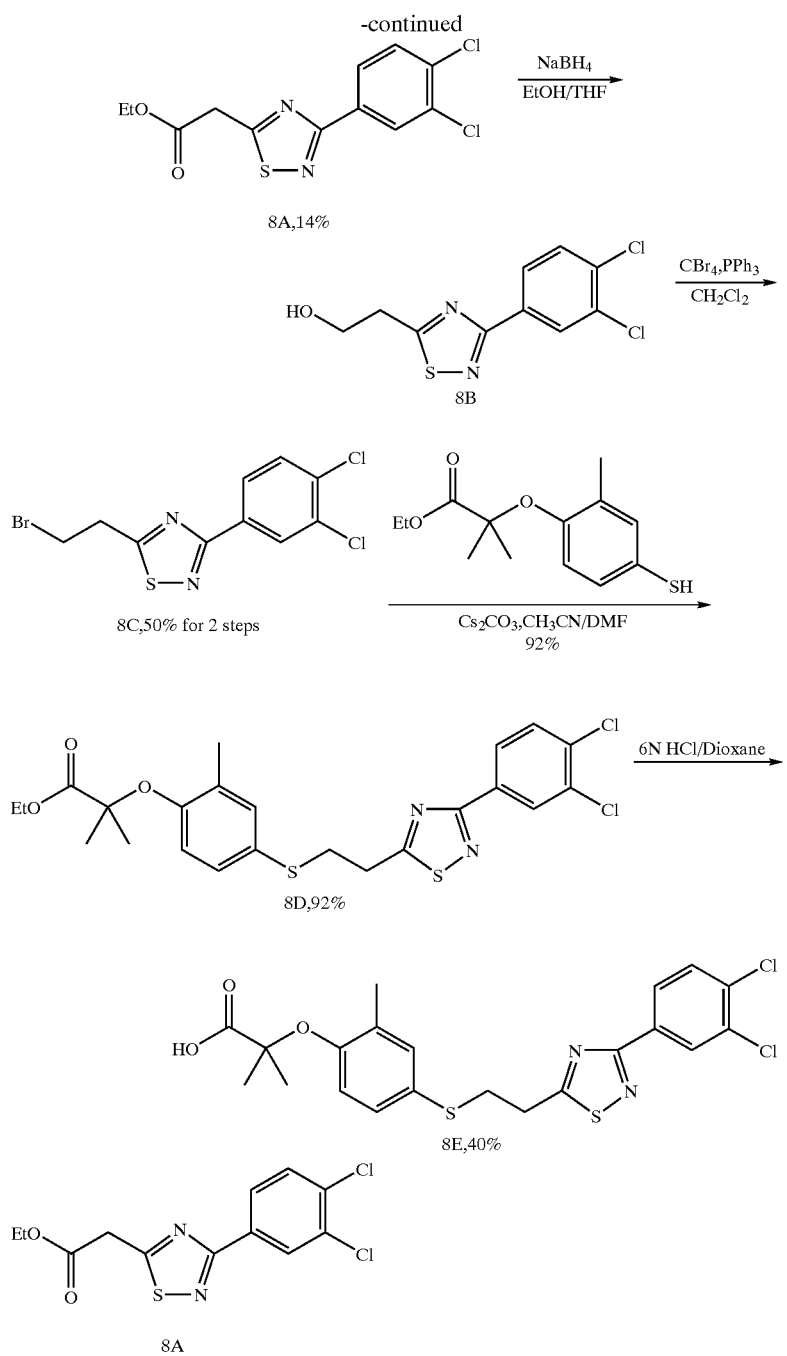

[3-(3,4-Dichloro-phenyl)-[1,2,4]thiadiazol-5-yl]-acetic acid ethyl ester

A reaction mixture of D21 (1 g, 4.03 mmol) and ethyl cyanoacetate (1.8 g, 16.1 mmol) in 1,2-dichlorobenzene (18 mL) was heated at 160° C. for 20 h. After cooling down to room temperature, the reaction mixture was purified by column chromatography to give 180 mg (14%) of 8A as a white solid; $^1$H NMR (300 MHz, CDCl$_3$) δ 8.39 (d, J=1.9 Hz, 1 H), 8.11 (dd, J=8.4 Hz, 2.0 Hz, 1 H), 7.53 (d, J=8.4 Hz, 1 H), 4.33 (q, J=7.1 Hz, 2 H), 4.25 (s, 2H), 1.36 (t, J=7.1 Hz, 3 H); MS (ES) m/z: 317 (M+H$^+$).

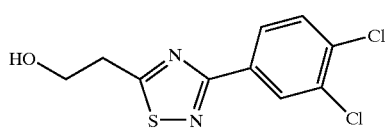

2-[3-(3,4-Dichloro-phenyl)-[1,2,4]thiadiazol-5-yl]-ethanol

To a solution of 8A (180 mg, 0.57 mmol) in EtOH-THF (8 mL–2 mL) at room temperature was added NaBH$_4$ (136 mg, 3.6 mmol). After stirring for 20 h, a few drops of water were added to quench excess of hydride. The solvent was evaporated, and the residue was partitioned between CH$_2$Cl$_2$ and water. The organic phase was dried and concentrated. The crude mixture was purified by column chromatography to provide 100 mg (64%) of 8B as a white solid; $^1$H NMR (300 MHz, CDCl$_3$) δ 8.39 (d, J=2.0 Hz, 1 H), 8.11 (dd, J=8.4 Hz, 2.0 Hz, 1 H), 4.11 (t, J=5.6 Hz, 2 H), 3.41 (t, J=5.6 Hz, 2 H).

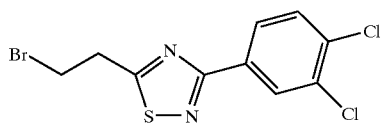

5-(2-Bromo-ethyl)-3-(3,4-dichloro-phenyl)-[1,2,4]thiadiazole

To a solution of 8B (100 mg, 0.36 mmol) in CH$_2$Cl$_2$ (4 mL) at 0° C. was added CBr$_4$ (157 mg, 0.47 mmol) and PPh$_4$ (124 mg, 0.47 mmol). After stirring at room temperature for 20 h, the solvent was evaporated, and the residue was purified by column chromatography to provide 106 mg (86%) of 8C as a white solid; $^1$H NMR (300 MHz, CDCl$_3$) δ 8.39 (d, J=2.0 Hz, 1 H), 8.11 (dd, J=8.4 Hz, 2.0 Hz, 1 H), 3.83–3.78 (m, 2 H), 3.73–3.69 (m, 2 H).

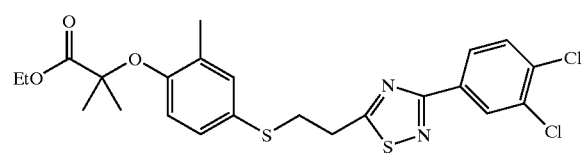

2-(4-{2-[3-(3,4-Dichloro-phenyl)-[1,2,4]thiadiazol-5-yl]-ethylsulfanyl}-2-methyl-phenoxy)-2-methyl-propionic acid ethyl ester A mixture of 8C (106 mg, 0.314 mmol) and (4-mercapto-2-methyl-phenoxy)acetic acid ethyl ester A1c (84 mg, 0.330 mmol) in CH$_3$CN (4 mL) was added Cs$_2$CO$_3$ (154 mg, 0.472 mmol), the mixture was stirred 1 h under N$_2$, concentrated, and purified by column chromatography (EtOAc/hexane) to give 140 mg (87%) of 8D as a white solid; $^1$H NMR (300 MHz, CDCl$_3$) δ 8.37 (d, J=2.0 Hz, 1 H), 8.10 (dd, J=8.4 Hz, 2.0 Hz, 1 H), 7.53 (d, J=8.4 Hz, 1 H), 7.26 (s, 1 H), 7.15 (dd, J=8.5 Hz, 2.1 Hz, 1 H), 6.60 (d, J=8.5 Hz, 1 H), 4.23 (q, J=7.1, 2 H), 3.37 (t, J=6.4 Hz, 2 H), 3.26 (t, J=6.3 Hz, 2 H), 2.21 (s, 3 H), 1.60 (s, 6 H), 1.24 (t, J=7.1 Hz, 3 H); MS (ES) m/z: 511 (M+H$^+$).

2-(4-{2-[3-(3,4-Dichloro-phenyl)-[1,2,4]thiadiazol-5-yl]-ethylsulfanyl}-2-methyl-phenoxy)-2-methyl-propionic acid A mixture of 8D (37 mg, 0.072 mmol) and 6 N HCl (2 mL) in 1,4-dioxane (1 mL) was heated at 100° C. for 24 h. After cooling down, the reaction mixture was extracted with ether (5 mL×3). The combined organic layers were dried, concentrated and purified by column chromatography to give 20 mg (40%) of the target compound 8E (compound 27) as a white solid; $^1$H NMR (300 MHz, CD$_3$OD) δ 8.29 (d, J=1.9 Hz, 1 H), 8.07 (dd, J=8.4 Hz, 1.9 Hz, 1 H), 7.58 (d, J=8.4 Hz, 1 H), 7.23 (d, J=1.8 Hz, 1 H), 7.15 (dd, J=8.3 Hz, 1.9 Hz, 1 H), 6.70 (d, J=8.4 Hz, 1 H), 3.38 (t, J=6.0 Hz, 2 H), 3.31 (m, 2 H), 2.15 (s, 3 H), 1.56 (s, 6 H); MS (ES) m/z: 483 (M+H$^+$). HRMS/z calcd for C$_{21}$H$_{20}$OCl$_2$N$_2$O$_3$S$_2$: 482.029; found: 482.0302.

Example 38

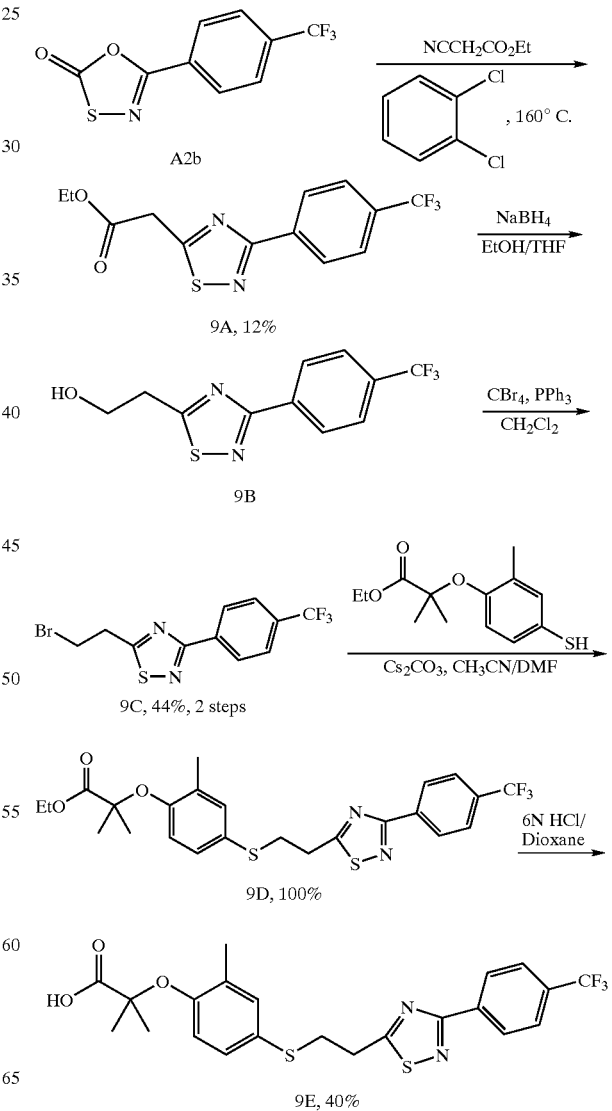

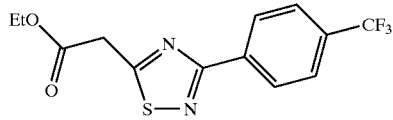

[3-(4-Trifluoromethyl-phenyl)-[1,2,4]thiadiazol-5-yl]-acetic acid ethyl ester Replacing D21 with A2b and following the same procedure as in the preparation of 8A gave 9A (12%, white crystalline solid); $^1$H NMR (300 MHz, CDCl$_3$) δ 8.41 (d, J=8.1 Hz, 2 H), 7.73 (d, J=8.2 Hz, 2 H), 4.34 (q, J=7.2 Hz, 2 H), 4.27 (s, 2H), 1.37 (t, J=7.1 Hz, 3 H); MS (ES) m/z: 317 (M+H$^+$).

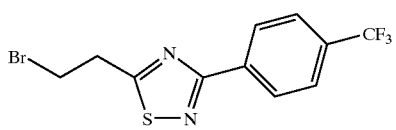

5-(2-Bromo-ethyl)-3-(4-trifluoromethyl-phenyl)-[1,2,4]thiadiazole

To a solution of 8A (220 mg, 0.696 mmol) in EtOH-THF (3 mL–2 mL) at room temperature was added NaBH$_4$ (136 mg, 3.6 mmol). After stirring for 20 h, a few drops of water were added to quench excess of hydride. The solvent was evaporated, and the residue was partitioned between CH$_2$Cl$_2$ and water. The organic phase was dried and concentrated to provide 190 mg crude alcohol.

To a solution of the above crude intermediate in CH$_2$Cl$_2$ (4 mL) at 0° C. was added CBr$_4$ (299 mg, 0.901 mmol) and PPh$_4$ (236 mg, 0.901 mmol). After stirring at room temperature for 20 h, the solvent was evaporated, and the residue was purified by column chromatography to provide 100 mg (44%, 2 steps) 9C as a white solid; $^1$H NMR (300 MHz, CDCl$_3$) δ 8.42 (d, J=8.1 Hz, 2 H), 7.74 (d, J=8.2 Hz, 2 H), 3.84–3.80 (m, 2 H), 3.76–3.71 (m, 2 H).

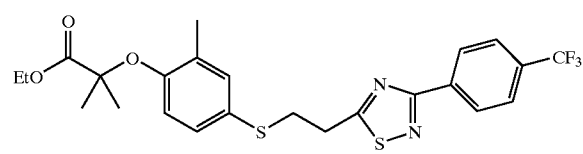

2-Methyl-2-(2-methyl-4-{2-[3-(4-trifluoromethyl-phenyl)-[1,2,4]thiadiazol-5-yl]-ethylsulfanyl}-phenoxy)-propionic acid ethyl ester Replacing 8D with 9C and following the same procedure as in the preparation of 8E gave 9D (100%, white solid); $^1$H NMR (300 MHz, CDCl$_3$) δ 8.39 (d, J=8.1 Hz, 2 H), 7.73 (d, J=8.2 Hz, 2 H), 7.28 (s, 1 H), 7.16 (dd, J=8.5 Hz, 2.1 Hz, 1 H), 6.59 (d, J=8.5 Hz, 1 H), 4.23 (q, J=7.1, 2 H), 3.40 (t, J=6.4 Hz, 2 H), 3.28 (t, J=6.4 Hz, 2 H), 2.20 (s, 3 H), 1.59 (s, 6 H), 1.22 (t, J=7.1 Hz, 3 H); MS (ES) m/z: 511 (M+H$^+$).

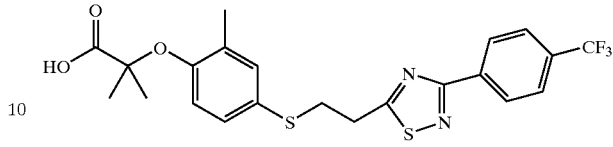

2-Methyl-2-(2-methyl-4-{2-[3-(4-trifluoromethyl-phenyl)-[1,2,4]thiadiazol-5-yl]-ethylsulfanyl}-phenoxy)-propionic acid Replacing 8D with 9D and following the same procedure as in the preparation of 8E gave 9E (compound 28, 40%, white solid); $^1$H NMR (300 MHz, CD$_3$OD) δ 8.42 (d, J=8.1 Hz, 2 H), 7.78 (d, J=8.2 Hz, 2 H), 7.23 (d, J=1.8 Hz, 1 H), 7.17 (d, J=8.3 Hz, 1 H), 6.76 (d, J=8.4 Hz, 1 H), 3.43 (t, J=6.1 Hz, 2 H), 3.30 (m, 2 H), 2.16 (s, 3 H), 1.54 (s, 6 H); MS (ES) m/z: 481 (M–H$^+$). HRMS/z calcd for C$_{21}$H$_{20}$Cl$_2$N$_2$O$_3$S$_2$: 482.0946; found: 482.0952.

D. Formulation and Administration

The present compounds are PPAR delta agonists and are therefore useful in treating or inhibiting the progression of PPAR delta mediated conditions, such as diabetes, cardiovascular diseases, Metabolic X Syndrome, hypercholesterolemia, hypo-HDL-cholesterolemia, hyper-LDL-cholesterolemia, dyslipidemia, atherosclerosis, obesity, and complications thereof. For instance, complications of diabetes include such conditions as neuropathy, nephropathy, and retinopathy.

The invention features a method for treating a subject with a PPAR delta mediated disease, said method comprising administering to the subject a therapeutically effective amount of a pharmaceutical composition comprising a compound of the invention. The invention also provides a method for treating or inhibiting the progression of diabetes or impaired glucose tolerance in a subject, wherein the method comprises administering to the subject a therapeutically effective amount of a pharmaceutical composition comprising a compound of the invention.

The compounds of the present invention may be formulated into various pharmaceutical forms for administration purposes. To prepare these pharmaceutical compositions, an effective amount of a particular compound, in base or acid addition salt form, as the active ingredient is intimately mixed with a pharmaceutically acceptable carrier.

A carrier may take a wide variety of forms depending on the form of preparation desired for administration. These pharmaceutical compositions are desirably in unitary dosage form suitable, preferably, for oral administration or parenteral injection. For example, in preparing the compositions in oral dosage form, any of the usual pharmaceutical media may be employed. These include water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. In view of their ease in administration, tablets and capsules represent the most advantageous oral dosage unit form, in which case solid pharmaceutical carriers are generally employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Such additives may facilitate the administration to the skin and/or may be helpful for preparing the desired compositions. These compositions may be administered in various ways, e.g., as a transdermal patch, as a spot-on, as an ointment. Acid addition salts of the compounds of formula I, due to their increased water solubility over the corresponding base form, are more suitable in the preparation of aqueous compositions.

It is especially advantageous to formulate the aforementioned pharmaceutical compositions in dosage unit form for ease of administration and uniformity of dosage. Dosage unit form as used in the specification herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Pharmaceutically acceptable acid addition salts include the therapeutically active non-toxic acid addition salts of disclosed compounds. The latter can conveniently be obtained by treating the base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, palmoic and the like acids. The term addition salt also comprises the solvates which the disclosed compounds, as well as the salts thereof, are able to form. Such solvates are for example hydrates, alcoholates and the like. Conversely the salt form can be converted by treatment with alkali into the free base form.

Stereoisomeric forms define all the possible isomeric forms which the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the (R)- or (S)-configuration; substituents on bivalent cyclic saturated radicals may have either the cis- or trans-configuration. The invention encompasses stereochemically isomeric forms including diastereoisomers, as well as mixtures thereof in any proportion of the disclosed compounds. The disclosed compounds may also exist in their tautomeric forms. Such forms although not explicitly indicated in the above and following formulae are intended to be included within the scope of the present invention.

Those of skill in the treatment of disorders or conditions mediated by the PPAR delta could easily determine the effective daily amount from the test results presented hereinafter and other information. In general it is contemplated that a therapeutically effective dose would be from 0.001 mg/kg to 5 mg/kg body weight, more preferably from 0.01 mg/kg to 0.5 mg/kg body weight. It may be appropriate to administer the therapeutically effective dose as two, three, four or more sub-doses at appropriate intervals throughout the day. Said sub-doses may be formulated as unit dosage forms, for example, containing 0.05 mg to 250 mg or 750 mg, and in particular 0.5 to 50 mg of active ingredient per unit dosage form. Examples include 2 mg, 4 mg, 7 mg, 10 mg, 15 mg, 25 mg, and 35 mg dosage forms. Compounds of the invention may also be prepared in time-release or subcutaneous or transdermal patch formulations. Disclosed compound may also be, formulated as a spray or other topical or inhalable formulations.

The exact dosage and frequency of administration depends on the particular compound of Formula (I) used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines.

The next section includes detailed information relating to the use of the disclosed compounds and compositions.

E. Use

The compounds of the present invention are pharmaceutically active, for example, as PPAR delta agonists and preferably as PPAR alpha/delta dual agonists. According to one aspect of the invention, the compounds are preferably selective PPAR delta agonists, having an activity index (e.g., PPAR delta potency over PPAR alpha/gamma potency) of 10 or more, and preferably 15, 25, 30, 50 or 100 or more. According to another aspect, the compounds are dual PPAR alpha and PPAR delta agonists.

According to the invention, the disclosed compounds and compositions are useful for the amelioration of symptoms associated with, the treatment of, and the prevention of, the following conditions and diseases: phase I hyperlipidemia, pre-clinical hyperlipidemia, phase II hyperlipidemia, hypertension, CAD (coronary artery disease), atherosclerosis, coronary heart disease, cardiovascular disease, hypercholesteremia, and hypertriglyceridemia, type II diabetes, insulin resistance, impaired glucose tolerance, dyslipidemia, and low HDL-C. Preferred compounds of the invention are useful in lowering serum levels of low-density lipoproteins (LDL), intermediate density lipoprotein(lIDL), and/or small-density LDL and other atherogenic molecules, or molecules that cause atherosclerotic complications, thereby reducing cardiovascular complications. Preferred compounds also are useful in elevating serum levels of high-density lipoproteins (HDL), in lowering serum levels of triglycerides, LDL, and/or free fatty acids. It is also desirable to lower fasting plasma glucose (FPG)/HbA1c.

PPAR alpha-mediated diseases include Syndrome X (or Metabolic Syndrome), dyslipidemia, high blood pressure, obesity, insulin resistance, impaired fasting glucose, type II diabetes, atherosclerosis, non-alcoholic steatohepatitis, hypercholesterolemia, hypertriglyceridemia, and low HDL-C.

According to one aspect of the invention, the disclosed compounds may be used in a method for treating or inhibiting the progression of a PPAR-delta mediated condition and, optionally, an additional PPAR-alpha mediated condition, said method comprising administering to a patient in need of treatment a pharmaceutically effective amount of a composition of the invention.

Another aspect of the invention is a method of use wherein the PPAR-delta mediated condition is selected from hyperlipidemia, atherosclerosis, cardiovascular disease, hypercholesteremia, type II diabetes, insulin resistance, and impaired glucose tolerance, and other conditions disclosed herein; and a PPAR-alpha mediated condition is selected from Syndrome X (or Metabolic Syndrome), dyslipidemia, high blood pressure, obesity, and impaired fasting glucose, insulin resistance, type II diabetes and other conditions disclosed herein.

A further aspect of the invention is a method for treating at least one PPAR-delta mediated condition and at least one PPAR-alpha mediated condition in a patient, said method comprising administering to a patient in need of treatment a pharmaceutically effective amount of a composition of the invention.

The invention also features pharmaceutical compositions which include, without limitation, one or more of the disclosed compounds, and pharmaceutically acceptable carrier or excipient.

1. Dosages

Those skilled in the art will be able to determine, according to known methods, the appropriate dosage for a patient, taking into account factors such as age, weight, general health, the type of symptoms requiring treatment, and the presence of other medications. In general, an effective amount will be between 0.1 and 1000 mg/kg per day, preferably between 1 and 300 mg/kg body weight, and daily dosages will be between 10 and 5000 mg for an adult subject of normal weight. Capsules, tablets or other formulations (such as liquids and film-coated tablets) may be of between 5 and 200 mg, such as 10, 15, 25, 35, 50 mg, 60 mg, and 100 mg and can be administered according to the disclosed methods.

2. Formulations

Dosage unit forms include tablets, capsules, pills, powders, granules, aqueous and nonaqueous oral solutions and suspensions, and parenteral solutions packaged in containers adapted for subdivision into individual doses. Dosage unit forms can also be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

3. Combination Therapy

The compounds of the present invention may be used in combination with other pharmaceutically active agents. These agents include lipid lowering agents, and blood pressure lowering agents such as statin drugs and the fibrates.

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together.

Anti-diabetic agents include thiazolidinedione and non-thiazolidinedione insulin sensitizers, which decrease peripheral insulin resistance by enhancing the effects of insulin at target organs and tissues.

Some of the following agents are known to bind and activate the nuclear receptor peroxisome proliferator-activated receptor-gamma (PPARγ) which increases transcription of specific insulin-responsive genes. Examples of PPAR-gamma agonists are thiazolidinediones such as:

(1) rosiglitazone(2,4-thiazolidinedione,5-((4-(2-(methyl-2-pyridinylamino)ethoxy)phenyl)methyl)-, (Z)-2-butenedioate (1:1) or 5-((4-(2-(methyl-2-pyridinylamino)ethoxy)phenyl)methyl)-2,4-thiazolidinedione, known as AVANDIA; also known as BRL 49653, BRL 49653C, BRL 49653c, SB 210232, or rosiglitazone maleate);

(2) pioglitazone(2,4-thiazolidinedione, 5-((4-(2-(5-ethyl-2-pyridinyl)ethoxy)phenyl)methyl)-, monohydrochloride, (+ -)- or 5-((4-(2-(5-ethyl-2-pyridyl)ethoxy)phenyl)methy)-2,4-thiazolidinedione, known as ACTOS, ZACTOS, or GLUSTIN; also known as AD 4833, U 72107, U 72107A, U 72107E, pioglitazone hydrochloride (USAN));

(3) troglitazone(5-((4-((3,4-dihydro-6-hydroxy-2,5,7,8-tetramethyl-2H-1-benzopyran-2-yl)methoxy)phenyl)

methyl)-2,4-thiazolidinedione, known as NOSCAL, REZULIN, ROMOZIN, or PRELAY; also known as Cl 991, CS 045, GR 92132, GR 92132X);

(4) isaglitazone((+)-5-[[6-[(2-fluorophenyl)methoxy]-2-naphthalenyl]methyl]-2,4-thiazolidinedione or 5-((6-((2-fluorophenyl)methoxy)-2-naphthalenyl)methyl-2,4-thiazolidinedione or 5-(6-(2-fluorobenzyloxy) naphthalen-2-ylmethyl)thiazolidine- 2,4-dione, also known as MCC-555 or neoglitazone); and (5) 5-BTZD.

Additionally, the non-thiazolidinediones that act as insulin sensitizing agents include, but are not limited to:

(1) JT-501 (JTT 501, PNU-1827, PNU-716-MET-0096, or PNU 182716: isoxazolidine-3,5-dione, 4-((4-(2-phenyl-5-methyl)-1,3-oxazolyl)ethylphenyl-4)methyl-);

(2) KRP-297 (5-(2,4-dioxothiazolidin-5-ylmethyl)-2-methoxy-N-(4-(trifluoromethyl)benzyl)benzamide or 5-((2,4-dioxo-5-thiazolidinyl)methyl)-2-methoxy-N-((4-(trifluoromethyl)phenyl)methyl)benzamide); and (3) Farglitazar (L-tyrosine, N-(2-benzoylphenyl)-o-(2-(5-methyl-2-phenyl-4-oxazolyl)ethyl)- or N-(2-benzoylphenyl)-O-(2-(5-methyl-2-phenyl-4-oxazolyl) ethyl)-L-tyrosine, or GW2570 or GI-262570).

Other agents have also been shown to have PPAR modulator activity such as PPAR gamma, SPPAR gamma, and/or PPAR delta/gamma agonist activity. Examples are listed below:

(1) AD 5075;
(2) R 119702 ((+ −)-5-(4-(5-Methoxy-1H -benzimidazol-2-ylmethoxy)benzyl)thiazolin-2,4-dione hydrochloride, or Cl 1037 or CS 011);
(3) CLX-0940 (peroxisome proliferator-activated receptor alpha agonist/peroxisome proliferator-activated receptor gamma agonist);
(4) LR-90 (2,5,5-tris(4-chlorophenyl)-1,3-dioxane-2-carboxylic acid, PPARdelta/γ agonist);
(5) Tularik (PPARγ agonist);
(6) CLX-0921 (PPARγ agonist);
(7) CGP-52608 (PPAR agonist);
(8) GW-409890 (PPAR agonist);
(9) GW-7845 (PPAR agonist);
(10) L-764406 (PPAR agonist);
(11) LG-101280 (PPAR agonist);
(12) LM-4156 (PPAR agonist);
(13) Risarestat (CT-112);
(14) YM 440 (PPAR agonist);
(15) AR-H049020 (PPAR agonist);
(16) GW 0072 (4-(4-((2S,5S)-5-(2-(bis(phenylmethyl) amino)-2-oxoethyl)-2-heptyl-4-oxo-3-thiazolidinyl) butyl)benzoic acid);
(17) GW 409544 (GW-544 or GW-409544);
(18) NN 2344 (DRF 2593);
(19) NN 622 (DRF 2725);
(20) AR-H039242 (AZ-242);
(21) GW 9820 (fibrate);
(22) GW 1929 (N-(2-benzoylphenyl)-O-(2-(methyl-2-pyridinylamino)ethyl)-L-tyrosine, known as GW 2331, PPAR alpha/γ agonist);
(23) SB 219994 ((S)-4-(2-(2-benzoxazolylmethylamino) ethoxy)-alpha-(2,2,2-trifluoroethoxy)benzen epropanoic acid or 3-(4-(2-(N-(2-benzoxazolyl)-N-methylamino)ethoxy)phenyl)-2(S)-(2,2,2-trifluoroethoxy) propionic acid or benzenepropanoic acid,4-(2-(2-benzoxazolylmethylamino)ethoxy)-alpha-(2,2,2-trifluoroethoxy)-, (alphaS)-, PPARalpha/γ agonist);
(24) L-796449 (PPAR alpha/γ agonist);
(25) Fenofibrate (Propanoic acid, 2-[4-(4-chlorobenzoyl) phenoxy]-2-methyl-, 1-methylethyl ester, known as TRICOR, LIPCOR, LIPANTIL, LIPIDIL MICRO PPAR alpha agonist);
(26) GW-9578 (PPAR alpha agonist);
(27) GW-2433 (PPAR alpha/γ agonist);
(28) GW-0207 (PPARγ agonist);
(29) LG-100641 (PPARγ agonist);
(30) LY-300512 (PPARγ agonist);
(31) NID525-209 (NID-525);
(32) VDO-52 (VDO-52);
(33) LG 100754 (peroxisome proliferator-activated receptor agonist);
(34) LY-510929 (peroxisome proliferator-activated receptor agonist);
(35) bexarotene(4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455); and
(36) GW-1536 (PPAR alpha/γ agonist).

(B) Other insulin sensitizing agents include, but are not limited to:

(1) INS-1 (D-chiro inositol or D-1, 2, 3, 4, 5, 6-hexahydroxycyclohexane);
(2) protein tyrosine phosphatase 1 B (PTP-1B)inhibitors;
(3) glycogen synthase kinase-3 (GSK3)inhibitors;
(4) beta 3 adrenoceptor agonists such as ZD 2079 ((R)-N-(2-(4-(carboxymethyl)phenoxy)ethyl)-N-(2-hydroxy-2-phenethyl) ammonium chloride, also known as ICI D 2079) or AZ 40140;
(5) glycogen phosphorylase inhibitors;
(6) fructose-1,6-bisphosphatase inhibitors;
(7) chromic picolinate, vanadyl sulfate (vanadium oxysulfate);
(8) KP 102 (organo-vanadium compound);
(9) chromic polynicotinate;
(10) potassium channel agonist NN 414;
(11) YM 268 (5,5'-methylene-bis(1,4-phenylene)bismethylenebis(thiazolidine-2,4-dione);
(12) TS 971;
(13) T 174 ((+ −)-5-(2,4-dioxothiazolidin-5-ylmethyl)-2-(2-naphthylmethyl)benzoxazole);
(14) SDZ PGU 693 ((+)-trans-2(S-((4-chlorophenoxy) methyl)-7alpha-(3,4-dichlorophenyl)tetrahydropyrrolo (2,1-b)oxazol-5(6H)-one);
(15) S 15261 ((−)-4-(2-((9H-fluoren-9-ylacetyl)amino) ethyl)benzoic acid 2-((2-methoxy-2-(3-(trifluoromethyl)phenyl)ethyl)amino)ethyl ester);
(16) AZM 134 (Alizyme);
(17) ARIAD;
(18) R 102380;
(19) PNU 140975 (1-(hydrazinoiminomethyl)hydrazino) acetic acid;
(20) PNU 106817 (2-(hydrazinoiminomethyl)hydrazino) acetic acid;
(21) $NC_{2100}$ (5-((7-(phenylmethoxy)-3-quinolinyl)methyl)-2,4-thiazolidinedione;
(22) $MXC_{3255}$;
(23) MBX 102;
(24) ALT 4037;
(25) AM 454;
(26) JTP 20993 (2-(4-(2-(5-methyl-2-phenyl-4-oxazolyl) ethoxy)benzyl)-malonic acid dimethyl diester);
(27) Dexlipotam (5(R)-(1,2-dithiolan-3-yl)pentanoic acid, also known as (R)-alpha lipoic acid or (R)-thioctic acid);

(28) BM 170744 (2,2-Dichloro-12-(p-chlorophenyl) dodecanoic acid);
(29) BM 152054 (5-(4-(2-(5-methyl-2-(2-thienyl)oxazol-4-yl) ethoxy)benzothien-7-ylmethyl)thiazolidine-2,4-dione);
(30) BM 131258 (5-(4-(2-(5-methyl-2-phenyloxazol-4-yl)ethoxy)benzothien-7-ylmethyl)thiazolidine-2,4-dione);
(31) CRE 16336 (EML 16336);
(32) HQL 975 (3-(4-(2-(5-methyl-2-phenyloxazol-4-yl) ethoxy)phenyl)-2(S)-(propylamino)propionic acid);
(33) DRF 2189 (5-((4-(2-(1-Indolyl)ethoxy)phenyl)methyl)thiazolidine-2,4-dione);
(34) DRF 554158;
(35) DRF-NPCC;
(36) CLX 0100, CLX 0101, CLX 0900, or CLX 0901;
(37) IkappaB Kinase (IKK B) Inhibitors
(38) mitogen-activated protein kinase (MAPK) inhibitors p38 MAPK Stimulators
(39) phosphatidyl-inositide triphosphate
(40) insulin recycling receptor inhibitors
(41) glucose transporter 4 modulators
(42) TNF-α antagonists
(43) plasma cell differentiation antigen-1 (PC-1) Antagonists
(44) adipocyte lipid-binding protein (ALBP/aP2) inhibitors
(45) phosphoglycans
(46) Galparan;
(47) Receptron;
(48) islet cell maturation factor;
(49) insulin potentiating factor (IPF or insulin potentiating factor-1);
(50) somatomedin C coupled with binding protein (also known as IGF-BP3, IGF-BP3, SomatoKine);
(51) Diab II (known as V-411) or Glucanin, produced by Biotech Holdings Ltd. or Volque Pharmaceutical;
(52) glucose-6 phosphatase inhibitors;
(53) fatty acid glucose transport protein;
(54) glucocorticoid receptor antagonists; and
(55) glutamine:fructose-6-phosphate amidotransferase (GFAT) modulators.

(C) Biguanides, which decrease liver glucose production and increases the uptake of glucose. Examples include metformin such as:
(1) 1,1-dimethylbiguanide (e.g., Metformin—DepoMed, Metformin—Biovail Corporation, or METFORMIN GR (metformin gastric retention polymer)); and
(2) metformin hydrochloride (N,N-dimethylimidodicarbonimidic diamide monohydrochloride, also known as LA 6023, BMS 207150, GLUCOPHAGE, or GLUCOPHAGE XR.

(D) Alpha-glucosidase inhibitors, which inhibit alpha-glucosidase. Alpha-glucosidase converts fructose to glucose, thereby delaying the digestion of carbohydrates. The undigested carbohydrates are subsequently broken down in the gut, reducing the post-prandial glucose peak. Examples include, but are not limited to:
(1) acarbose (D-glucose, O-4,6-dideoxy-4-(((1S -(1alpha, 4alpha,5beta,6alpha))-4,5,6-trihydroxy-3-(hydroxymethyl)-2-cyclohexen-1-yl)amino)-alpha-D-glucopyranosyl-(1-4)-O-alpha-D-glucopyranosyl-(1-4)-, also known as AG-5421, Bay-g-542, BAY-g-542, GLUCOBAY, PRECOSE, GLUCOR, PRANDASE, GLUMIDA, or ASCAROSE);
(2) Miglitol (3,4,5-piperidinetriol, 1-(2-hydroxyethyl)-2-(hydroxymethyl)-, (2R (2alpha, 3beta, 4alpha, 5beta))- or (2R,3R,4R,5S)-1-(2-hydroxyethyl)-2-(hydroxymethyl-3,4,5-piperidinetriol, also known as BAY 1099, BAY M 1099, BAY-m-1099, BAYGLITOL, DIASTABOL, GLYSET, MIGLIBAY, MITOLBAY, PLUMAROL);
(3) CKD-711 (0-4-deoxy-4-((2,3-epoxy-3-hydroxymethyl-4,5,6-trihydroxycyclohexane-1-yl)amino)-alpha-b-glucopyranosyl-(1-4)-alpha-D-glucopyranosyl-(1-4)-D-glucopyranose);
(4) emiglitate (4-(2-((2R,3R,4R,5S)-3,4,5-trihydroxy-2-(hydroxymethyl)-1-piperidinyl)ethoxy)benzoic acid ethyl ester, also known as BAY o 1248 or $MKC_{542}$);
(5) MOR 14 (3,4,5-piperidinetriol, 2-(hydroxymethyl)-1-methyl-, (2R-(2alpha,3beta,4alpha,5beta))-, also known as N-methyldeoxynojirimycin or N-methylmoranoline); and
(6) Voglibose (3,4-dideoxy-4-((2-hydroxy-1-(hydroxymethyl)ethyl)amino)-2-C-(hydroxymethyl)-D-epi-inositol or D-epi-Inositol,3,4-dideoxy -4-((2-hydroxy -1-(hydroxymethyl)ethyl)amino)-2-C-(hydroxymethyl)-, also known as A 71100, AO 128, BASEN, GLUSTAT, VOGLISTAT.

(E) Insulins include regular or short-acting, intermediate-acting, and long-acting insulins, non-injectable or inhaled insulin, tissue selective insulin, glucophosphokinin (D-chiroinositol), insulin analogues such as insulin molecules with minor differences in the natural amino acid sequence and small molecule mimics of insulin (insulin mimetics), and endosome modulators. Examples include, but are not limited to:
(1) Biota;
(2) LP 100;
(3) (SP-5-21)-oxobis(1-pyrrolidinecarbodithioato-S,S') vanadium,
(4) insulin aspart (human insulin (28B -L-aspartic acid) or B28-Asp-insulin, also known as insulin X14, INA-X14, NOVORAPID, NOVOMIX, or NOVOLOG);
(5) insulin detemir (Human 29B-(N6-(1-oxotetradecyl)-L-lysine)-(1A-21A), (1B-29B)-Insulin or NN 304);
(6) insulin lispro (28B-L-lysine-29B-L-proline human insulin, or Lys(B28), Pro(B29) human insulin analog, also known as lys-pro insulin, LY 275585, HUMALOG, HUMALOG MIX 75/25, or HUMALOG MIX 50/50);
(7) insulin glargine (human (A21-glycine, B31-arginine, B32-arginine) insulin HOE 901, also known as LANTUS, OPTISULIN);
(8) Insulin Zinc Suspension, extended (Ultralente), also known as HUMULIN U or ULTRALENTE;
(9) Insulin Zinc suspension (Lente), a 70% crystalline and 30% amorphous insulin suspension, also known as LENTE ILETIN II, HUMULIN L, or NOVOLIN L;
(10) HUMULIN 50/50 (50% isophane insulin and 50% insulin injection);
(11) HUMULIN 70/30 (70% isophane insulin NPH and 30% insulin injection), also known as NOVOLIN 70/30, NOVOLIN 70/30 PenFill, NOVOLIN 70/30 Prefilled;
(12) insulin isophane suspension such as NPH ILETIN II, NOVOLIN N, NOVOLIN N PenFill, NOVOLIN N Prefilled, HUMULIN N;
(13) regular insulin injection such as ILETIN II Regular, NOVOLIN R, VELOSULIN BR, NOVOLIN R PenFill, NOVOLIN R Prefilled, HUMULIN R, or Regular U-500 (Concentrated);
(14) ARIAD;
(15) LY 197535;

(16) L-783281; and
(17) TE-17411.
(F) Insulin secretion modulators such as:
(1) glucagon-like peptide-1 (GLP-1) and its mimetics;
(2) glucose-insulinotropic peptide (GIP) and its mimetics;
(3) exendin and its mimetics;
(4) dipeptyl protease (DPP or DPPIV) inhibitors such as
(4a) DPP-728 or LAF 237 (2-pyrrolidinecarbonitrile,1-(((2-((5-cyano-2-pyridinyl)amino)ethyl)amino)acetyl), known as NVP-DPP-728, DPP -728A, LAF -237);
(4b) P 3298 or P32/98 (di-(3N -((2S, 3S)-2-amino-3-methyl-pentanoyl)-1,3-thiazolidine)fumarate);
(4c) TSL 225 (tryptophyl-1,2,3,4-tetrahydroisoquinoline-3-carboxylic acid);
(4d) Valine pyrrolidide (valpyr);
(4e) 1-aminoalkylisoquinolinone-4-carboxylates and analogues thereof;
(4f) SDZ 272-070 (1-(L-Valyl)pyrrolidine);
(4g) TMC-2A, TMC-2B, or TMC-2C;
(4h) Dipeptide nitriles (2-cyanopyrrolodides);
(4i) CD26 inhibitors; and
(4j) SDZ 274-444;
(5) glucagon antagonists such as AY-279955; and
(6) amylin agonists which include, but are not limited to, pramlintide (AC-137, Symlin, tripro-amylin or pramlintide acetate).

The present compounds may also increase insulin sensitivity with little or no increase in body weight than that found with the use of existing PPAR gamma agonists. Oral anti-diabetic agents may include insulin, sulfonylureas, biguanides, meglitinides, AGI's, PPAR alpha agonists, and PPAR gamma agonists, and dual PPAR alpha/gamma agonists.

The present compounds also may increase fat and/or lipid metabolism, providing a method for losing weight, losing fat weight, lowering body mass index, lowering lipids (such as lowering triglycerides), or treating obesity or the condition of being overweight. Examples of lipid lowering agents include bile acid sequestrants, fibric acid derivatives, nicotinic acid, and HMGCoA reductase inhibitors. Specific examples include statins such as LIPITOR®, ZOCOR®, PRAVACHOL®, LESCOL®, and MEVACOR®, and pitavastatin (nisvastatin) (Nissan, Kowa Kogyo, Sankyo, Novartis) and extended release forms thereof, such as ADX-159 (extended release lovastatin), as well as Colestid, Locholest, Questran, Atromid, Lopid, and Tricor.

Examples of blood pressure lowering agents include anti-hypertensive agents, such as angiotensin-converting enzyme (ACE) inhibitors (Accupril, Altace, Captopril, Lotensin, Mavik, Monopril, Prinivil, Univasc, Vasotec, and Zestril), adrenergic blockers (such as Cardura, Dibenzyline, Hylorel, Hytrin, Minipress, and Minizide) alpha/beta adrenergic blockers (such as Coreg, Normodyne, and Trandate), calcium channel blockers (such as Adalat, Calan, Cardene, Cardizem, Covera-HS, Dilacor, DynaCirc, Isoptin, Nimotop, Norvace, Plendil, Procardia, Procardia XL, Sula, Tiazac, Vascor, and Verelan), diuretics, angiotensin II receptor antagonists (such as Atacand, Avapro, Cozaar, and Diovan), beta adrenergic blockers (such as Betapace, Blocadren, Brevibloc, Cartrol, Inderal, Kerlone, Lavatol, Lopressor, Sectral, Tenormin, Toprol-XL, and Zebeta), vasodilators (such as Deponit, Dilatrate, SR, lmdur, Ismo, Isordil, Isordil Titradose, Monoket, Nitro-Bid, Nitro-Dur, Nitrolingual Spray, Nitrostat, and Sorbitrate), and combinations thereof (such as Lexxel, Lotrel, Tarka, Teczem, Lotensin HCT, Prinzide, Uniretic, Vaseretic, Zestoretic).

F. Biological Examples

Transfection Assay Method for PPAR Receptors

HEK293 cells were grown in DMEM/F12 medium supplemented with 10% FBS and glutamine (Invitrogen) and incubated in a 5% $CO_2$ incubator at 37° C. The cells were co-transfected using DMRIE-C reagent (Invitrogen) in serum free medium (Opti-MEM, Invitrogen) with two mammalian expression plasmids, one containing the DNA sequence coding for the ligand binding domains of either PPARαg or d fused to the yeast GAL4 DNA binding domain and the other containing the promoter sequence of the yeast GAL4 (UAS) fused to the firefly luciferase cDNA reporter. The next day, the medium was changed to DMEM/F12 medium supplemented with 5% charcoal treated serum (Hyclone) and glutamine. After 6 hrs the cells were trypsinized and seeded at a density of 50,000 cells/well into 96 well plates and incubated overnight as above. The cells were then treated with -test compounds or vehicle and incubated for 18–24 hrs as above. Luciferase reporter activity was measured using the Steady-Glo Luciferase Assay Kit from Promega. DMRIE-C Reagent was purchased from GIBCO Cat. No.10459-014. OPTI-MEM I Reduced Serum Medium was purchased from GIBCO (Cat. No. 31985). Steady-Glo Luciferase Assay Kit was purchased from Promega (Part#E254B).

A variety of example compounds have been made and tested, with a range of in vitro results. Below are representative compounds and data; in some cases, where multiple $EC_{50}$'s are shown, multiple measurements were taken. Naturally, different compounds in Formula (I) may have not have activities identical to any one compound below.

TABLE 1

In Vitro Data

| Compound Number | Structure | $EC_{50}$ (delta) nM | $EC_{50}$ (alpha) nM | $EC_{50}$ (gamma) nM |
| --- | --- | --- | --- | --- |
| 1 | 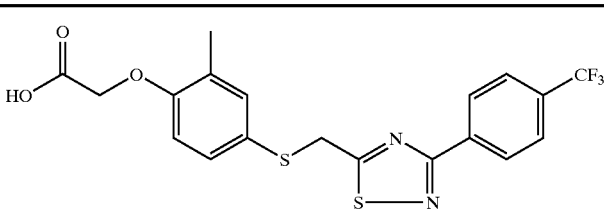 | 10 | 468 | |

TABLE 1-continued

In Vitro Data

| Compound Number | Structure | EC$_{50}$ (delta) nM | EC$_{50}$ (alpha) nM | EC$_{50}$ (gamma) nM |
|---|---|---|---|---|
| 2 | 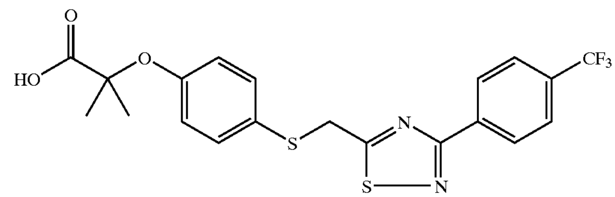 | 20 | 155 | |
| 3 | 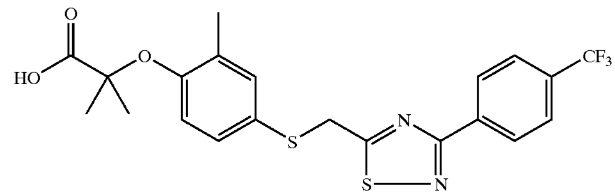 | 7.5 | 87 | 488 |
| 4 | 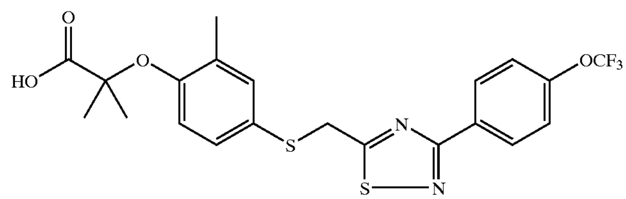 | 3.2 | 33 | 11643 |
| 5 | 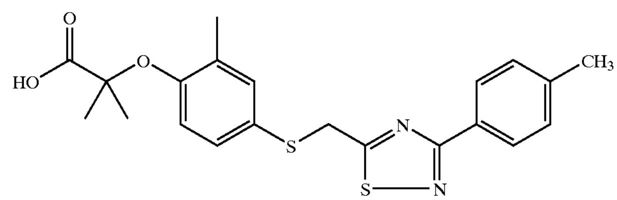 | 47 | 222 | >3000 |
| 6 | 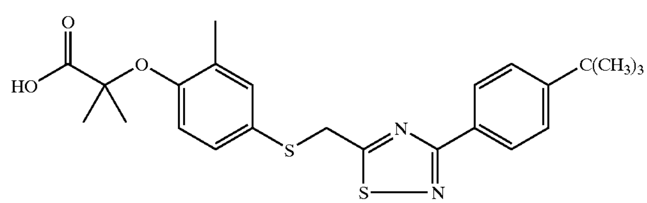 | 93 | 64 | >3000 |
| 7 | 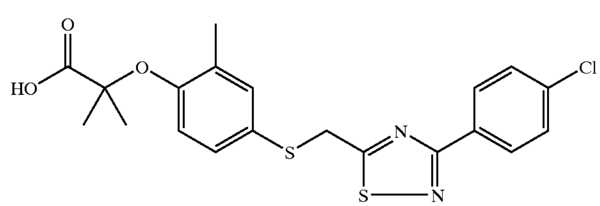 | 18 | 186 | >3000 |
| 8 | 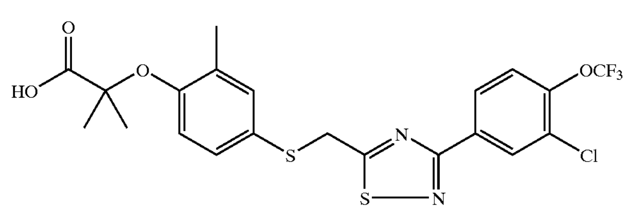 | 2.8 | 28 | >3000 |

TABLE 1-continued

In Vitro Data

| Compound Number | Structure | EC$_{50}$ (delta) nM | EC$_{50}$ (alpha) nM | EC$_{50}$ (gamma) nM |
|---|---|---|---|---|
| 9 | 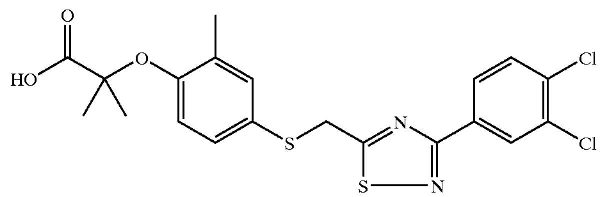 | 13 | 104 | >3000 |
| 10 | 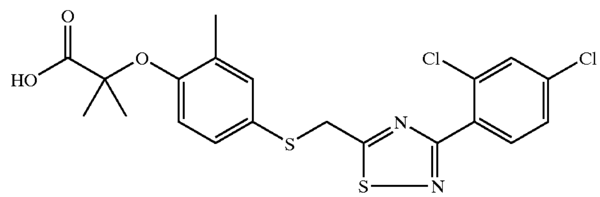 | 102 | 476 | >3000 |
| 11 | 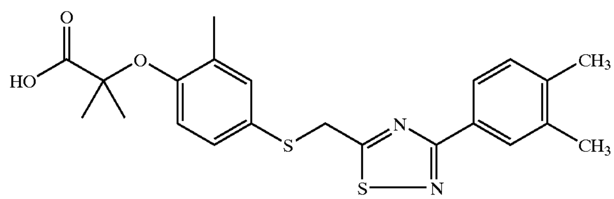 | 93 | 115 | >3000 |
| 12 | 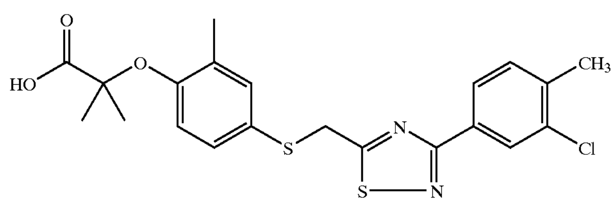 | 27 | 68 | 669 |
| 13 | 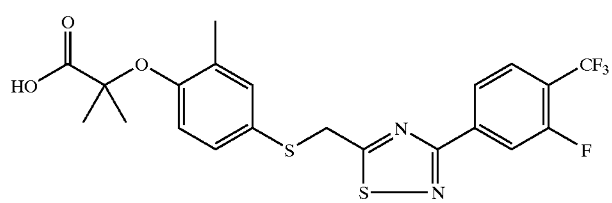 | 5.2 | 34 | 640 |
| 14 | 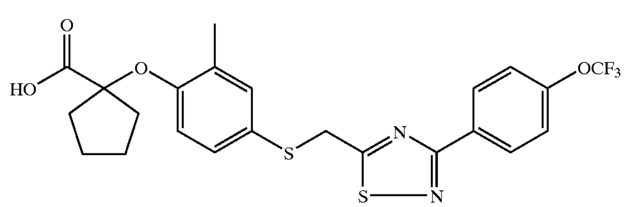 | >1000 | 736 | >3000 |
| 15 | 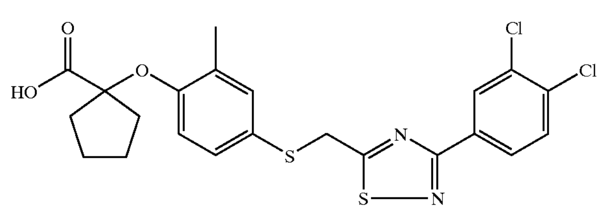 | >1000 | >3000 | >3000 |

TABLE 1-continued

In Vitro Data

| Compound Number | Structure | EC$_{50}$ (delta) nM | EC$_{50}$ (alpha) nM | EC$_{50}$ (gamma) nM |
|---|---|---|---|---|
| 16 | 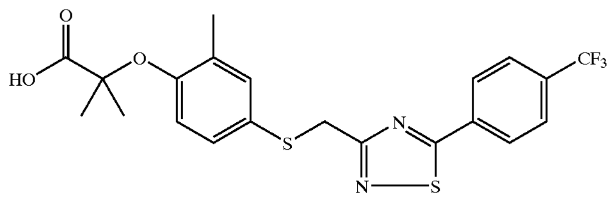 | 26 | 425 | >3000 |
| 17 | 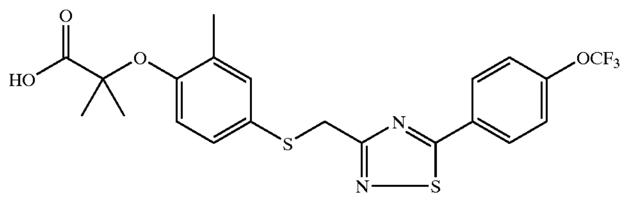 | 58 | 656 | >3000 |
| 18 | 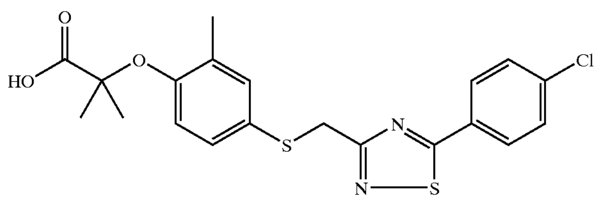 | 237 | >3000 | >3000 |
| 19 | 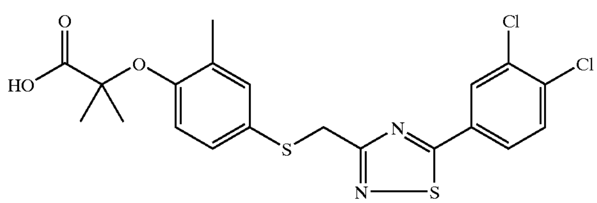 | 229 | >3000 | >3000 |
| 20 | 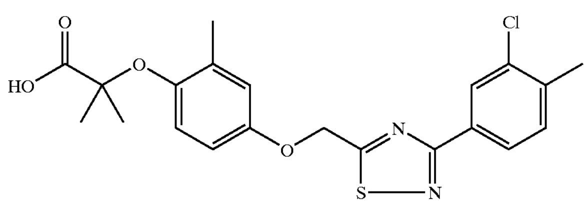 | 148 | 297 | >3000 |
| 21 | 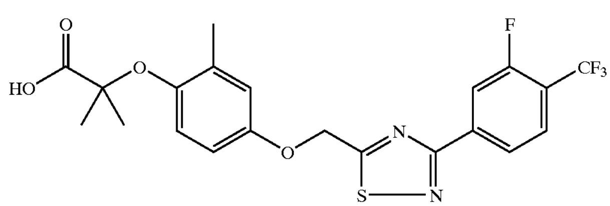 | 3 | 85 | >3000 |
| 22 | 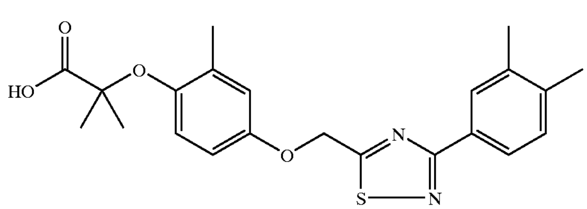 | 534 | 643 | >3000 |

TABLE 1-continued

In Vitro Data

| Compound Number | Structure | EC$_{50}$ (delta) nM | EC$_{50}$ (alpha) nM | EC$_{50}$ (gamma) nM |
|---|---|---|---|---|
| 23 | 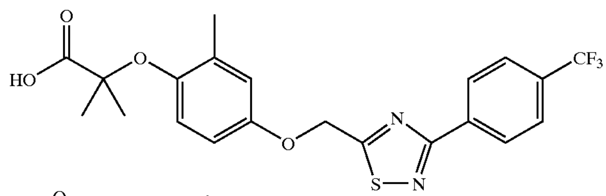 | 3.05 | 94 | >3000 |
| 24 | 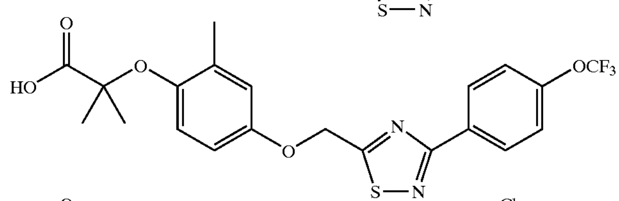 | 12.3 | 93.5 | >3000 |
| 25 | 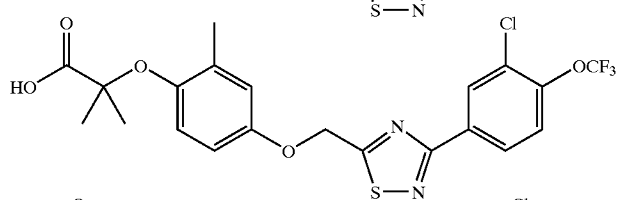 | 13 | 96.8 | >3000 |
| 26 | 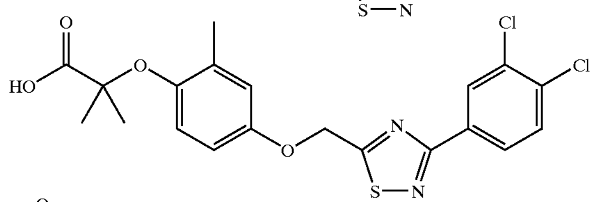 | 113.8 | 503.7 | >3000 |
| 27 | 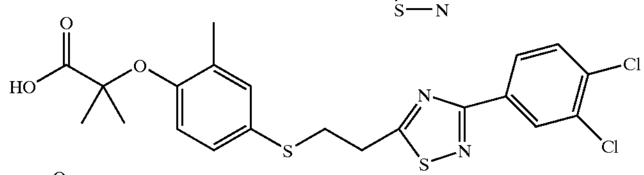 | 9.3 | 123 | >1000 |
| 28 | 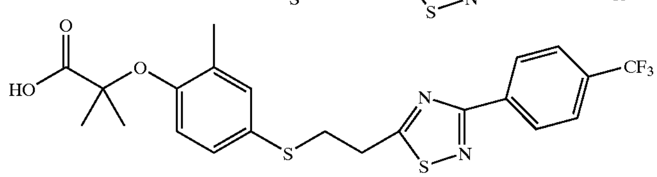 | 1.7 | 37.3 | 465 |

The compounds in Table 2 are also of interest, which have been made and tested likewise.

TABLE 2

In Vitro Data for Compounds of Interest

| Compound of Interest | Structure | EC$_{50}$ (delta) nM | EC$_{50}$ (alpha) nM | EC$_{50}$ (gamma) nM |
|---|---|---|---|---|
| a | 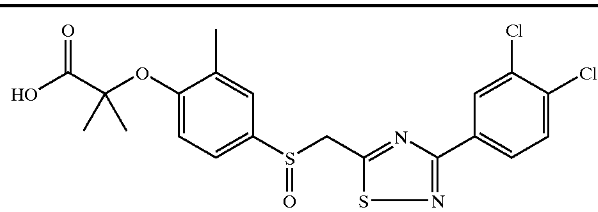 | 412 | >3000 | >3000 |

TABLE 2-continued

In Vitro Data for Compounds of Interest

| Compound of Interest | Structure | EC$_{50}$ (delta) nM | EC$_{50}$ (alpha) nM | EC$_{50}$ (gamma) nM |
|---|---|---|---|---|
| b | (structure) | 1.6 | >3000 | >3000 |
| c | (structure) | 4.5 | >1000 | >3000 |
| d | (structure) | 150 | >3000 | >3000 |
| e | (structure) | 37 | >3000 | >3000 |
| f | (structure) | 20 | >3000 | >3000 |
| g | (structure) | 1.5 | 2208 | >3000 |

The following are the physical data of these compounds of interest (a–g):

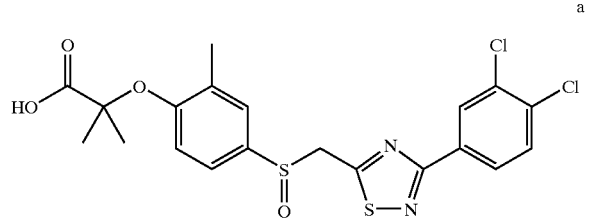

2-{4-[3-(3,4-Dichloro-phenyl)-[1,2,4]thiadiazol-5-ylmethanesulfinyl]-2-methyl-phenoxy}-2-methyl-propionic acid Compound a: $^1$HNMR (300 MHz, DMSO-d$_6$) δ 8.16 (d, J=1.8 Hz, 1H), 7.99–8.02 (dd, J=1.8, 8.4 Hz, 1 H), 7.77–7.80 (d, J=8.4 Hz, 1H), 7.34 (s, 1H), 7.25 (d, J=8.4 Hz, 1H), 6.78 (d, J=8.5 Hz, 1H), 4.84–5.05 (dd, J=3.6, 8.6 Hz, 2H), 2.12 (s, 3H), 1.46 (s, 3H), 1.40 (s, 3H); MS (ES) m/z: 484 (M+H+); Anal. Calcd for C$_{20}$H$_{18}$Cl$_2$N$_2$O$_4$S$_2$.0.40H$_2$O: C, 48.76; H, 3.85; N, 5.69; Found: C, 48.62; H, 3.58; N, 5.56.

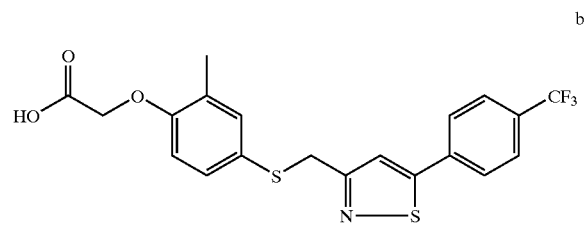

{2-Methyl-4-[5-(4-trifluoromethyl-phenyl)-isothiazol-3-ylmethylsulfanyl]-phenoxy}-acetic acid Compound b: $^1$H NMR (300 MHz, CDCl$_3$) δ 7.69 (d, J=8.7 Hz, 2 H), 7.65 (d, J=8.6 Hz, 2 H), 7.35 (s, 1 H), 7.18 (s, 1 H), 7.16 (m, 1 H), 6.64 (d, J=8.2 Hz, 1 H), 4.66 (s, 2 H), 4.17 (s, 2 H), 2.22 (s, 3 H); MS (ES) m/z: 440 (M+H$^+$). Anal. Calcd. For C$_{20}$H$_{16}$F$_3$NO$_3$S$_2$.0.6 H$_2$O: C, 53.35; H, 3.85; N, 3.11. Found C, 53.20; H, 3.51; N, 2.91.

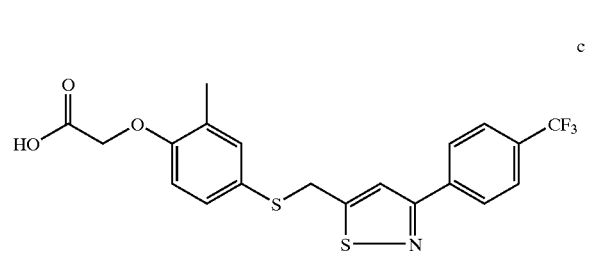

{2-Methyl-4-[3-(4-trifluoromethyl-phenyl)-isothiazol-5-ylmethylsulfanyl]-phenoxy}-acetic acid Compound c: $^1$H NMR (300 MHz, CDCl$_3$) δ 7.96 (d, J=8.1 Hz, 2 H), 7.67 (d, J=8.2 Hz, 2 H), 7.32 (s, 1 H), 7.24 (d, J=1.7 Hz, 1 H), 7.19 (dd, J=8.4, 2.2 Hz, 1 H), 6.63 (d, J=8.4 Hz, 1 H), 4.67 (s, 2 H), 4.26 (s, 2 H), 2.23 (s, 3 H); MS (ES) m/z: 440 (M+H$^+$). Anal. Calcd. For C$_{20}$H$_{16}$F$_3$NO$_3$S$_2$: C, 54.66; H, 3.67; N, 3.19. Found: C, 54.30; H, 3.52; N, 3.06.

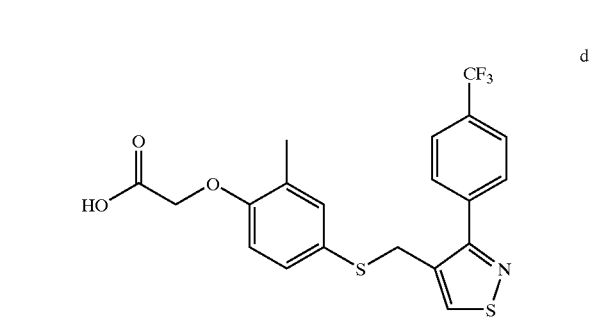

{2-Methyl-4-[3-(4-trifluoromethyl-phenyl)-isothiazol-4-ylmethylsulfanyl]-phenoxy}-acetic acid Compound d: $^1$H NMR (300 MHz, MeOH-d$_4$) δ 8.56 (s, 1 H), 7.75 (s, 4 H), 7.01 (s, 1 H), 6.99 (m, 1 H), 6.66 (d, J=8.2 Hz, 1 H), 4.67 (s, 2 H), 4.10 (s, 2 H), 2.14 (s, 3 H); MS (ES) m/z: 440 (M+H$^+$). Anal. Calcd. For C$_{20}$H$_{16}$F$_3$NO$_3$S$_2$: C, 54.66; H, 3.67; N, 3.19. Found: C, 54.54; H, 3.53; N, 3.01.

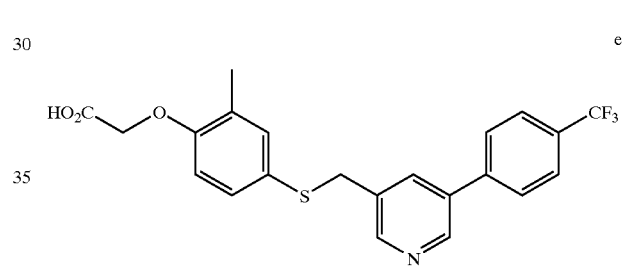

{2-Methyl-4-[5-(4-trifluoromethyl-phenyl)-pyridin-3-ylmethylsulfanyl]-phenoxy}-acetic acid Compound e: $^1$H NMR (400 MHz, MeOH-d$_4$) δ 8.67 (brs, 1 H), 8.35 (brs, 1 H), 7.78 (d, J=8.3 Hz, 2 H), 7.70 (s, 1 H), 7.69 (d, J=8.0 Hz, 2 H), 7.14 (dd, J=8.4, 2.2 Hz, 1 H), 7.09 (d, J=1.6 Hz, 1 H), 6.73 (d, J=8.4 Hz, 1 H), 4.65 (s, 2 H), 4.08 (s, 2 H), 2.15 (s, 3 H); MS (ES) m/z: 434 (M+H$^+$).

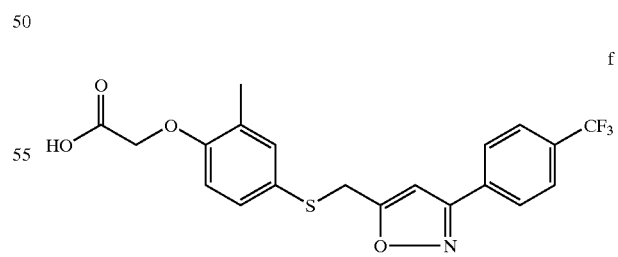

{2-Methyl-4-[3-(4-trifluoromethyl-phenyl)-isoxazol-5-ylmethylsulfanyl]-phenoxy}-acetic acid Compound f: as a white solid; $^1$H NMR (300 MHz, CDCl$_3$) δ 7.87 (d, J=8.1 Hz, 2 H), 7.70 (d, J=8.0 Hz, 2 H), 7.25 (s, 1 H), 7.20 (dd, J=8.3, 1.9 Hz, 1 H), 6.65 (d, J=8.3

Hz, 1 H), 6.34 (s, 1 H), 4.68 (s, 2 H), 4.10 (s, 2 H), 2.24 (s, 3 H); MS (ES) m/z: 446 (M+Na⁺).

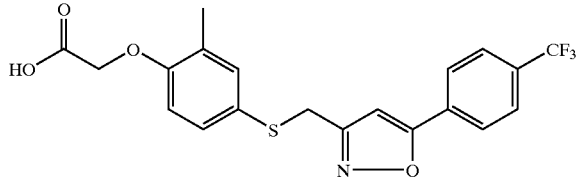

{2-Methyl-4-[5-(4-trifluoromethyl-phenyl)-isoxazol-3-ylmethylsulfanyl]-phenoxy}-acetic acid Compound g: as an off-white solid; $^1$H NMR (300 MHz, CDCl$_3$) δ 7.84 (d, J=8.2 Hz, 2 H), 7.71 (d, J=8.3 Hz, 2 H), 7.22 (d, J=1.6 Hz, 1 H), 7.17 (dd, J=8.4, 2.1 Hz, 1 H), 6.63 (d, J=8.4 Hz, 1 H), 6.56 (s, 1 H), 4.65 (s, 2 H), 4.05 (s, 2 H), 2.22 (s, 3 H); MS (ES) m/z: 446 (M+Na⁺). Anal. Calcd. For C$_{20}$H$_{16}$F$_3$NO$_4$S: C, 56.73; H, 3.81; N, 3.31. Found: C, 56.76; H, 3.46; N, 3.20.

G. Other Embodiments

The features and principles of the invention are illustrated in the discussion, examples, and claims herein. Various adaptations and modifications of the invention will be apparent to a person of ordinary skill in the art and such other embodiments are also within the scope of the invention. Publications cited herein are incorporated in their entirety by reference.

The invention claimed is:

1. A compound of Formula (I):

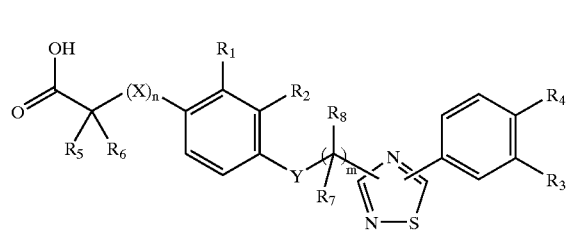

Wherein
m is 1, 2 or 3;
n is 0 or 1;
X is S or O;
Y is S, CH$_2$ or O;
R$_1$ and R$_2$ are independently selected from H, C$_{1-4}$ alkyl, C$_{1-3}$ alkoxy, halo, and —NR$_a$R$_b$, wherein each of R$_a$ and R$_b$ is independently selected from H and C$_{1-4}$ alkyl;
each of R$_3$ and R$_4$ is independently selected from H, halo, cyano, C$_{1-4}$ alkyl, C$_{1-3}$ alkoxy, and NR$_c$R$_d$, wherein each of R$_c$ and R$_d$ is independently selected from H and C$_{1-4}$ alkyl; and wherein at least one of R$_3$ and R$_4$ is not H; and
each of R$_5$ and R$_6$ is independently selected from H, C$_{1-5}$ alkyl, C$_{1-5}$ alkoxy, C$_{3-5}$ cycloalkyl, (C$_{3-5}$ cycloalkyl) C$_{1-3}$ alkyl, and NR$_e$R$_f$, wherein each of R$_e$ and R$_f$ is independently selected from H and C$_{1-4}$ alkyl; or R$_5$ and R$_6$ together to form spiro C$_{3-6}$ cycloalkyl, or spiro 5- or 6-membered heterocyclyl having between 1 and 3 heteroatoms selected from O, S, and N; and
each of R$_7$ and R$_8$ is independently selected from H, C$_{1-5}$ alkyl, and C$_{3-5}$ cycloalkyl;

or a pharmaceutically acceptable salt thereof.

2. A compound of claim 1, wherein m is 1 or 2.
3. A compound of claim 1, wherein m is 1.
4. A compound of claim 1, wherein n is 1.
5. A compound of claim 1, wherein X is O.
6. A compound of claim 1, wherein Y is S or O.
7. A compound of claim 1, wherein Y is S.
8. A compound of claim 1, wherein Y is O.
9. A compound of claim 1, wherein R$_1$ is selected from H, C$_{1-2}$ alkyl, C$_{1-2}$ alkoxy and halo.
10. A compound of claim 1, wherein R$_1$ is selected from halo, methyl, and methoxy, and if methyl or methoxy, R$_1$ may be substituted or unsubstituted.
11. A compound of claim 1, wherein R$_2$ is H, halo, methoxy, or methyl.
12. A compound of claim 1, wherein R$_2$ is H, fluoro, or chloro.
13. A compound of claim 1, wherein each of R$_3$ and R$_4$ is independently selected from H, halo, C$_{1-4}$ alkyl, C$_{1-3}$ alkoxy, and NR$_c$R$_d$.
14. A compound of claim 1, wherein each of R$_3$ and R$_4$ is independently selected from H, fluoro, chloro, C$_{1-2}$ alkyl, and C$_{1-2}$ alkoxy.
15. A compound of claim 1, wherein each of R$_3$ and R$_4$ is independently selected from H, fluoro, chloro, methyl, methoxy, trifluoromethyl, trifluoromethoxy, difluoromethyl, difluoromethoxy, fluoromethyl, fluoromethoxy, trifluoroethyl, and trifluoroethoxy.
16. A compound of claim 1, wherein each of R$_5$ and R$_6$ is independently selected from H, C$_{1-3}$ alkyl, and C$_{1-3}$ alkoxy.
17. A compound of claim 1, wherein at least one of R$_5$ and R$_6$ is methyl, methoxy, ethyl, and ethoxy; and the other is selected from H, methoxy, methyl, ethyl, and ethoxy.
18. A compound of claim 1, wherein each of R$_7$ and R$_8$ is independently selected from H and C$_{1-3}$ alkyl.
19. A compound of claim 1, wherein one of R$_7$ and R$_8$ is H and the other is H, methyl, or ethyl.
20. A compound of claim 1, wherein each of R$_7$ and R$_8$ is H.
21. A compound of claim 1, wherein X is O; Y is S or O; R$_1$ is selected from H, C$_{1-2}$ alkyl, C$_{1-2}$ alkoxy, and halo; each of R$_5$ and R$_6$ is independently selected from H, C$_{1-3}$ alkyl, and C$_{1-3}$ alkoxy; and each of R$_7$ and R$_8$ is independently selected from H and C$_{1-3}$ alkyl.
22. A compound of claim 1, wherein m is 1 or 2 and n is 1.
23. A compound of claim 1, wherein each of R$_3$ and R$_4$ is independently selected from H, fluoro, chloro, C$_{1-2}$ alkyl, and C$_{1-2}$ alkoxy; and R$_1$ is selected from H, C$_{1-2}$ alkyl, C$_{1-2}$ alkoxy and halo.
24. A compound of claim 1, wherein each of R$_3$ and R$_4$ is independently selected from H, fluoro, chloro, methyl, methoxy, trifluoromethyl, trifluoromethoxy, trifluoroethyl, and trifluoroethoxy.
25. A compound of claim 1, wherein
m is 1 or 2;
n is 0 or 1;
X is S or O;
Y is S, CH$_2$ or O;
R$_1$ and R$_2$ are independently selected from H, C$_{1-4}$ alkyl, C$_{1-3}$ alkoxy, halo, and —NR$_a$R$_b$, wherein each of R$_a$ and R$_b$ is independently selected from H and C$_{1-4}$ alkyl;

each of $R_3$ and $R_4$ is independently selected from H, halo, cyano, $C_{1-4}$ alkyl, $C_{1-3}$ alkoxy, and $NR_cR_d$, wherein each of $R_c$ and $R_d$ is independently selected from H and $C_{1-4}$ alkyl; and wherein at least one of $R_3$ and $R_4$ is not H;

each of $R_5$ and $R_6$ is independently selected from H, $C_{1-5}$ alkyl, $C_{1-5}$ alkoxy, $C_{3-5}$ cycloalkyl, ($C_{3-5}$ cycloalkyl) $C_{1-3}$ alkyl, and $NR_eR_f$, wherein each of $R_e$ and $R_f$ is independently selected from H and $C_{1-4}$ alkyl; or $R_5$ and $R_6$ together to form spiro $C_{3-6}$ cycloalkyl; and each of $R_7$ and $R_8$ is independently selected from H and $C_{1-2}$ alkyl.

26. A compound of claim 1, wherein m is 1 or 2;
n is 0 or 1;
X is S or O;
Y is S or O;
$R_1$ and $R_2$ are independently selected from H, $C_{1-2}$ alkyl, $C_{1-2}$ alkoxy, halo, and —$NR_aR_b$, wherein each of $R_a$ and $R_b$ is independently selected from H and $C_{1-4}$ alkyl;

each of $R_3$ and $R_4$ is independently selected from H, halo, cyano, $C_{1-4}$ alkyl, $C_{1-3}$ alkoxy, and $NR_cR_d$, wherein each of $R_c$ and $R_d$ is independently selected from H and $C_{1-4}$ alkyl; and wherein at least one of $R_3$ and $R_4$ is not H;

each of $R_5$ and $R_6$ is independently selected from H, $C_{1-3}$ alkyl, $C_{1-2}$ alkoxy; and each of $R_7$ and $R_8$ is H.

27. A compound of claim 1, selected from:
2-Methyl-2-{2-methyl-4-[3-(4-trifluoromethyl-phenyl)-[1,2,4]thiadiazol-5-ylmethoxy]-phenoxy}-propionic acid,
2-Methyl-2-{2-methyl-4-[3-(4-trifluoromethoxy-phenyl)-[1,2,4]thiadiazol-5-ylmethoxy]-phenoxy}-propionic acid,
2-Methyl-2-[2-methyl -4-(3-p-tolyl-[1,2,4]thiadiazol-5-ylmethylsulfanyl)-phenoxy]-propionic acid,
2-{4-[3-(4-tert-Butyl-phenyl)-[1,2,4]thiadiazol-5-ylmethylsulfanyl]-2-methyl-phenoxy}-2-methyl-propionic acid,
2-{4-[3-(4-Chloro-phenyl)-[1,2,4]thiadiazol-5-ylmethylsulfanyl]-2-methyl-phenoxy}-2-methyl-propionicacid,
2-{4-[3-(3-Chloro-4-trifluoromethoxy-phenyl)-[1,2,4]thiadiazol-5-ylmethylsulfanyl]-2-methyl-phenoxy}-2-methyl-propionic acid,
2-{4-[3-(3,4-Dichloro-phenyl)-[1,2,4]thiadiazol-5-ylmethylsulfanyl]-2-methyl-phenoxy}-2-methyl-propionic acid,
2-{4-[3-(2,4-Dichloro-phenyl)-[1,2,4]thiadiazol-5-ylmethylsulfanyl]-2-methyl-phenoxy}-2-methyl-propionic acid,
2-{4-[3-(3,4-Dimethyl-phenyl)-[1,2,4]thiadiazol-5-ylmethylsulfanyl]-2-methyl-phenoxy}-2-methyl-propionic acid,
2-{4-[3-(3-Chloro-4-methyl-phenyl)-[1,2,4]thiadiazol-5-ylmethylsulfanyl]-2-methyl-phenoxy}-2-methyl-propionic acid,
2-{4-[3-(3-Fluoro 4-trifluoromethyl-phenyl)-[1,2,4]thiadiazol-5-ylmethylsulfanyl]-2-methyl-phenoxy}-2-methyl-propionic acid,
1-{2-Methyl-4-[3-(4-trifluoromethoxy-phenyl)-[1,2,4]thiadiazol-5-ylmethylsulfanyl]-phenoxy}-cyclopentanecarboxylic acid,
1-{4-[3-(3,4-Dichloro-phenyl)-[1,2,4]thiadiazol-5-ylmethylsulfanyl]-2-methyl-phenoxy}-cyclopentanecarboxylic acid,
2-Methyl-2-{2-methyl-4-[5-(4-trifluoromethyl-phenyl)-[1,2,4]thiadiazol-3-ylmethylsulfanyl]-phenoxy}-propionic acid,
2-{4-[5-(4-Chloro-phenyl)-[1,2,4]thiadiazol-3-ylmethylsulfanyl]-2-methyl-phenoxy}-2-methyl-propionic acid,
2-{4-[5-(4-Isopropyl-phenyl)-[1,2,4]thiadiazol-3-ylmethylsulfanyl]-2-methyl-phenoxy}-2-methyl-propionic acid,
2-Methyl-2-{2-methyl-4-[5-(4-trifluoromethoxy-phenyl)-[1,2,4]thiadiazol-3-ylmethylsulfanyl]-phenoxy}-propionic acid,
2-{4-[5-(4-tert-Butyl-phenyl)-[1,2,4]thiadiazol-3-ylmethylsulfanyl]-2-methyl-phenoxy}-2-methyl-propionic acid,
2-Methyl-2-{2-methyl-4-[3-(4-trifluoromethoxy-phenyl)-[1,2,4]thiadiazol-5-ylmethylsulfanyl]-phenoxy}-propionic acid,
{2-Methyl-4-[3-(4-trifluoromethyl-phenyl)-[1,2,4]thiadiazol-5-ylmethylsulfanyl]-phenoxy}-acetic acid,
2-Methyl-2-{2-methyl-4-[3-(4-trifluoromethyl-phenyl)-[1,2,4]thiadiazol-5-ylmethylsulfanyl]-phenoxy}-propionic acid, and
2-Methyl-2-{4-[3-(4-trifluoromethyl-phenyl)-[1,2,4]thiadiazol-5-ylmethylsulfanyl]-phenoxy}-propionic acid.

28. A compound of claim 1, selected from:
2-Methyl-2-{2-methyl-4-[3-(4-trifluoromethoxy-phenyl)-[1,2,4]thiadiazol-5-ylmethylsulfanyl]-phenoxy}-propionic acid,
2-{4-[3-(3-Chloro-4-trifluoromethoxy-phenyl)-[1,2,4]thiadiazol-5-ylmethylsulfanyl]-2-methyl-phenoxy}-2-methyl-propionic acid,
2-Methyl-2-{2-methyl-4-[3-(4-trifluoromethyl-phenyl)-[1,2,4]thiadiazol-5-ylmethoxy]-phenoxy}-propionic acid,
2-Methyl-2-{2-methyl-4-[3-(4-trifluoromethoxy-phenyl)-[1,2,4]thiadiazol-5-ylmethoxy]-phenoxy}-propionic acid,
2-{4-[3-(3,4-Dichloro-phenyl)-[1,2,4]thiadiazol-5-ylmethylsulfanyl]-2-methyl-phenoxy}-2-methyl-propionic acid,
2-Methyl-2-{2-methyl-4-[3-(4-trifluoromethoxy-phenyl)-[1,2,4]thiadiazol-5-ylmethylsulfanyl]-phenylsulfanyl}-propionic acid,
2-{4-[3-(3,4-Dichloro-phenyl)-[1,2,4]thiadiazol-5-ylmethylsulfanyl]-2-methyl-phenylsulfanyl}-2-methyl-propionic acid,
2-{4-[3-(3-Chloro-4-trifluoromethoxy-phenyl)-[1,2,4]thiadiazol-5-ylmethylsulfanyl]-2-methyl-phenylsulfanyl}-2-methyl-propionic acid,
2-{4-[3-(4-tert-Butyl-phenyl)-[1,2,4]thiadiazol-5-ylmethylsulfanyl]-2-methyl-phenylsulfanyl}-2-methyl-propionic acid, and
2-Methyl-2-(2-methyl-4-{3-[3-(4-trifluoromethoxy-phenyl)-[1,2,4]thiadiazol-5-yl]-propyl}-phenoxy)-propionic acid.

29. A compound of claim 1, selected from:
2-Methyl-2-{2-methyl-4-[3-(4-trifluoromethyl-phenyl)-[1,2,4]thiadiazol-5-ylmethylsulfanyl]-phenoxy}-propionic acid,
2-Methyl-2-(2-methyl-4-{2-[3-(4-trifluoromethyl-phenyl)-[1,2,4]thiadiazol-5-yl]-ethyl}-phenoxy)-propionic acid,
2-(4-{2-[3-(3-Chloro-4-trifluoromethyl-phenyl)-[1,2,4]thiadiazol-5-yl]-ethyl}-2-methyl-phenoxy)-2-methyl-propionic acid, 2-Methyl-2-{2-methyl-4-[3-(4-trifluoromethyl-phenyl)-[1,2,4]thiadiazol-5-ylmethoxy]-phenoxy}-propionic acid,
2-Methyl-2-{2-methyl-4-[3-(4-trifluoromethoxy-phenyl)-[1,2,4]thiadiazol-5-ylmethoxy]-phenoxy}-propionic acid,
2-(4-{2-[3-(3-Fluoro-4-trifluoromethyl-phenyl)-[1,2,4]thiadiazol-5-yl]-ethyl}-2-methyl-phenoxy)-2-methyl-propionic acid,
2-(4-{2-[3-(3-Fluoro-4-methyl-phenyl)-[1,2,4]thiadiazol-5-yl]-ethyl}-2-methyl-phenoxy)-2-methyl-propionic acid,
2-Methyl-2-(2-methyl-4-{2-[3-(4-trifluoromethyl-phenyl)-[1,2,4]-thiadiazol-5-yl]-ethylsulfanyl}-phenoxy)-propionic acid,
2-(4-{2-[3-(3-Chloro-4-trifluoromethyl-phenyl)-[1,2,4]thiadiazol-5-yl]-ethylsulfanyl}-2-methyl-phenoxy)-2-methyl-propionic acid,
2-(4-{2-[3-(3-Chloro-4-trifluoromethyl-phenyl)-[1,2,4]thiadiazol-5-yl]-ethylsulfanyl}-2-methyl-phenoxy)-2-methyl-propionic acid,
2-Methyl-2-{2-methyl-4-[3-(4-trifluoromethyl-phenyl)-[1,2,4]thiadiazol-5-ylmethylsulfanyl]-phenylsulfanyl}-propionic acid,
2-{4-[3-(3-Chloro-4-trifluoromethyl-phenyl)-[1,2,4]thiadiazol-5-yl-methylsulfanyl]-2-methyl-phenylsulfanyl}-2-methyl-propionic acid,
2-{4-[3-(3-Fluoro-4-trifluoromethyl-phenyl)-[1,2,4]thiadiazol-5-ylmethylsulfanyl]-2-methyl-phenylsulfanyl}-2-methyl-propionic acid, and
2-{4-[3-(3-Fluoro-4-methyl-phenyl)-[1,2,4]thiadiazol-5-ylmethylsulfanyl]-2-methyl-phenylsulfanyl}-2-methyl-propionic acid.

30. A compound of claim 1, selected from:
2-Methyl-2-{2-methyl-4-[3-(4-trifluoromethoxy-phenyl)-[1,2,4]thiadiazol-5-ylmethylsulfanyl]-phenoxy}-propionic acid,
2-Methyl-2-{2-methyl-4-[3-(4-trifluoromethyl-phenyl)-[1,2,4]thiadiazol-5-ylmethoxy]-phenoxy}-propionic acid,
2-Methyl-2-{2-methyl-4-[3-(4-trifluoromethoxy-phenyl)-[1,2,4]thiadiazol-5-ylmethoxy]-phenoxy}-propionic acid,
2-{4-[3-(3-Chloro-4-trifluoromethoxy-phenyl)-[1,2,4]thiadiazol-5-ylmethylsulfanyl]-2-methyl-phenoxy}-2-methyl-propionic acid, and
2-{4-[3-(3,4-Dichloro-phenyl)-[1,2,4]thiadiazol-5-ylmethylsulfanyl]-2-methyl-phenoxy}-2-methyl-propionic acid.

31. A compound of claim 1, selected from:
2-Methyl-2-{2-methyl-4-[3-(4-trifluoromethoxy-phenyl)-[1,2,4]thiadiazol-5-ylmethoxy]-phenoxy}-propionic acid,
2-Methyl-2-{2-methyl-4-[3-(4-trifluoromethyl-phenyl)-[1,2,4]thiadiazol-5-ylmethoxy]-phenoxy}-propionic acid,
2-{4-[3-(3,4-Dichloro-phenyl)-[1,2,4]thiadiazol-5-ylmethoxy]-2-methyl-phenoxy}-2-methyl-propionic acid,
2-{4-[3-(3-Chloro-4-trifluoromethoxy-phenyl)-[1,2,4]thiadiazol-5-ylmethoxy]-2-methyl-phenoxy}-2-methyl-propionic acid,
2-Methyl-2-(2-methyl-4-{2-[3-(4-trifluoromethoxy-phenyl)-[1,2,4]thiadiazol-5-yl]-ethoxy}-phenoxy)-propionic acid,
2-(4-{2-[3-(3,4-Dichloro-phenyl)-[1,2,4]thiadiazol-5-yl]-ethyl}-2-methyl-phenoxy)-2-methyl-propionic acid,
2-Methyl-2-(2-methyl-4-{2-[3-(4-trifluoromethoxy-phenyl)-[1,2,4]thiadiazol-5-yl]-ethyl}-phenoxy)-propionic acid,
2-(4-{2-[3-(3-Chloro-4-trifluoromethoxy-phenyl)-[1,2,4]thiadiazol-5-yl]-ethyl}-2-methyl-phenoxy)-2-methyl-propionic acid,
2-(4-{2-[3-(3-Chloro-4-trifluoromethoxy-phenyl)-[1,2,4]thiadiazol-5-yl]-ethoxy}-2-methyl-phenoxy)-2-methyl-propionic acid,
2-(4-{2-[3-(3,4-Dichloro-phenyl)-[1,2,4]thiadiazol-5-yl]-ethoxy}-2-methyl-phenoxy)-2-methyl-propionic acid,
2-Methyl-2-(2-methyl-4-{2-[3-(4-trifluoromethoxy-phenyl)-[1,2,4]thiadiazol-5-yl]-ethoxy}-phenylsulfanyl)-propionic acid,
2-(4-{2-[3-(3-Chloro-4-trifluoromethoxy-phenyl)-[1,2,4]thiadiazol-5-yl]-ethoxy}-2-methyl-phenylsulfanyl)-2-methyl-propionic acid,
2-(4-{2-[3-(3,4-Dichloro-phenyl)-[1,2,4]thiadiazol-5-yl]-ethoxy}-2-methyl-phenylsulfanyl)-2-methyl-propionic acid,
2-Methyl-2-(2-methyl-4-{2-[3-(4-trifluoromethoxy-phenyl)-[1,2,4]thiadiazol-5-yl]-ethylsulfanyl}-phenylsulfanyl)-propionic acid,
2-(4-{2-[3-(3-Chloro-4-trifluoromethoxy-phenyl)-[1,2,4]thiadiazol-5-yl]-ethylsulfanyl}-2-methyl-phenylsulfanyl)-2-methyl-propionic acid, and
2-(4-{2-[3-(3,4-Dichloro-phenyl)-[1,2,4]thiadiazol-5-yl]-ethylsulfanyl}-2-methyl-phenylsulfanyl)-2-methyl-propionic acid.

32. A pharmaceutical composition, comprising a pharmaceutically acceptable carrier and a compound of claim 1.

33. A pharmaceutical composition, comprising a pharmaceutically acceptable carrier and a compound of claim 21.

34. A pharmaceutical composition, comprising a pharmaceutically acceptable carrier and a compound of claim 23.

35. A pharmaceutical composition, comprising a pharmaceutically acceptable carrier and a compound of claim 25.

36. A pharmaceutical composition, comprising a pharmaceutically acceptable carrier and a compound of claim 26.

37. A pharmaceutical composition, comprising a pharmaceutically acceptable carrier and a compound of claim 27.

38. A pharmaceutical composition, comprising a pharmaceutically acceptable carrier and a compound of claim 28.

39. A pharmaceutical composition, comprising a pharmaceutically acceptable carrier and a compound of claim 29.

40. A pharmaceutical composition, comprising a pharmaceutically acceptable carrier and a compound of claim 30.

* * * * *